US012728128B2

(12) United States Patent
John et al.

(10) Patent No.: US 12,728,128 B2
(45) Date of Patent: Sep. 8, 2026

(54) COMPOSITIONS AND METHODS FOR THE TREATMENT OF NEUROLOGICAL DISEASES AND DISORDERS

(71) Applicant: The Regents of the University of California, Los Angeles, CA (US)

(72) Inventors: Varghese John, Los Angeles, CA (US); Barbara Jagodzinska, Los Angeles, CA (US); Patricia Spilman, Los Angeles, CA (US); Jesus J. Campagna, Los Angeles, CA (US); Kanagasabai Vadivel, Los Angeles, CA (US); Michael E. Jung, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 1273 days.

(21) Appl. No.: 17/611,038

(22) PCT Filed: May 13, 2020

(86) PCT No.: PCT/US2020/032578
§ 371 (c)(1),
(2) Date: Nov. 12, 2021

(87) PCT Pub. No.: WO2020/232056
PCT Pub. Date: Nov. 19, 2020

(65) Prior Publication Data

US 2022/0305006 A1 Sep. 29, 2022

Related U.S. Application Data

(60) Provisional application No. 62/847,031, filed on May 13, 2019.

(51) Int. Cl.

| | |
|---|---|
| ***A61K 31/496*** | (2006.01) |
| ***A61K 9/107*** | (2006.01) |
| ***A61K 9/127*** | (2006.01) |
| ***A61K 31/155*** | (2006.01) |
| ***A61K 31/454*** | (2006.01) |
| ***A61K 45/06*** | (2006.01) |
| ***A61K 47/69*** | (2017.01) |
| ***A61P 25/28*** | (2006.01) |

(52) U.S. Cl.
CPC .......... *A61K 31/496* (2013.01); *A61K 9/1075* (2013.01); *A61K 9/127* (2013.01); *A61K 31/155* (2013.01); *A61K 31/454* (2013.01); *A61K 45/06* (2013.01); *A61K 47/6909* (2017.08); *A61K 47/6911* (2017.08); *A61K 47/6913* (2017.08); *A61P 25/28* (2018.01)

(58) Field of Classification Search
CPC .... A61K 31/496; A61K 47/6911; A61P 25/28
See application file for complete search history.

(56) References Cited

U.S. PATENT DOCUMENTS 3,907,864 A 9/1975 Biel et al.
2004/0191312 A1* 9/2004 Oksenberg ........... A61K 31/445 424/464
2015/0342909 A1 12/2015 Potter et al.
2022/0305006 A1 9/2022 John et al.

FOREIGN PATENT DOCUMENTS

WO WO-2006014136 A1 * 2/2006 ........... C07D 401/12
WO WO-2013/022278 A2 2/2013
WO WO-2013188452 A1 * 12/2013 ......... A61K 31/5377
WO WO-2015/026215 A1 2/2015
WO WO-2020/232056 A1 11/2020

OTHER PUBLICATIONS

Hettich et al., "The Anti-Diabetic Drug Metformin Reduces BACE1 Protein Level by Interfering with the MID1 Complex," PLOS One, 9(7):e102420 (2014).
International Search Report and Written Opinion for International Application No. PCT/US2020/032578 mailed Aug. 30, 2020.
Invitation to Pay Additional Fees for International Application No. PCT/US2020/032578 dated Jul. 15, 2020.
Saczewski et al., "Biological activities of guanidine compounds, 2008-2012 update," Expert Opinion on Therapeutic Patents, 23(8):965-995 (2013).
Partial European Search Report for EP Application No. 20805967.5 dated Jun. 16, 2023.
Extended European Search Report for EP Application No. 20805967.5 dated Sep. 18, 2023.
Glennon et al., "Arylguanidine and arylbiguanide binding at 5-HT3 serotonin receptors: A QSAR study" Bioorganic & Medicinal Chemistry, 11(20) Oct. 1, 2003, pp. 4449-4454.

* cited by examiner

*Primary Examiner* — Sarah Pihonak
*Assistant Examiner* — Mikhail O'Donnel Robinson
(74) *Attorney, Agent, or Firm* — Foley Hoag LLP; David P. Halstead; Alexander J. Chatterley

(57) ABSTRACT

In certain embodiments allosteric inhibitors of BACE are provided. Illustrative inhibitors include but are not limited to various metformin analogs.

20 Claims, 32 Drawing Sheets

Metformin 1-(2-fluorophenyl) biguanidine 1-(4-fluorophenyl) biguanidine

Proguanil 1-phenyl-biguanidine

Pep 65005

Metformin

JD004

JD008

JD001

JD002

JD003

JD005

JD006

JD007

JD009

JD010

JD012

JD013

JD014

JD011

Exo_BJ-63

Exo_BJ-70

Exo_BJ-66

Exo_BJ-58

1-trifluoromethoxyphenyl-3-(1-propionylpiperidin-4yl)

-TPPU

TPPU

Scheme 1: Synthesis of *symmetrical* metformin analogs.

Scheme 2: Synthesis of *un*symmetrical metformin analogs.

Scheme 3: Synthesis of *unsubstituted* analogs.

Scheme 4: Synthesis of *akyl and aryl* analogs.

C

Peptide 65005: Acetyl-N-L-T-T-Y-P-Y-F-I-P-L-$CONH_2$

Peptide 65006: Acetyl-LTTYPYFIPLP-$NH_2$

Peptide 65007: Acetyl-ALYPYFLPISAK-$NH_2$

Peptide 65008: Acetyl-YPYFIPA-$NH_2$

Peptide 65009: Acetyl-CYPYFIPAC-$NH_2$ (S-S)

D

*BACE inhibitor IV*

E $NH_2$-Lys-Thr-Glu-Glu-Ile-Ser-Glu-Val-Asn-Sta-Val-Ala-Glu-Phe-COOH

P10 P9 P8 P7 P6 P5 P4 P3 P2 P1 P1′ P2′ P3′ P4′

*BACE inhibitor 1*

B

Aβ in CHO-7W Cells

Ac-A-L-Y-P-Y-F-L-P-I-S-A-K-NH2

*Peptide 65007*

Ac-N-L-T-T-Y-P-Y-F-I-P-L-NH2

*Peptide 65005*

$NH_2$–K–T–E–E–I–S–E–V–N–Sta–V–A–E–F–COOH

P: 10–9–8–7–6–5–4–3–2 – 1 – 1'- 2' 3' 4'

E

Substrate and Enzyme IC50s

| | sAPPa | | BACE inh 4 | | BACE inh 1 | | P65005 | | P65007 | |
|---|---|---|---|---|---|---|---|---|---|---|
| Substrate | EC50 (μM) | IC50 (μM) | EC50 (μM) | IC50 (μM) | EC50 (μM) | IC50 (μM) | EC50 (μM) | IC50 (μM) | EC50 (μM) | IC50 (μM) |
| APP (sAPPβ) | <1 | | <1 | | 8 | | >10 | | 10 | |
| NRG1 | >10 | | <1 | | >10 | | >10 | | >10 | |
| PSGL1 | >10 | | <1 | | >10 | | >10 | | >10 | |
| MBP-C125 | | 0.08 | | NA | | 0.2 | | >100 | | 2.8 |
| P5-P5' | | >2 | | 0.01 | | 0.16 | | >100 | | >100 |

COMPOSITIONS AND METHODS FOR THE TREATMENT OF NEUROLOGICAL DISEASES AND DISORDERS

RELATED APPLICATIONS

This application is the U.S. National Stage of PCT/US2020/032578, filed May 13, 2020, which claims the benefit of U.S. Provisional Patent Application No. 62/847,031, filed on May 13, 2019. The contents of each application are hereby incorporated by reference in their entirety.

BACKGROUND

Alzheimer's disease, the most common age-related dementia, is a devastating neurological disorder currently afflicting more than 5.5 million Americans at costs that exceed $200 billion per year. AD is characterized by the presence of senile plaques largely comprising amyloid-β peptide, and neurofibrillary tangles resulting from hyperphosphorylation of tau (p-tau), in brain tissue. AD patients suffer from deficits in cognition, learning, and memory; and have impaired long-term potentiation as well as disruption in cholinergic neurotransmission. Only two types of drugs are currently approved for the treatment of AD: acetylcholinesterase (AChE) inhibitors and N-methyl-D-aspartyl (NMDA) receptor antagonists; the former enhance activity of the neurotransmitter acetylcholine and the latter reduce excitotoxicity resulting from NMDA receptor over-activation. Both types of drugs only provide temporary, symptomatic relief and a modest delay in cognitive decline in patients, with beneficial effects typically only being maintained up to 36 months. Identification of the Aβ peptide, cloning of the amyloid precursor protein gene, and findings by many that specific mutations in APP result in familial early-onset AD led to the establishment of the Amyloid Cascade Hypothesis of AD. This hypothesis suggests that it is the over-production of Aβ, or reduced clearance, that drives the development and progression of the disease. Aβ is derived from processing of full-length APP, whereby sequential cleavage by β-secretase BACE1 (BACE) and the γ-secretase complex produces first soluble APPβ (sAPPβ) and the b-C-terminal fragment (βCTF), and then (from βCTF) Aβ of a variety of lengths (species). Alternatively, α-secretase cleavage (putatively by ADAM10) results in production of trophic, synapse-supporting peptides soluble APPα (sAPPα) and the α-C-terminal fragment (αCTF).

Early attempts at drug discovery for AD included development of therapeutics providing either active or passive immunity to Aβ and/or Aβ-plaques, or inhibition of γ-secretase activity. Both approaches suffered from the lack of clinical efficacy, and particularly for the γ-secretase inhibitory strategy, produced undesirable side effects in the clinic. These side effects were attributed to inhibition of cleavage of non-APP substrates, a concern that exists for current direct β-secretase inhibitors now in the clinic.

Since the identification and purification of the aspartyl protease BACE from AD brain tissue by affinity purification utilizing an immobilized early peptidic BACE inhibitor, structure-based design approaches have led to the development of potent active site-directed BACE inhibitors, some of which have gone into clinical testing. The validity of BACE inhibition as a target is not only supported by the finding of a BACE site mutation in a Swedish family that greatly increases β cleavage and risk for AD but also, quite importantly, by the identification of a BACE site mutation in an Icelandic population that decreases β cleavage and provides protection against AD onset. Even a modest decrease BACE activity can reduce Aβ.

As a therapeutic strategy, BACE inhibition is thought to be relatively safe due to studies reporting BACE knockout mice are healthy and show no overt pathology; however, there is still concern around inhibition of other substrates of BACE, particularly neuregulin-1 (NRG1). Lessons learned during the development of γ-secretase inhibitors (GSIs) in the past should provide some guidance to a BACE inhibitory strategy. So, while in pre-clinical studies effective GSIs almost completely arrested Aβ production, many also inhibited cleavage of some of the approximately 30 known additional non-APP substrates, including key protein Notch-1. Therefore, a limitation to the BACE protease inhibitory strategy is similar to that for GSIs: selectivity and the risk for inhibition of cleavage of non-APP protein substrates such as PSGL1, LRP, and/or NRG1. The ideal BACE inhibitor, therefore, would be selective for APP as the substrate, and for the BACE enzyme relative to other aspartyl proteases such as the homolog BACE2 or the housekeeping enzyme cathepsin D (Cat-D).

While currently there is debate around continuing to target Aβ in AD therapeutic development, this comes as a result of clinical failure of Aβ-directed immunotherapies and the GSIs. In general, these studies may have been hindered by timing of treatment (too late in the disease course) and patient selection, that is, enrollment of patients without AD pathology. The former factor may have led to the recent decision of Merck to cease its EPOCH clinical trial of BACE inhibitor verubecestat in patients with mild to moderate AD, a stage at which the disease maybe too advanced for a BACE inhibitor to produce significant improvement. Merck's APECS trial of the same inhibitor in patients with prodromal AD (sometimes referred to as Mild Cognitive Impairment or MCI) will continue. In the case of immunotherapy, a significant adverse effect of ARIA (amyloid-related imaging abnormalities—edema/effusion) was reported in many patients which confounded results and prevented efficacy. This adverse reaction results from an inflammatory response to and clearance of pre-existing plaques in the brain vasculature in particular—such an effect would not be expected for a therapeutic that disrupts Aβ production. For GSIs, lack of substrate selectivity contributed to their clinical failure. The ultimate success of an allosteric BACE inhibitor in the clinic will depend upon accurate diagnosis and early intervention.

SUMMARY

This application pertains to the discovery of allosteric inhibitors of BACE1 (BACE) that are effective, safe, and can be developed as novel therapeutics for Mild Cognitive Impairment and Alzheimer's disease. Our recent studies show for the first time that sAPPα—product of α-secretase cleavage of amyloid precursor protein—is a potent allosteric inhibitor of the β-secretase BACE (IC50~25 nM), the rate-limiting enzyme in amyloid-β production. The allosteric inhibition of BACE by sAPPα is similar to that reported for a BACE-inhibiting antibody from Genentech shown by co-crystallization (pdb:3R1G) to bind to an exosite on BACE resulting in modulation of distal S6 and S7 subsites and thus preventing a long substrates such as the amyloid precursor protein from binding the enzyme but not the short P5-P5' substrate. Similarly, Kornacker et al. reported on peptides that can act as allosteric BACE inhibitors by binding to an exosite. However, both the peptidic and antibody-based allosteric inhibitors present delivery challenges.

In certain aspects, disclosed herein is a discovery approach to screen, optimize, and identify small-molecule brain-penetrant allosteric BACE inhibitors as lead candidates that are orally available and can lower production of amyloid-β peptide. Furthermore, as increased BACE activity and Aβ production are implicated in other neurological conditions, the drugs identified herein are believed to also have broader use in treatment of, inter alia, cerebral amyloid angiopathy, poor outcome after TBI or stroke, and in ALS.

The direct BACE inhibitors now in the clinic bind to the active-site groove and may also inhibit cleavage of other BACE substrates such as PSGL1, LRP and/or NRG1. Substrate and enzyme specificity are important properties that could determine progress of clinical development for BACE inhibitors. Allosteric BACE inhibitors have the potential to be substrate- and enzyme-selective; furthermore, exosite-binding BACE inhibitors do not need polar groups for interaction with the catalytic aspartyl residues and are therefore likely to be more brain-penetrant.

The studies described herein using in silico docking have led to identification of a series of metformin analogs predicted to bind to a BACE exosite and these molecules have been shown to be allosteric BACE inhibitors in the assays. This finding provides initial validation of this approach. Such small molecules blood-brain barrier permeability provide candidates with for proof-of-concept testing of this physiologically relevant mechanism, and can be developed as promising new therapeutics for AD.

Without being bound to a particular theory, it is believed that for GSI selectivity and to reduce the risk of inhibition of cleavage of non-APP protein substrates an allosteric BACE inhibitor—that is, one that interacts with an exosite remote from the active site and alters the conformation of docking subsites—is ideal given the differential subsite specificity for various substrates and the differences in the Loop F region between BACE and other aspartyl proteases. Allosteric inhibitors may have greater safety due to potential selectivity for both enzyme and substrate.

In one aspect, the present disclosure provides an allosteric BACE inhibitor said inhibitor comprising a compound according to the formula:

I or

II or

III

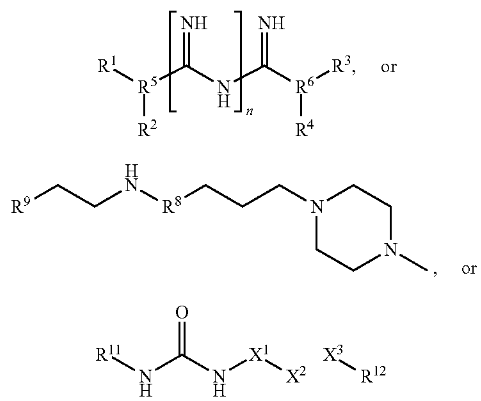

wherein:

$X^1$ is $CH_2$ or C(O);

$X^2$ is $CH_2$ or $CHR^{13}$;

$X^3$ is $CH_2$, O, or S;

$R^{11}$ is heterocyclyl;

$R^{12}$ is heteroaryl or heterocyclyl;

$R^{13}$ is alkyl or aralkyl;

n is 1, 2, or 3;

$R^5$ is CH or N;

$R^6$ is CH or N;

$R^1$ and $R^2$ are independently selected from H, Me, OMe, Pr, and substituted or unsubstituted phenyl; or $R^5$ taken with $R^1$ and $R^2$ is a substituted or unsubstituted homocycle or a substituted or unsubstituted heterocycle;

$R^3$ and $R^4$ are independently selected from H, Me, OMe, Pr, and substituted or unsubstituted phenyl; or N taken with $R^1$ and $R^2$ is a substituted or unsubstituted heterocycle;

$R^8$ is $CH_2$, C═O, or $SO_2$; and $R^9$ is selected from a substituted or unsubstituted indole, a substituted or unsubstituted phenyl, a substituted or unsubstituted carbazole, and

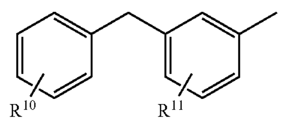

, where $R^{10}$ and $R^{11}$ are independently H or halogen;

or a pharmaceutically acceptable salt, ester, amide, tautomer, or prodrug thereof; and wherein said compound is not metformin or proguanil.

BRIEF DESCRIPTION OF THE DRAWINGS

FIGS. 2A & 2B show that sAPPα inhibits (FIG. 2A) BACE activity in the MBP-APPC125 (IC50~25 nM), but not the (FIG. 2B) P5-P5' assay. sAPPβ that is shorter in length than sAPPα by 16 amino acids did not inhibit BACE in either assay. FIGS. 2C & 2D show that SAXS analysis revealed differences in 3D structures of (FIG. 2C) sAPPα and (FIG. 2D) sAPPβ.

FIG. 3A shows that the anti-BACE1 antibody [upper left] interacts with BACE1 (lower right) at the residues circled in red and alters the position of loop D and loop F and these alterations change the S6 and S7 subsites on BACE preventing binding of a long substrate. FIG. 3B shows that the original conformation is altered upon antibody interaction and a loop changes position (arrow). This may affect substrate binding.

FIG. 4A shows that if the exosite is empty, substrates are cleaved. Allosteric inhibitor binding of an exosite changes the conformation of subsite S6 and S7 and can prevent docking/cleavage of a long (FIG. 4B), but not a short (FIG. 4C) substrate.

FIG. 6A shows that neither Pep 65005 nor sAPPα inhibit BACE activity in the short P5-5' assay; direct inhibitor BACE IV does inhibit. FIG. 6B shows that all three inhibit activity in the MBP-APPC125 assay. FIG. 6C shows the profiles of β secretase inhibitor 1 (β-sec Inh 1) and BACE IV indicate direct inhibition, whereas sAPPα and 65005 are allosteric inhibitors, inhibiting BACE in the long-versus short-substrate assays.

FIG. 7A shows that as compared to direct BACE inhibitor binding, binding of the antibody induces loop F displacement.

FIG. 8A shows a distinct conformational difference in BACE structure was seen at the P5-P7 binding site (circled) between long substrate and Ab binding. FIG. 8B shows that DDG prediction reveals the putative exosite site. FIG. 8C is a structural representation that shows a deep pocket at the putative exosite (arrow). FIG. 8D shows that computational docking reveals an example of a compound binding to the allosteric site.

FIG. 17A shows that sAPPβ Peptide 65005, and inhibitor BACE IV all elicit dose-response inhibition of BACE cleavage of relatively long substrate MBP-APPC125; the substrate is shown below the graph. FIG. 17B shows that only BACE IV inhibits BACE cleavage of short substrate P5-P5'; the substrate is shown below the graph. FIG. 17C shows the sequence of Peptide 65005 (SEQ ID NO:1) and other peptide analogs (65006 (SEQ ID NO:2), 65007 (SEQ ID NO:3), 65008 (SEQ ID NO:4), 65009 (SEQ ID NO:5)) that could bind the exosite is also shown. FIG. 17D shows the structure of BACE IV, used for comparison in the assays, is shown. FIG. 17E shows the sequence of statine BACE inhibitor 1, used in crystallization studies (1×N3) to generate structures shown in FIGS. 18 and 19, and the BACE subsites (below) with which it interacts, is shown. It interacts with all the BACE subsites.

FIG. 18A shows that Loop F is significantly displaced after a 50 ns simulation experiment using Peptide 65005 binding. FIG. 18B shows that Loop D and both Loop F and D 1 strands positions are altered as a result of Peptide 65005 binding; the unbound conformation in shown in fuchsia. FIG. 18C shows that the BACE peptides with which Peptide 65005 interacts are shown. FIG. 18D shows the location and electrostatic interaction of Peptide 65005 with the BACE exosite and Loops D and F are shown.

FIG. 19A shows that the antibody binding exosite described in Wang et al. for the allosteric inhibitor antibody is shown in orange. FIG. 19B shows the exosite described by Kornacker et al. for Peptide 65005 and is revealed to be very similar to the antibody exosite (see circles for A and B). FIG. 19C shows that in a conformation resulting from BACE inhibitor 1 binding, the Peptide 65005 exosite is seen to include Loops F, D, and C. FIG. 19D shows an overlay of conformations when the antibody is bound (3R1G) and when peptide 65005 is bound reveals that those conformations are extremely similar. The Loop F region is very dynamic and is in motion during binding.

FIG. 20A shows that APP may be cleaved by ADAM10 to generate neurotrophic fragments sAPPα and αCTF or, alternatively, by BACE. In BACE cleavage, a dimerized BACE:APP complex is endocytosed to a relatively acidic endocytic compartment wherein APP is cleaved generating sAPPβ and βCTF. The latter is then cleaved by γ-secretase to form amyloid-β (Aβ) and the APP intracellular domain (AICD). FIG. 20B shows that BACE comprises an exosite (a binding site remote from the active site), that when unoccupied (left) allows processing of a variety of substrates. When an allosteric inhibitor binds at the exosite, however, it induces a conformational change in specific BACE subsites that inhibits long APP substrate cleavage (center). In contrast, even with the exosite occupied, a short substrate that does not require interaction with subsites S7 and S6 still binds and its cleavage is not affected (right). FIG. 20C shows that in the MBP-APPC125 (long substrate) assay, sAPPα shows the most potent inhibition of BACE, followed by (of the inhibitors tested) BACE inhibitor 1 (BACE Inh 1), and 65007. FIG. 20D shows that in the P5-P5' (short substrate) assay, 65007 shows no inhibition and sAPPα only very slight inhibition above 0.5 μM of BACE activity, whereas both BACE inhibitor 4 (BACE Inh 4) and BACE Inh 1 inhibit BACE. The substrates are shown beneath the assays (C&D).

FIG. 21A shows that BACE inhibitor 1 (BACE Inh-1), BACE inhibitor 4 (BACE Inh-4), 65007, and sAPPα all show dose-response inhibition of sAPPβ, product of APP cleavage by BACE, which was significant for BACE Inh 4 at all concentrations (concentrations higher to lower, left to right, for each inhibitor) and for 65007 at 10 μM. Due to limits in 65005 solubility, only one concentration—10 μM—was used. FIG. 21B shows that a similar dose-response was seen in Aβ production (which requires β secretase of βCTF) for all the inhibitors tested (except 65005), with significance at the highest concentration used for each. FIG. 21C shows the sequences of the peptide inhibitors are shown. FIG. 21D shows the sequence of BACE Inh 1, and the peptide subsites (P:) on BACE with which each BACE Inh 1 amino acid interacts, is shown below. FIG. 21E The structure of BACE Inh 4 is shown.

FIG. 22A shows that BACE inhibitor 4 (BACE Inh 4) inhibition of NRG1 cleavage was >50% at 0.1 μM. BACE inhibitor 1 (BACE Inh 1) did not inhibit cleavage of NRG1 up to 20 μM. Both 65005 and 65007 showed inhibition of about 30% at 100 μM, but sAPPα did not inhibit NRG1 cleavage by BACE at the concentrations used. FIG. 22B shows that the result were very similar for NRG1 cleavage, with BACE Inh 4 showing >50% inhibition at 0.1 μM, BACE inhibitor 1 (BACE Inh 1) showing some slight inhibition above 5 μM, and neither 65007 nor sAPPα showing inhibition. FIG. 22C shows that when substrate cleavage product levels (a low value represents inhibition) are compared side-by-side for APP, PSGL1, and NRG1 all tested at 10 sAPPα is the most selective for APP, followed by 65007 (BACE Inh 1 showed some inhibition of NRG1 cleavage), and BACE Inh 4; 65005 was a weak inhibitor of BACE in all assays. FIG. 22D shows that sAPPα did not inhibit Cat D activity, and 65007 and BACE Inh 4 only did so at much higher concentrations than BACE Inh 1. Peptide 65007 at higher concentrations may interact with Cat D at sites with less favorable binding energy than near the Loop F of BACE, and elicit some inhibition. FIG. 22E shows that the EC50s from cell-based experiments, and IC50s from cell-free assays for the inhibitors and substrates used here are shown, and further support that an allosteric mechanism for BACE inhibition confers selectivity by sAPPα and 65007 of APP as a substrate.

FIG. 23A shows the location and binding interaction of 65007 (yellow) with the BACE exosite and Loops D and F are shown. FIG. 23B shows that Loop F, Loop Dand both Loop F and D β strands (box) positions are altered as a result of 65007 binding (beige); the unbound enzyme structure is shown in fuchsia. FIG. 23C the BACE residues with which 65007 (yellow) interacts in the Loop F region are shown. FIG. 23D Conformational overlay of the enzyme bound to the antibody (pdb: 3R1G, green) and to the peptide 65007 (beige) after the 50 ns simulation shows extremely close similarity. The Loop F itself is very dynamic and is in motion during binding.

FIG. 24A shows immunoblots for full-length (top to bottom) CHL1, L1CAM, NrCAM, neurofascin, and loading control α-tubulin are shown. Samples are from mouse primary cortical neurons exposed to inhibitors at the concentrations listed for 24 hours.

FIG. 25A shows the inhibition of BACE cleavage of APP as reflected by a decrease in sAPPβ is elicited by BACE inhibitor 4 (BACE Inh 4) at 1 μM and Peptide 65007 at 10 μM.

DETAILED DESCRIPTION

Figure 1:
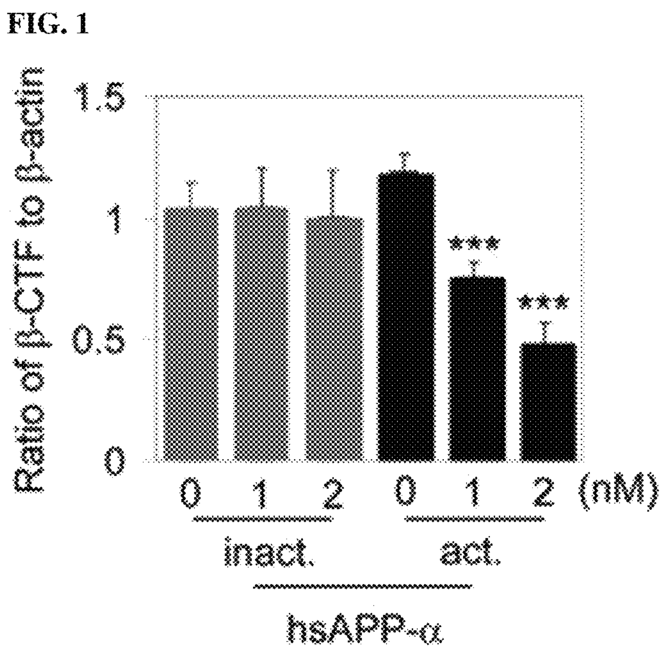
FIG. 1 shows that sAPPα is a potent BACE inhibitor. Active sAPPα decreases βCTF in a dose dependent manner, while inactive sAPPα does not have this effect.

The trophic effects of α-secretase APP cleavage product sAPPα are well-established, and in 2012, Obregon et al expanded the known effects of sAPPα by showing it can act as an inhibitor of BACE both in vitro and in vivo. Using antibodies to block sAPPα activity, they revealed that only active, but not antibody-inactivated, sAPPβ could reduce the ratio of BACE cleavage product 6 CTF relative to actin (FIG. 1). Studies performed in the lab, prompted by the observation that in vivo sAPPα-enhancing compounds such as tropisetron and analogs proportionately reduced sAPPα, led the discovery that it is not only is sAPPβ a BACE inhibitor, but the inhibitory activity is conformation-dependent and likely allosteric.

Figure 2:
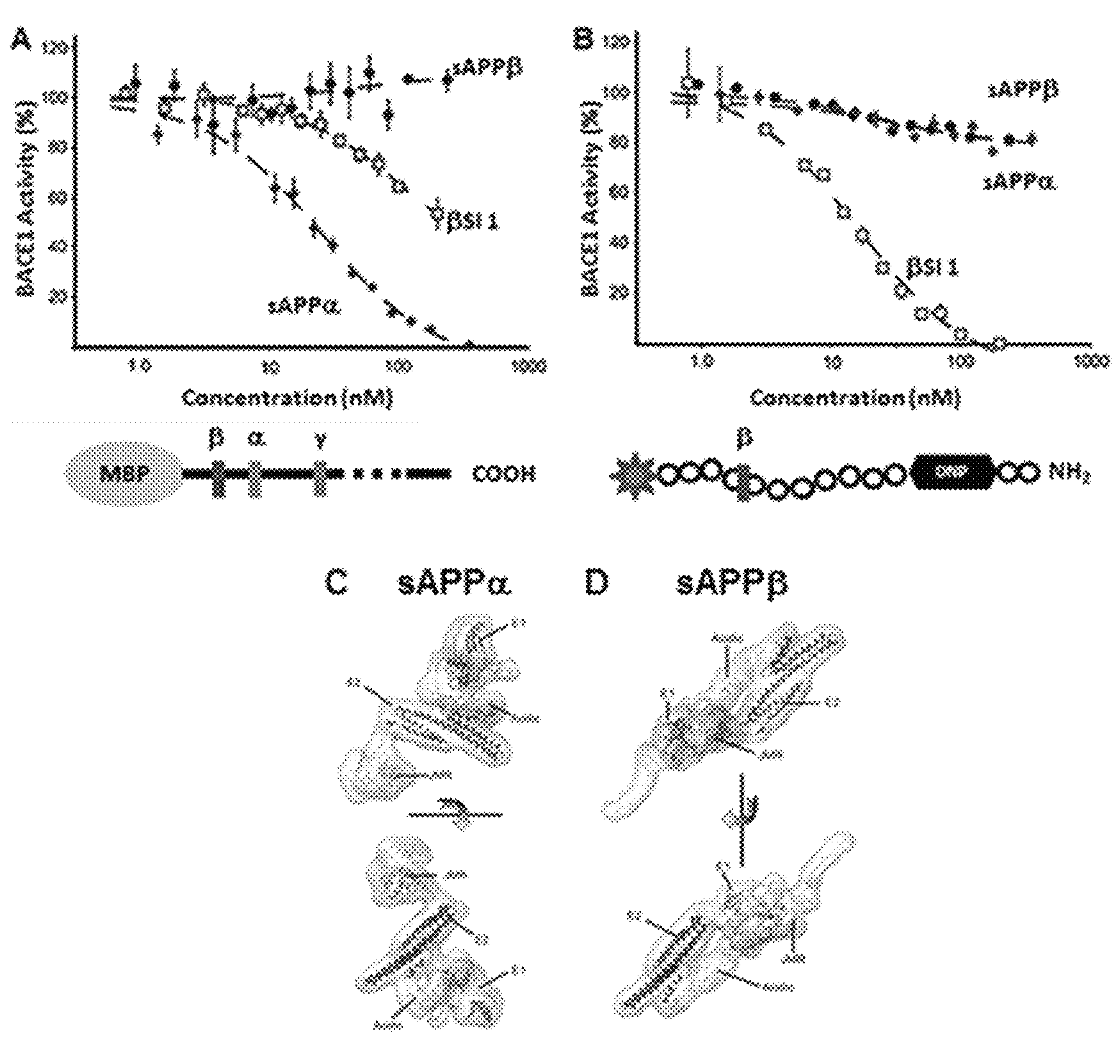
FIG. 2A-D, shows that sAPPα selectively inhibits BACE cleavage of MBP-APPC125.

Cell-free enzyme assays, such as recombinant BACE, and known BACE inhibitor 1 (β S1), revealed that recombinant sAPPα—but not recombinant sAPPβ—is a potent inhibitor of BACE cleavage of substrate MBP-APPC125 (FIG. 2, panel A). Interestingly, neither sAPPα nor sAPPβ inhibited cleavage of the short P5-P5' substrate (FIG. 2, panel B). The MBP-APPC125 (maltose binding protein fused to the C-terminal 125 amino acids of APP) substrate is much longer than the commercially available substrate P5-P5' (R & D Systems cat #ES004) (FIG. 2, panel B, lower). Small-angle X-ray scattering (SAXS) and intrinsic fluorescence studies indicated this was due to significant conformational differences between the two protein fragments (FIG. 2, panels C and D). Thus, sAPPα is the only known endogenous inhibitor of BACE and can play a role in self-regulation of APP processing. Such self-regulation can be hypothesized to be useful not only in neurodegenerative diseases such as AD, but also in other conditions such as traumatic brain injury where there is a transient increase in APP and BACE cleavage. Other products of APP processing also regulate enzymes in the APP cleavage pathway(s): αCTF has been shown to inhibit γ-secretase activity and Aβ has recently been revealed to have ADAM10 inhibitory activity.

While allosteric inhibitors of serine, cysteine, and metallo-proteases are known, this is not the case for aspartyl proteases. The only other naturally-occurring proteinaceous inhibitors of aspartyl proteases are porcine pepsin inhibitor PI-3 and the yeast-derived inhibitor; both of these proteins inhibit by competitive binding to the active site of the enzyme.

The mechanism of BACE inhibition by sAPPα is similar to an allosteric BACE inhibitor antibody (Ab) from Genentech/Roche. The inhibitory profile of sAPPβα is similar to that previously reported for an inhibitory anti-BACE antibody from Genentech/Roche. The Ab is a potent inhibitor of cleavage of a long substrate by BACE but shows only weak inhibition of cleavage of a short P5-P5' substrate. Using a competition binding ELISA experiment with the active site-binding (direct) BACE inhibitor OM-99, Atwal et al. showed that this inhibitor does not compete with Ab binding to BACE, thus the Ab does not bind the active-site. Further co-crystallization studies (pdb: 3R1G) showed the Ab bound to a site remote from the active site on BACE—an exosite. Therefore, while most BACE inhibitors currently under development interact with the active site and prevent or reduce cleavage, the antibody interacts with an exosite and is an allosteric inhibitor.

Figure 3:
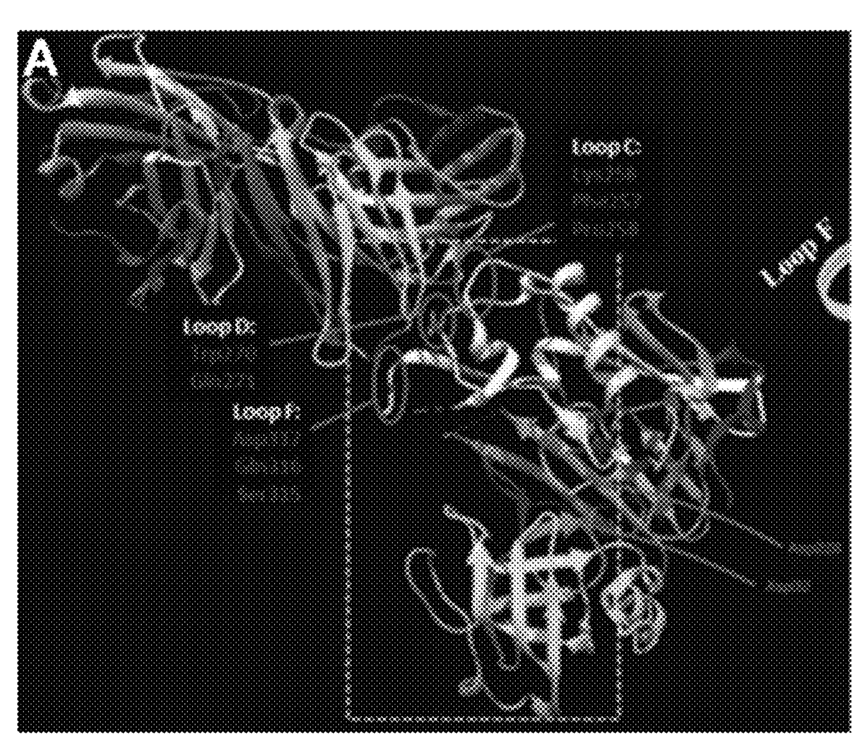
FIGS. 3A & 3B illustrate an example of allosteric inhibition of BACE1 by an antibody from Genentech/Roche.
Figure 3:
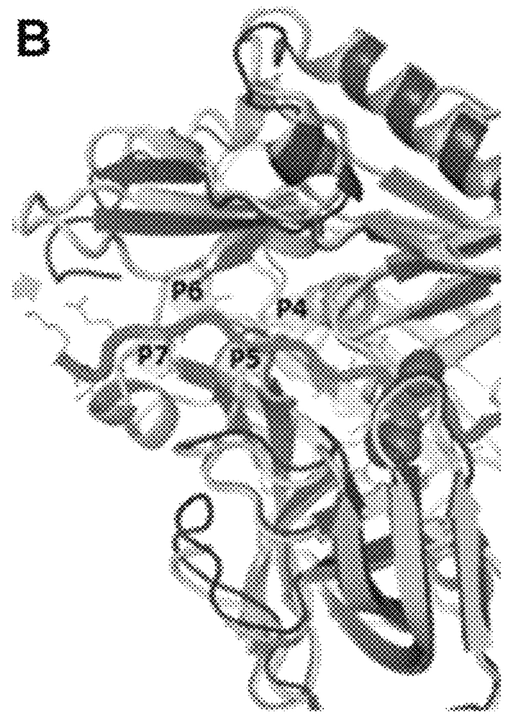

The antibody binding to the exosite (FIG. 3, panel A), results in the displacement of a loop (Loop F, FIG. 3, panel B, yellow arrow) near the S6 and S7 substrate binding region of the active site thus distorting these subsites. This conformational change prevents the proper binding of the long substrates, such as APP, but not short ones.

Figure 4:
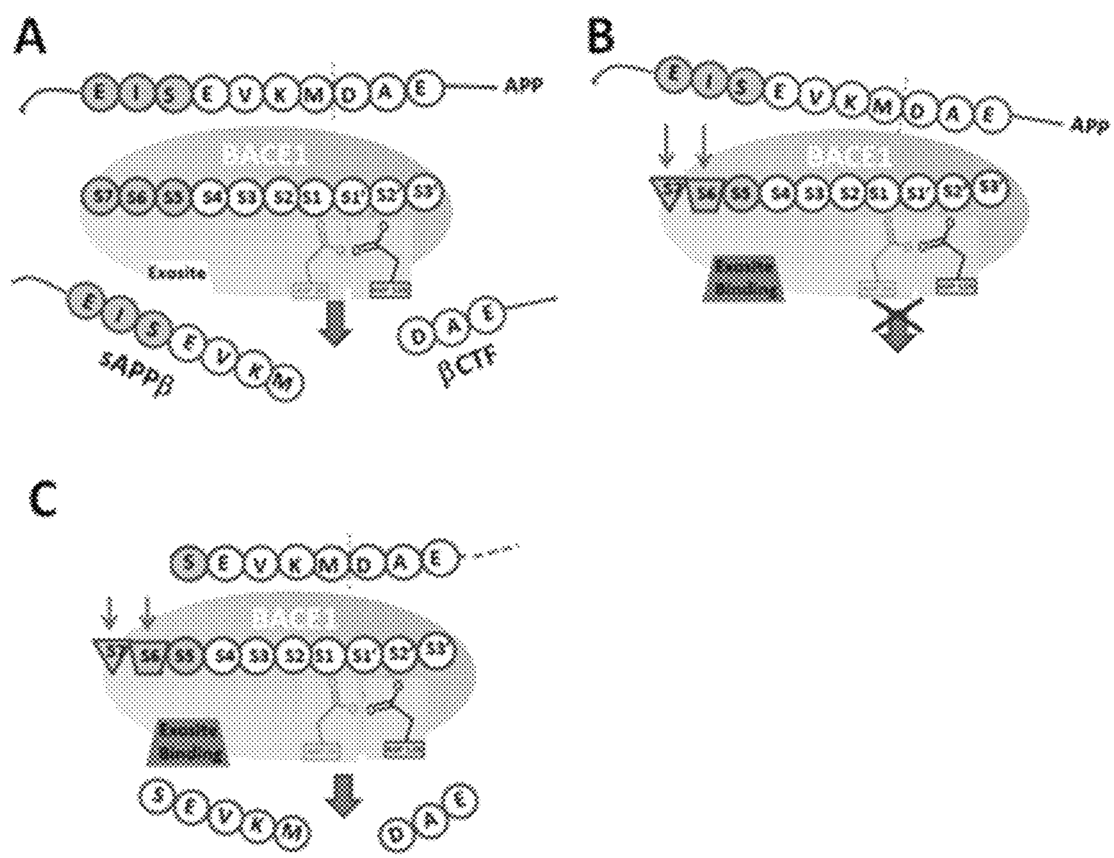
FIGS. 4A-C illustrate exosite binding and BACE inhibition.

As illustrated in FIG. 4, panel A, when the exosite is empty, a long substrate can dock properly in the active site and be cleaved by the enzyme. In the presence of an exosite-binding inhibitor, the docking site conformation around Loop F is altered, obstructing proper interaction of the long substrate with subsites S6 and S7 in the active site and preventing substrate cleavage (FIG. 4, panel B). Docking of the short substrate is, however, not affected by this conformational change and it is cleaved normally (FIG. 4, panel C). Thus, determination of inhibition in cell-free enzyme assays using the long and short substrates provides a tool for ascertaining allosteric inhibition, and was used as part of compound screening described herein. It should be noted there may be multiple exosites on BACE, and sAPPβ may not necessarily interact with the same site as the antibody, however the ultimate effect should be similar and result in Loop F displacement and distortion of the S6 and S7 subsites.

Figure 5:
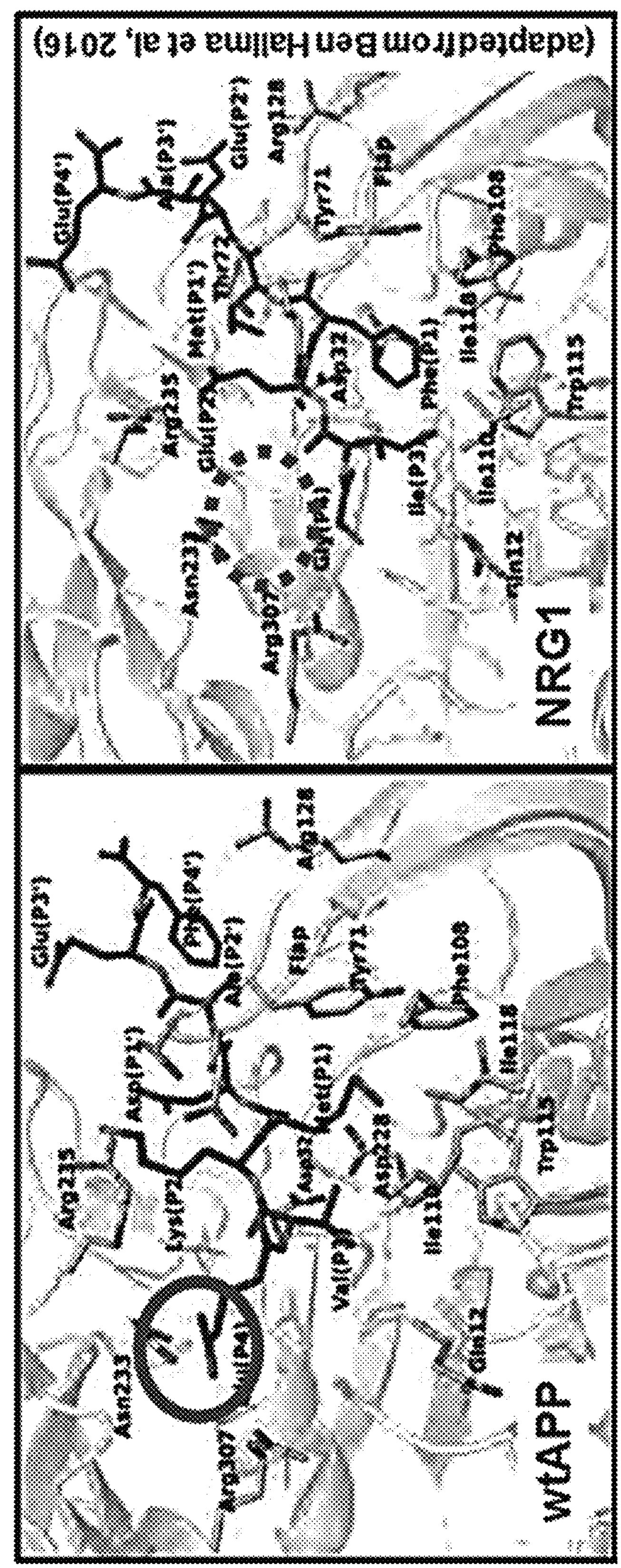
FIG. 5 illustrates interactions of APP and NRG1 with BACE. The positions of wildtype APP (wtAPP, left) and NRG1 (right) upon docking with the BACE are distinct. An inhibitor that alters conformation in the area circled in red may only affect wtAPP docking, as that site is vacant (dashed circle) for NRG1.

Given that individual substrates may interact with BACE with differing amino acid residues having varying affinities at different subsites, as seen for APP and NRG1 in FIG. 5, it is believed that distortion of the S6 and S7 subsites by an allosteric inhibitor has differing effects on binding of substrates such as APP versus NRG1. This provides the potential for an allosteric inhibitor to inhibit APP, but not NRG1, cleavage. An allosteric inhibitor also provides possibility of enzyme selectivity due to the presence of Loops D and F that are unique to BACE1 structure and is lacking in BACE2, Cat-D, and other aspartyl proteases. Such enzyme selectivity was shown for the anti-BACE Ab, which did not inhibit either BACE2 or Cat-D activity. Thus, identification of an enzyme-selective allosteric inhibitor is possible, and this selectivity can be ascertained in early pre-clinical development. Therefore, small molecule allosteric inhibitors of BACE may overcome the limitations of conventional BACE This therapeutic approach targets identification of allosteric inhibitors of BACE that interact with an exosite on BACE, inhibits the cleavage of APP, and lower the production of sAPPβ, βCTF, and ultimately Aβ peptide.

Disclosed herein is a Kornacker peptide (Pep 65005) that interacts with the Loop F region of BACE (see, e.g., Example 1). This interaction can cause the Loop F displacement and has the potential to distort the distal subsites S6 and S7 of BACE similarly to the Genentech Ab and thus prevent binding of the long substrate. Furthermore, through in silico alanine mutations of the BACE protein backbone, a new exosite distinct from the peptide 65005 Kornacker binding site has been identified (see FIG. 8). This exosite has a deep-pocket favorable for small molecule binding, and the in-silico alanine mutation studies suggest that interaction with this exosite could result in Loop F displacement. We have also performed an initial round of in silico screening using this exosite and have identified 'hits' that are potential allosteric inhibitors of BACE. An additional feature of exosite-binding BACE inhibitors is that they need not have to interact with the catalytic site aspartyl groups using a polar residue such as a hydroxyl or amino moiety; thus they likely would be more brain-penetrant.

Without being bound to a particular theory it is believed the work described herein represents the first approach to screen and develop small molecules that bind to a BACE exosite and inhibit BACE cleavage of APP. Allosteric BACE inhibitors have greater potential for selectivity for the substrate APP and the enzyme, and have improved brain penetrance. Such small molecule therapeutic candidate(s) could act similarly to sAPPα to restore normal APP processing in MCI and AD. In addition, as upregulation of Aβ production is implicated in development of cerebral amyloid angiopathy, poor outcome after TBI or stroke, and progression of amyotrophic lateral sclerosis, an allosteric inhibitor of BACE is believed to also have a potential role in treatment of these other neurological diseases/conditions.

Disclosed herein is an innovative approach to therapeutic development in AD based on these recent findings. Our studies have revealed for the first time that the endogenous protein sAPPα can act as an allosteric inhibitor of BACE, a key enzyme responsible for Aβ production. This finding has provided the basis for a new approach to BACE inhibition by identification of small molecules that mimic sAPPα's allosteric inhibition of BACE. It is believed this approach has led to enzyme- and substrate-selective BACE inhibitor (s).

The assays described herein used to characterize sAPPα's mechanism of BACE inhibition may be adapted to high throughput screening compound libraries and secondary assays used to identify validated small molecule hits as allosteric BACE inhibitors. In addition, methods described herein including surface plasmon resonance, top-down mass spectrometry (Top-down MS), and co-crystallization studies performed as part of the drug discovery effort can be used to reveal both the site(s) of interaction of compounds with BACE and provide an iterative structure-based approach for hit-to-lead optimization. These supporting mechanistic studies, combined with in silico modeling, provide molecules that are allosteric inhibitors of BACE as well as support SAR elucidation and therefore increase the opportunity for success.

Preclinical in vivo testing of lead candidates can provide proof-of-concept of this novel approach. The ultimate goal is to develop a potent, APP and BACE-selective, orally available, and brain-penetrant lead candidate with a high therapeutic index as the first allosteric BACE inhibitor that can progress to the clinic. Such a candidate could then move on to testing to determine its efficacy in patients with MCI.

With small molecule allosteric inhibitors of BACE are described herein the co-crystallization of BACE and sAPPα can also be pursued. If successful, the resultant information can further aid inhibitor design.

In various embodiments at least four major innovations are described herein: i) identification of small molecule allosteric BACE inhibitors that modulate the Loop F region of the enzyme and distort distal subsites S6 and S7; ii) identification of compounds that are both BACE enzyme- and APP substrate-selective, with enhanced brain penetrance iii) characterization of a new exosite identified by the preliminary in silico modeling, and iv) identification of an initial set of "hits" based on metformin through preliminary in silico screening for compounds that interact with the new exosite that will be amenable for hit-to-lead optimization.

The application seeks to shift the current research and therapeutic paradigm in AD through identification of allosteric BACE inhibitors that have the potential to be both brain penetrant and substrate/enzyme-selective. Furthermore, as allosteric inhibitors do not bind the catalytic site they have the possibility of being used in combination with direct active-site BACE inhibitors in the future to get synergistic efficacy. This is similar to the effective combination 'Kaletra' used in HIV protease inhibition where the combination was more effective than the individual protease inhibitors. The compositions and methods described herein can have clinical impact beyond AD, and are believed to be useful in treatment of pathological conditions where there is an increase in APP levels and BACE activity such as in TBI, stroke, ALS, and CAA.

Figure 6:
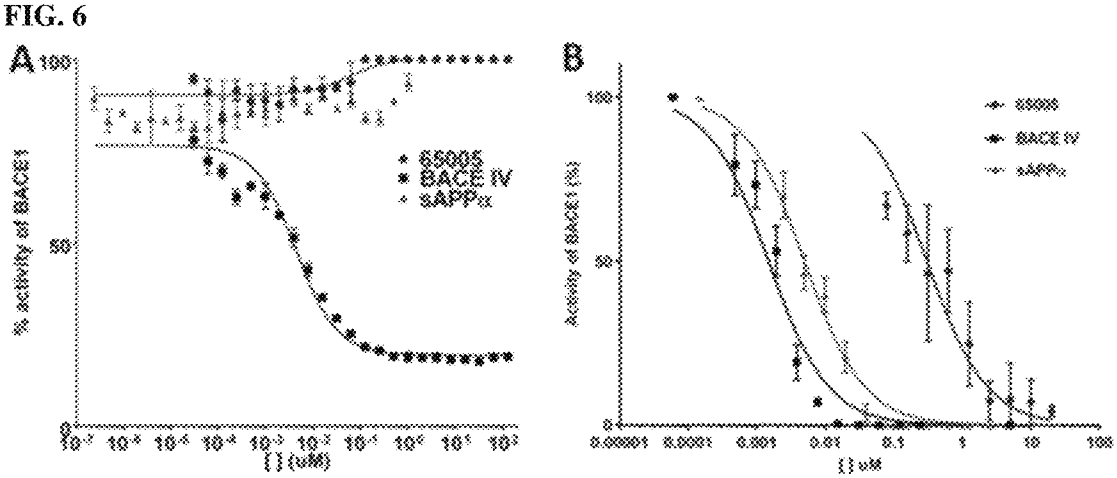
FIGS. 6A-C show that pep 65005 acts as an allosteric inhibitor of BACE.
Figure 6:
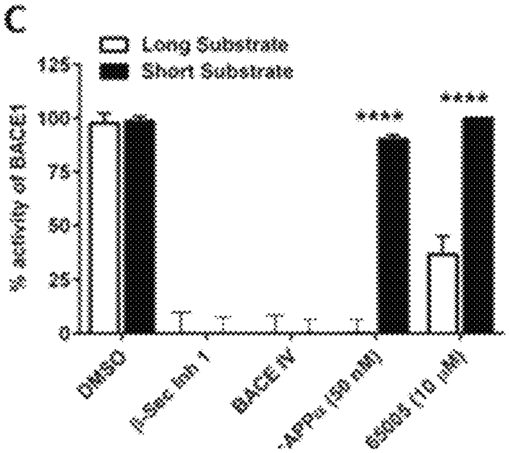
Figure 7:
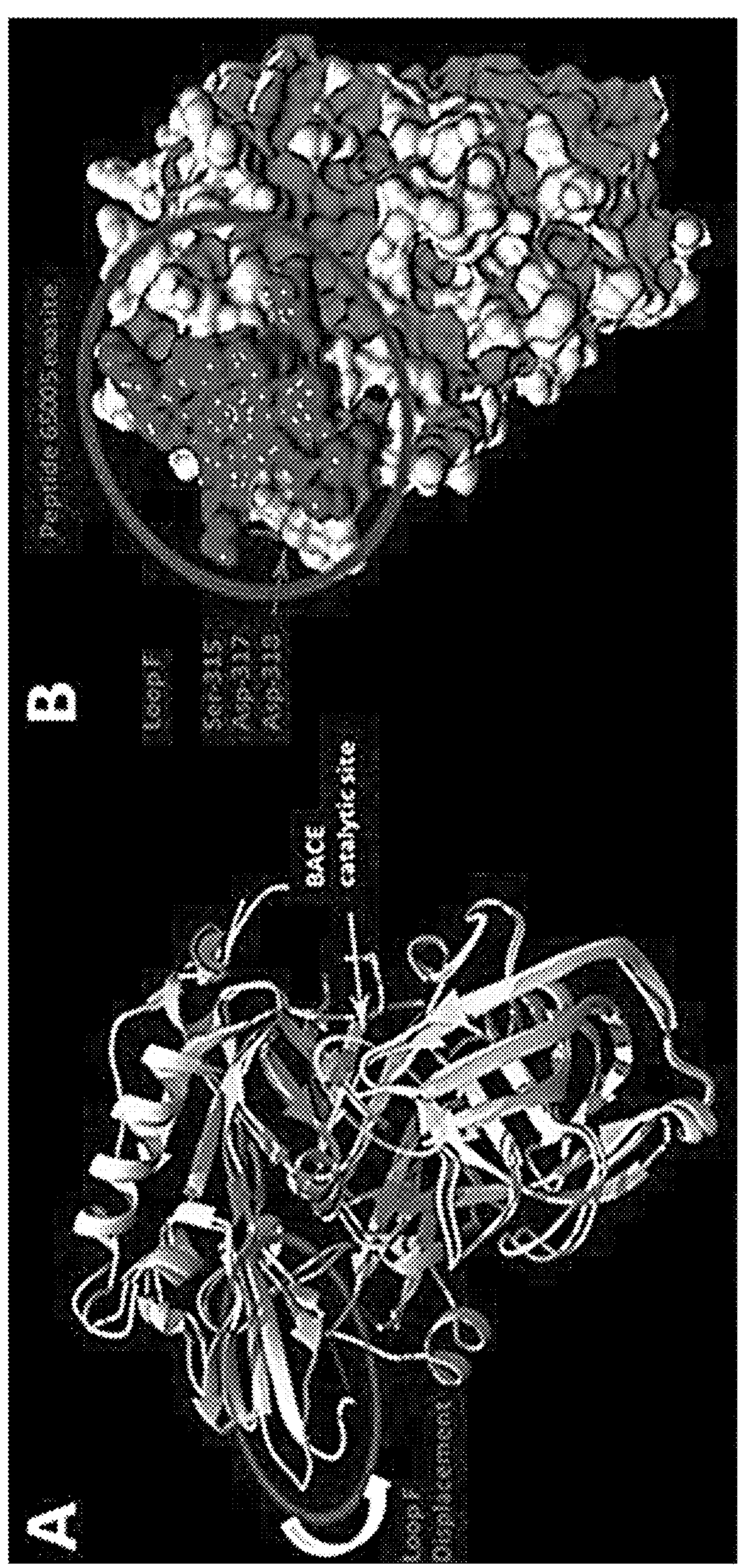
FIGS. 7A & B show that that Pep 65005 binding to an exosite and interacts with loop F on BACE.
FIG. 7B shows that the loop F is within the area of Pep 65005 interaction with BACE described by Kornacker.

The following studies illustrate the discovery of the novel allosteric BACE inhibitors described herein. First it was demonstrated that loop F-interacting Peptide 65005 inhibits long substrate cleavage by BACE. Peptide 1-11 was synthesized and it was shown that it, like sAPPα, preferentially inhibits BACE cleavage of the long MBP-APPC125, but not the short P5-P5', substrate, generating an allosteric inhibition profile (FIGS. 6, panels A, B, and C, respectively). Utilizing modeling and reported predicted sites of Pep 65005 interaction with BACE, it was shown that it interacts with an exosite that includes the Loop F region of BACE (FIG. 7). Molecular simulation studies using Amber16 software showed that peptide 65005 interacts at that site close to and above Loop F (FIG. 7, panel B) and alters the position of Loop F (see Example 1), thus inducing allosteric inhibition of BACE by a mechanism similar to that of the Genentech Ab.

Figure 8:
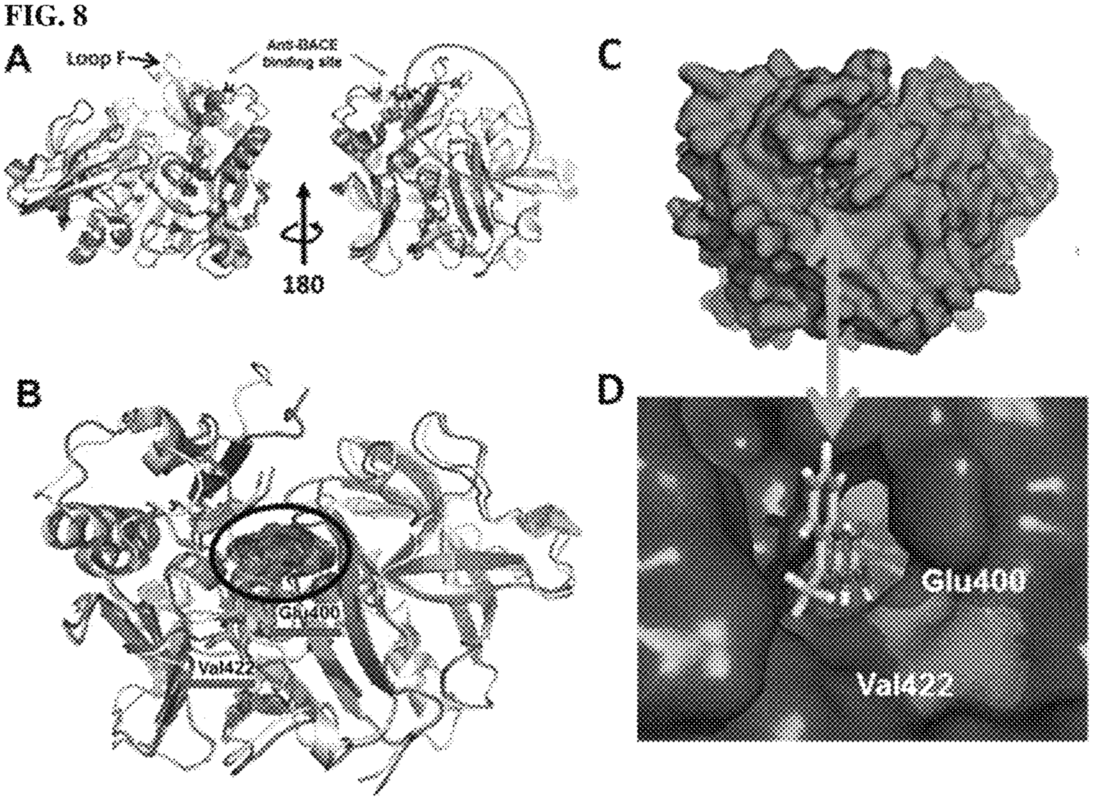
FIGS. 8A-D show that structure-based of BACE exosite that is different from the peptide 650005 exosite.

Using DDG prediction, a new BACE allosteric exosite was identified. In particular, by analysis of the energy difference after in silico alanine mutation in the protein backbone of BACE by Rosetta (DDG prediction), it was discovered a new exosite on BACE. For these experiments, the BACE crystal structures for either direct inhibitor (pdb: 1×N3) or allosteric inhibitor antibody binding (pdb: 3R1G)—where there is a distinct conformational difference between the two structures at the P5-P7 binding site bordered by Loop F (FIG. 8, panel A, two views shown)—were used. The DDG prediction was based on the difference in Rosetta energy between the wild-type structure and the mutated structure after full side chain optimization and a small degree of backbone optimization. Out of all 387 residues, sixteen residues in the protein backbone appear to stabilize BACE structure when bound to an anti-BACE antibody (3R1G, ΔΔG energy score lower than −2) and destabilize the BACE structure when bound to a long inhibitor (1×N3, ΔΔG energy score higher than 0.5). These sixteen residues (FIG. 8, panel B) are all located at protein surfaces. Interestingly, the surface representation of BACE binding to an anti-BACE antibody (pdb code:3R1G) reveals a large and deep pocket (FIG. 8, panel C), the DDG prediction reveals that this putative allosteric site is associated with two of the sixteen residues—Val422 and Glu400. The two crystallographic water molecules in the pocket are shown as yellow spheres (red arrow, FIG. 8, panel C). Residues Glu400 and Val422 cluster in three dimensional space and are associated with the putative allosteric site (FIG. 8, panel B, circled and 8, panel D). This new exosite reveals a binding pocket and is distinct from the peptide 65005 site described by Kornacker et al., and Gutierrez et al, shown in FIG. 7 that lies above Loop F. While the new exosite does not directly border Loop F, based on the ΔΔG prediction interaction with this exosite would cause displacement of Loop F like the Genentech Ab.

Utilizing computational docking, an initial round of in silico screening of a clinical compound database was performed and it was found molecules that docked to the putative allosteric site. Metformin analogs with good binding to the new exosite have been identified. These analogs display a significant allosteric inhibition profile (FIG. 9, panel A) in the cell-free enzyme assay system, providing validation for binding to the new exosite and initial in silico screening.

Active Agents—Allosteric BACE Inhibitors.

In various embodiments metformin analogs were identified that show good binding to the newly discovered exosite. Moreover, as noted above, these analogs display a significant allosteric inhibition profile (FIG. 9, panel A) in the cell-free enzyme assay system, providing validation for binding to the new exosite.

The active agents described herein comprise small molecule lead candidates that reduce sAPPβ, βCTF, and Aβ production through allosteric inhibition of BACE. The goal of the proposal is to identify an enzyme- and substrate-selective orally bioavailable, brain-penetrant allosteric inhibitor of BACE for preclinical testing as a novel pharmacotherapy to treat patients with MCI and AD.

Figure 11:
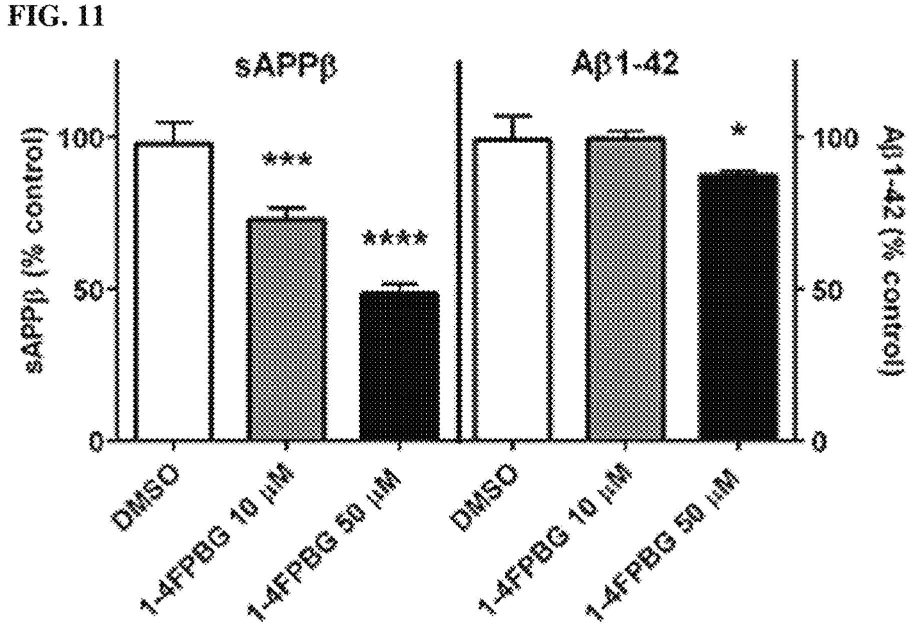
FIG. 11 shows that 1-4-FPBG decreases sAPPβ and Aβ in vitro. 1-(4-fluorophenyl)biguanidine (4-FPBG) significantly decreased sAPPβ from CHO-7W cells treated for 24 hours at 10 and 50 μM. Aβ1-42 was significantly decreased at 50 μM.

In a preliminary in-cell target engagement study for small molecule allosteric BACE inhibitor 1-(4-fluorophenyl) biguanidine (4-FPBG), one of the potential allosteric inhibitors identified from the screen that exhibited a good allosteric profile, 1-(4-fluorophenyl) biguanidine (4-FPBG), was tested at both 10 and 50 μM for 24 hours in Chinese hamster ovary cells that stably express human wild type APP (CHO-7W). 4-FPBG significantly decreased sAPPβ at both concentrations, and Aβ1-42 at 50 μM (FIG. 11). The results indicate that 4-FPBG is indeed a BACE inhibitor.

Figure 12:
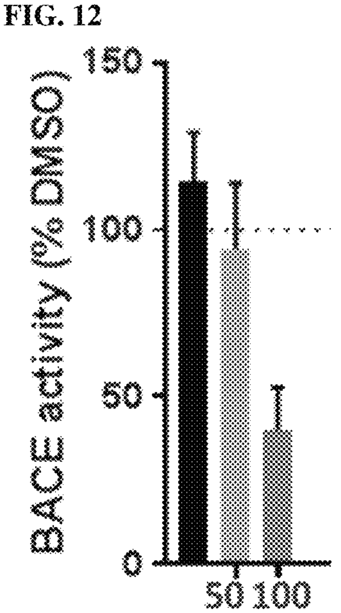
FIG. 12 illustrates the BACE activity in an MBPC125 Assay for JD009 at 50 and 100 uM (see, FIG. 10).
Figure 13:
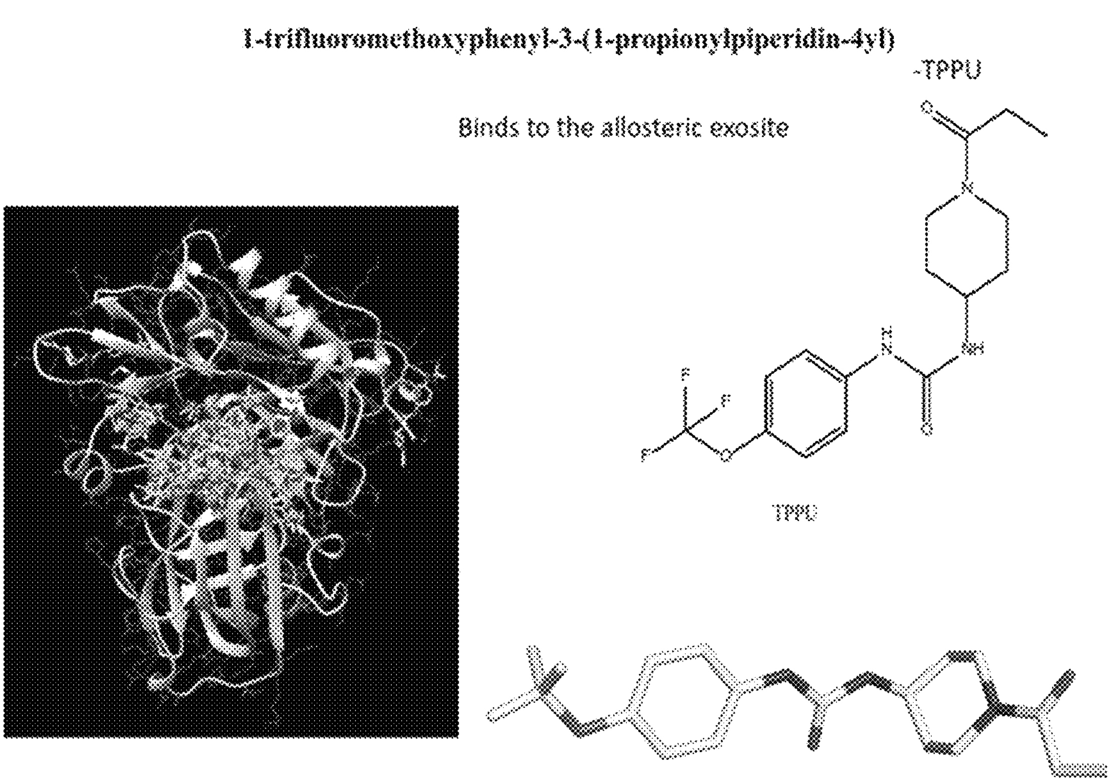
FIG. 13 illustrates the structure of 1-trifluoromethoxy-phenyl-3-(1-propionylpiperidin-4yl) (TPPU) and the binding of this molecule to the exosite binding site.

Similarly, the data shown in FIG. 12 show that JD009 (see, FIG. 10) has allosteric BACE inhibitory activity.

In one aspect, the present disclosure provides an allosteric BACE inhibitor said inhibitor comprising a compound according to the formula:

I

II

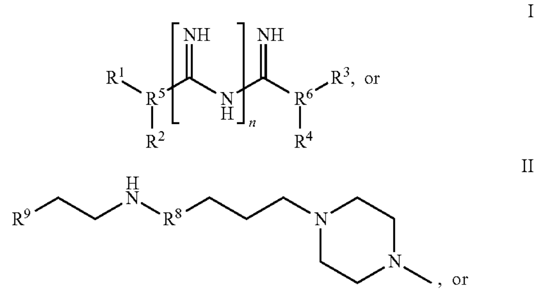

, or

, or

-continued

III

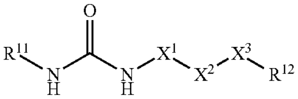

wherein:

$X^1$ is $CH_2$ or C(O);

$X^2$ is $CH_2$ or $CHR^{13}$;

$X^3$ is $CH_2$, O, or S;

$R^{11}$ is heterocyclyl;

$R^{12}$ is heteroaryl or heterocyclyl;

$R^{13}$ is alkyl or aralkyl;

n is 1, 2, or 3;

$R^5$ is CH or N;

$R^6$ is CH or N;

$R^1$ and $R^2$ are independently selected from H, Me, OMe, Pr, and substituted or unsubstituted phenyl; or $R^5$ taken with $R^1$ and $R^2$ is a substituted or unsubstituted homocycle or a substituted or unsubstituted heterocycle;

$R^3$ and $R^4$ are independently selected from H, Me, OMe, Pr, and substituted or unsubstituted phenyl; or N taken with $R^1$ and $R^2$ is a substituted or unsubstituted heterocycle;

$R^8$ is $CH_2$, C=O, or $SO_2$; and $R^9$ is selected from a substituted or unsubstituted indole, a substituted or unsubstituted phenyl, a substituted or unsubstituted carbazole, and

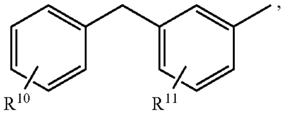

where $R^{10}$ and $R^{11}$ are independently H or halogen;

or a pharmaceutically acceptable salt, ester, amide, tautomer, or prodrug thereof; and wherein said compound is not metformin or proguanil.

In certain embodiments an allosteric BACE inhibitor is provided where the inhibitor comprises a compound according to Formula I:

I

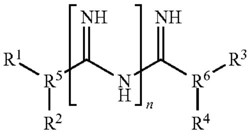

wherein n is 1, 2, or 3; $R^5$ is C or N; $R^6$ is C or N;

$R^1$ and $R^2$ are independently selected from H, Me, OMe, Pr, and substituted or unsubstituted phenyl; or $R^5$ taken with $R^1$ and $R^2$ is a substituted or unsubstituted homocycle or a substituted or unsubstituted heterocycle;

$R^3$ and $R^4$ are independently selected from H, Me, OMe, Pr, and substituted or unsubstituted phenyl; or N taken with $R^1$ and $R^2$ is a substituted or unsubstituted heterocycle;

or according to Formula II:

II

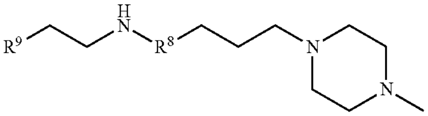

where $R^8$ is $CH_2$, C=O, or $SO_2$; and $R^9$ is selected from a substituted or unsubstituted indole, a substituted or unsubstituted phenyl, a substituted or unsubstituted carbazole, and

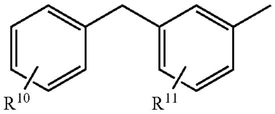

where $R^{10}$ and $R^{11}$ are independently H or halogen;

or a pharmaceutically acceptable salt, ester, amide, tautomer, or prodrug thereof; and wherein said compound is not metformin or proguanil, or TPPU.

In certain embodiments the compound is a compound of Formula I and $R^1$ is Me. In certain embodiments the compound is a compound of formula I and $R^2$ is Me. In certain embodiments the compound is a compound of formula I and $R^2$ is Pr. In certain embodiments the compound is a compound of formula I and $R^2$ is OMe. In certain embodiments the compound is a compound of formula I and $R^2$ is H. In certain embodiments the compound is a compound of Formula I and $R^1$ is H. In certain embodiments $R^2$ is H, or $R^2$ is phenyl. In certain embodiments $R^2$ is substituted phenyl (e.g., a halogen substituted phenyl). In certain embodiments $R^2$ is selected from

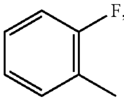

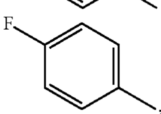

, and

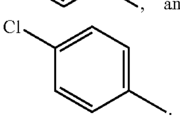

In certain embodiments $R^5$ is C, while in other embodiments $R^5$ is N. In certain embodiments the compound is a compound of Formula I and $R^5$ taken with $R^1$ and $R^2$ is a substituted or unsubstituted homocycle or a substituted or unsubstituted heterocycle. In certain embodiments $R^5$ taken with $R^1$ and $R^2$ is an unsubstituted phenyl or a substituted phenyl. In certain embodiments $R^5$ taken with $R^1$ and $R^2$ is an unsubstituted phenyl. In certain embodiments $R^5$ taken with $R^1$ and $R^2$ is an aryl or a heteroaryl. In certain embodiments $R^5$ taken with $R^1$ and $R^2$ is selected from a pyrrolidine, an oxazole, a piperidine, or an oxazine. In certain embodiments $R^5$ taken with $R^1$ and $R^2$ is selected from

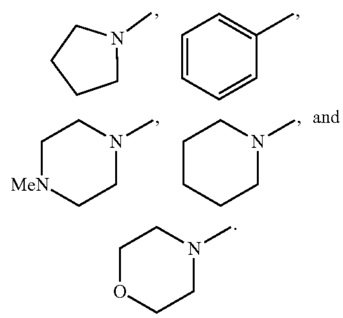

In certain embodiments n is 1, in other embodiments, n is 2, and in other embodiments n is 3. In certain embodiments the compound is a compound of Formula I and $R^3$ is H. In certain embodiments the compound is a compound of Formula I and $R^3$ is Me. The compound is a compound of Formula I and $R^3$ is OMe. In certain embodiments the compound is a compound of Formula I and $R^3$ is Pr. In certain embodiments the compound is a compound of Formula I and $R^3$ is phenyl. In certain embodiments of the foregoing embodiments $R^4$ is H. In certain embodiments of the foregoing embodiments $R^4$ is Me. In certain embodiments of the foregoing embodiments $R^4$ is OMe. In certain embodiments of the foregoing embodiments $R^4$ is Pr. In certain embodiments $R^6$ is C, while in other embodiments $R^6$ is N.

In certain embodiments the compound is a compound of Formula I and $R^6$ taken with $R^3$ and $R^4$ is a substituted or unsubstituted homocycle or a substituted or unsubstituted heterocycle. In certain embodiments $R^6$ taken with $R^3$ and $R^4$ is an unsubstituted phenyl or a substituted phenyl. In certain embodiments $R^6$ taken with $R^3$ and $R^4$ is an unsubstituted phenyl. In certain embodiments $R^6$ taken with $R^3$ and $R^4$ is an aryl or a heteroaryl. In certain embodiments $R^6$ taken with $R^3$ and $R^4$ is selected from a pyrrolidine, an oxazole, a piperidine, or an oxazine. In certain embodiments $R^6$ taken with $R^3$ and $R^4$ is selected from

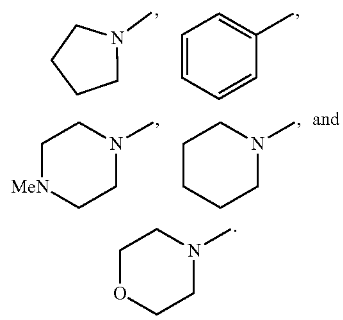

In certain embodiments the allosteric BACE inhibitor comprises a compound is selected from:

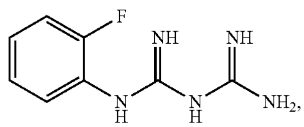

-continued

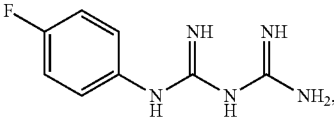

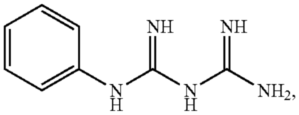

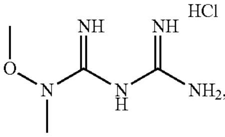

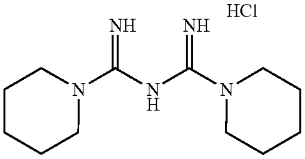

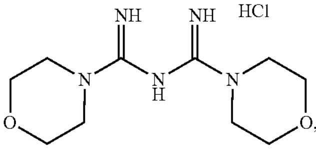

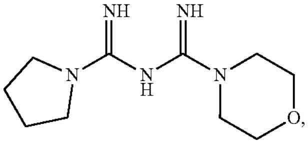

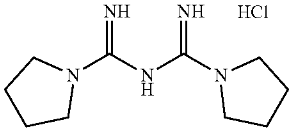

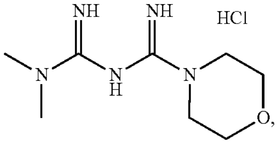

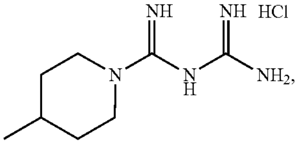

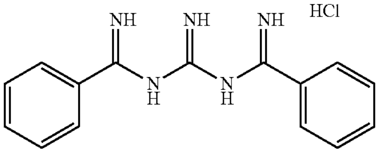

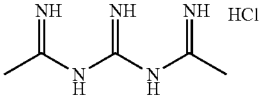

,

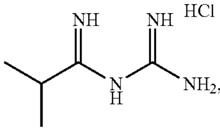

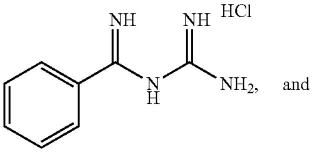

and

-continued

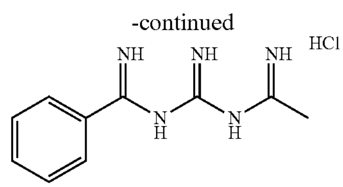

In certain embodiments the compound is a compound of Formula II and $R^8$ is $CH_2$. In certain embodiments the compound is a compound of Formula II and $R^8$ is C═O. In certain embodiments the compound is a compound of Formula II and $R^8$ is $SO_2$. In certain embodiments the compound is a compound of Formula II and $R^9$ is selected from

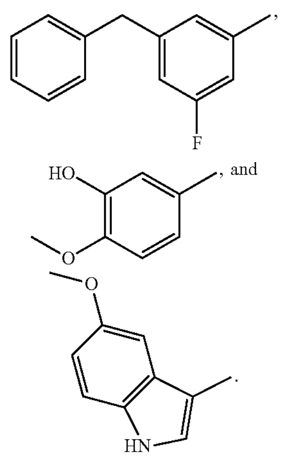

and

In certain embodiments the allosteric BACE inhibitor is selected from

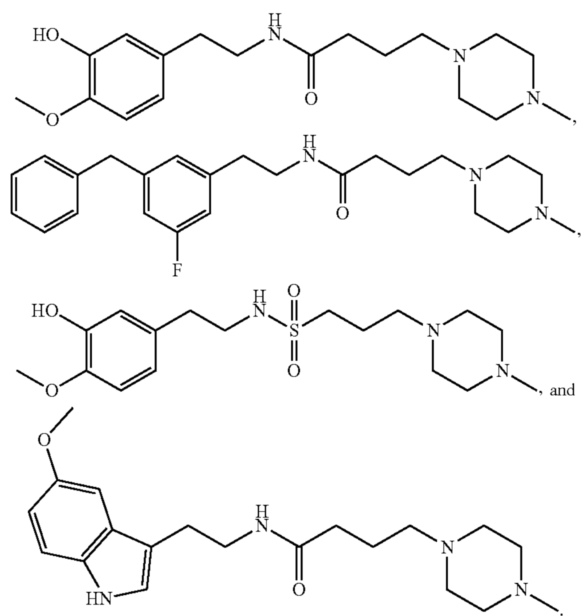

and

In certain embodiments the allosteric BACE inhibitor is compound of formula III:

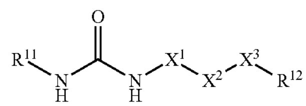

or a pharmaceutically acceptable salt thereof.

In certain embodiments, $R^{11}$ is piperidinyl. In certain embodiments, a nitrogen of the heterocyclyl (e.g., piperidine) is substituted with alkyl or acyl (e.g., ethylacyl). In certain embodiments, a carbon of the heterocyclyl (e.g., piperidine) is substituted with heteroarylalkyl (e.g., imidazolylethyl).

In certain embodiments, $X^1$ is $CH_2$. In other embodiments, $X^1$ is C(O).

In certain embodiments, $X^2$ is $CH_2$. In other embodiments, $X^2$ is $CHR^{13}$ and $R^{13}$ is aralkyl (e.g., benzyl or homobenzyl). In certain embodiments, the aryl is substituted with amino (e.g., methylamino).

In certain embodiments, $X^3$ is $CH_2$. In other embodiments, $X^3$ is S.

In certain embodiments, $R^{12}$ is heterocyclyl (e.g., piperazinyl). In certain embodiments, a nitrogen of the heterocyclyl (e.g., piperazine) is substituted with hydroxyalkyl (e.g., hydroxyethyl). In other embodiments, $R^{12}$ is heteroaryl (e.g., imidazolyl). In certain embodiments, the heteroaryl (e.g., imidazole) is substituted with hydroxyalkyl (e.g., hydroxyethyl).

In certain embodiments, the allosteric BACE inhibitor is

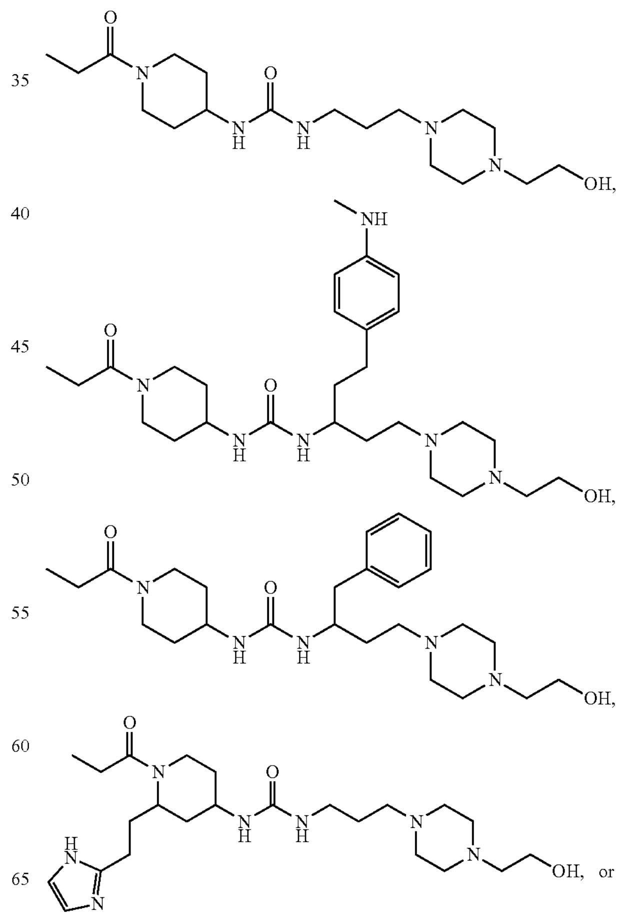

or

-continued

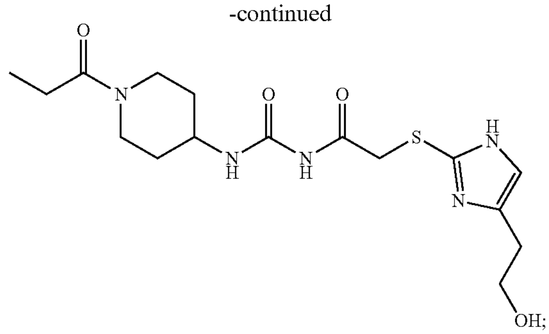

or a pharmaceutically acceptable salt thereof.

Figure 9:
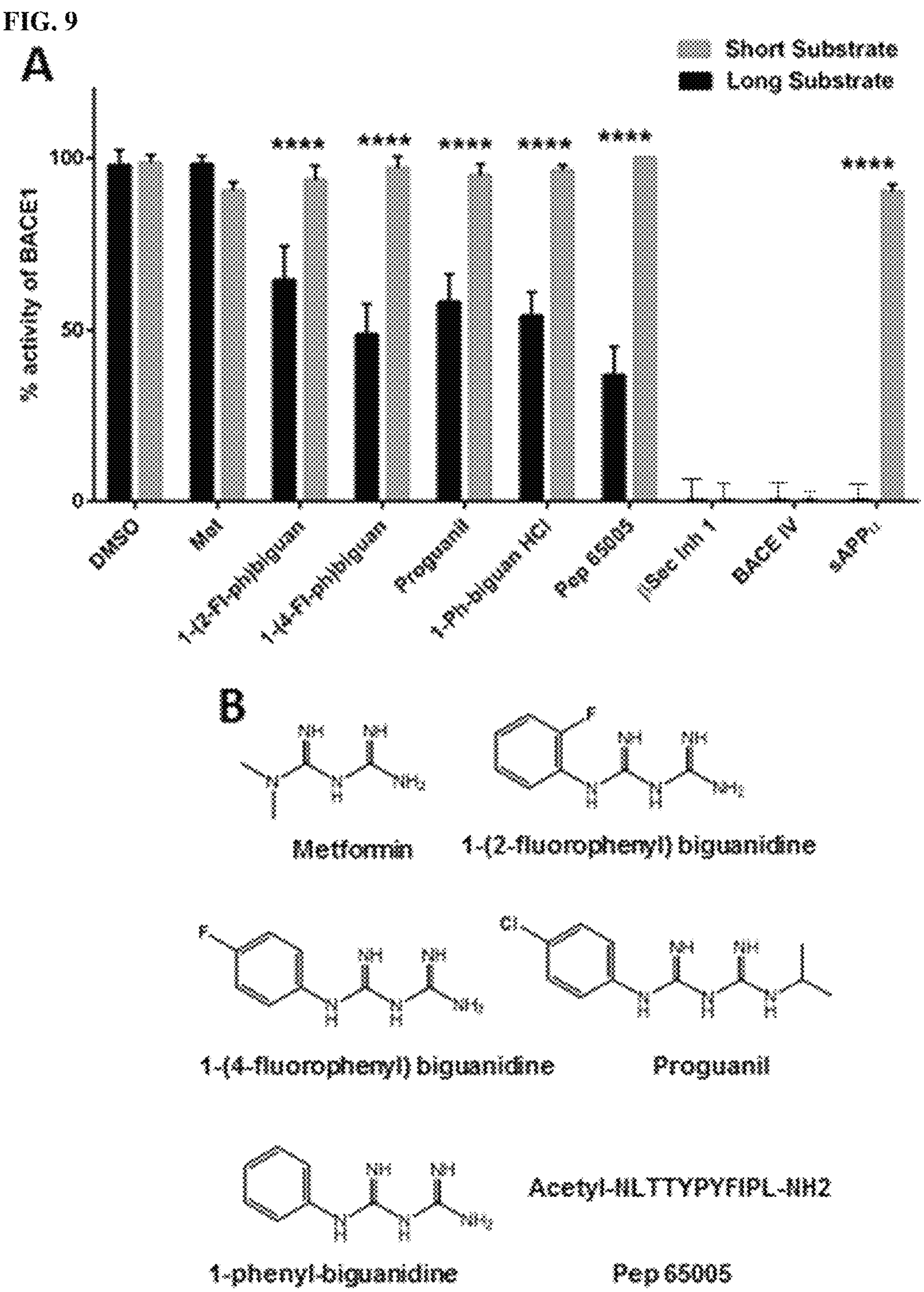
FIG. 9A shows metformin analogs with an allosteric BACE inhibitor profile. Pep 65005 and 5 metformin analogs show a BACE inhibitory profile, inhibiting BACE activity in the long, but not short substrate. Met: metformin; 1-(2-Fl-ph) biguan: 1-(2-fluorophenyl) biguanidine; 1-(4-Fl-ph) biguan: 1-(4-fluorophenyl)biguanidine; 1-Ph-biguanidine HCl: 1-phenyl-biguanidine HCl; βSec Inh 1: β secretase inhibitor 1.
FIG. 9B shows the structures of certain metformin analogs.
Figure 10:
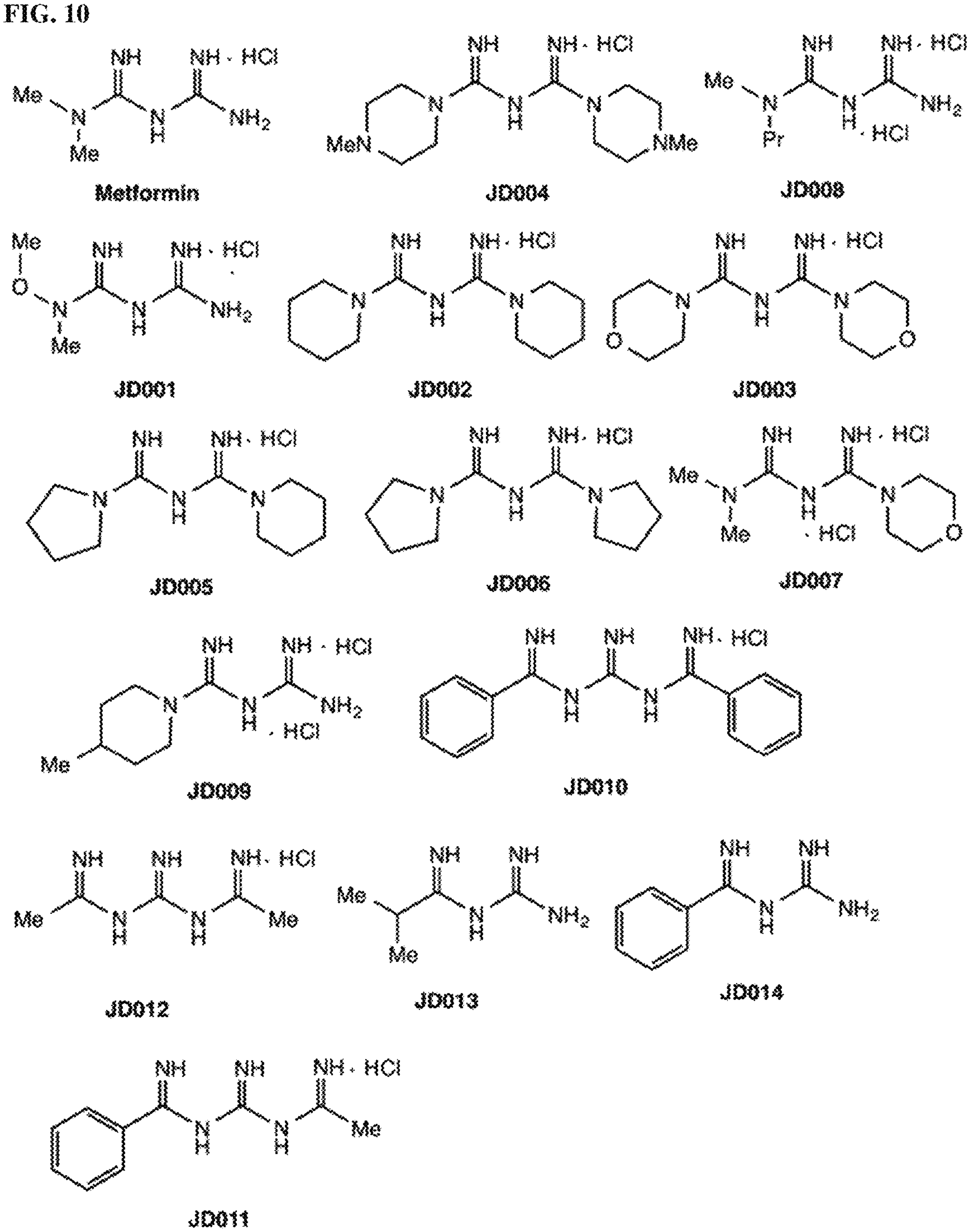
FIG. 10 illustrates analogs of metformin that have been synthesized. JD009 has consistently demonstrated to be active in an allosteric BACE assay. Other molecules such as BJ-58, 63,66 and 70 show good binding to a BACE exosite in in silico analysis.
Figure 10:
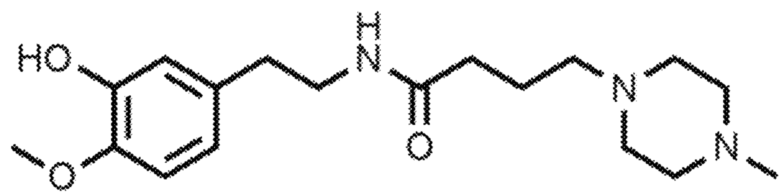
Figure 10:
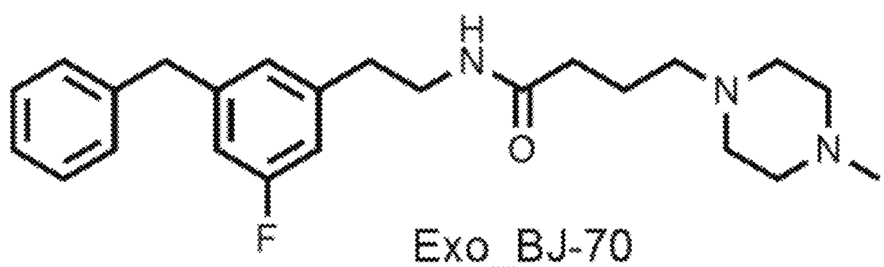
Figure 10:
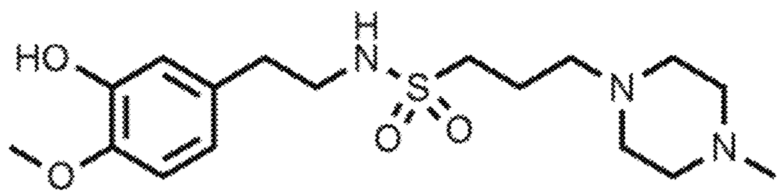
Figure 10:
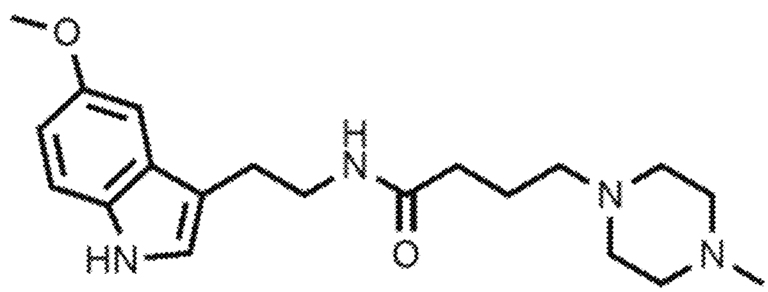

Illustrative, but non-limiting examples of suitable active agents (allosteric inhibitors of BACE) are shown in FIGS. 9 and 10.

In certain embodiments the allosteric BACE inhibitor comprises metformin and/or proguanil, and/or TPPU.

Figure 15:
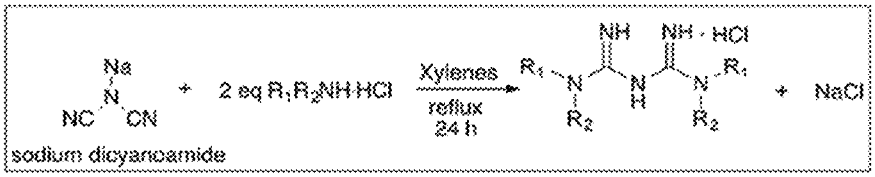
FIG. 15 illustrates various schemes for the synthesis of the metformin analogs. Scheme 1: Synthesis of symmetrical metformin analogs. Scheme 2: Synthesis of unsymmetrical metformin analogs. Scheme 3: Synthesis of unsubstituted analogs. Scheme 4: synthesis of alkyl and aryl analogs.
Figure 15:
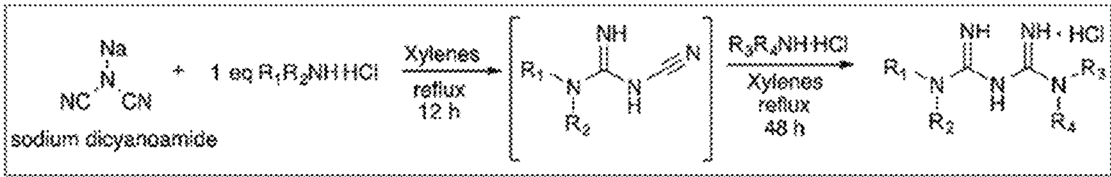
Figure 15:
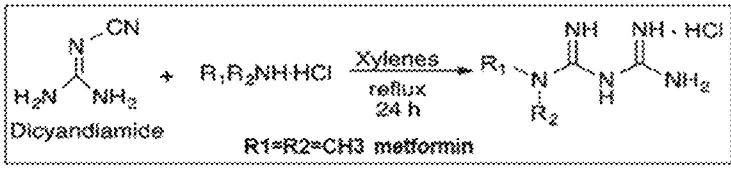
Figure 15:
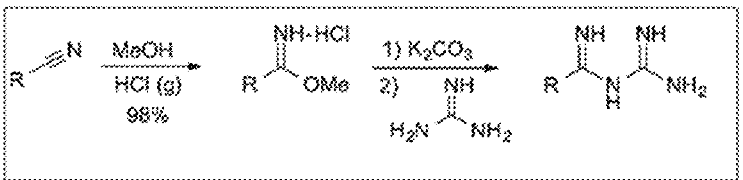
Figure 16:
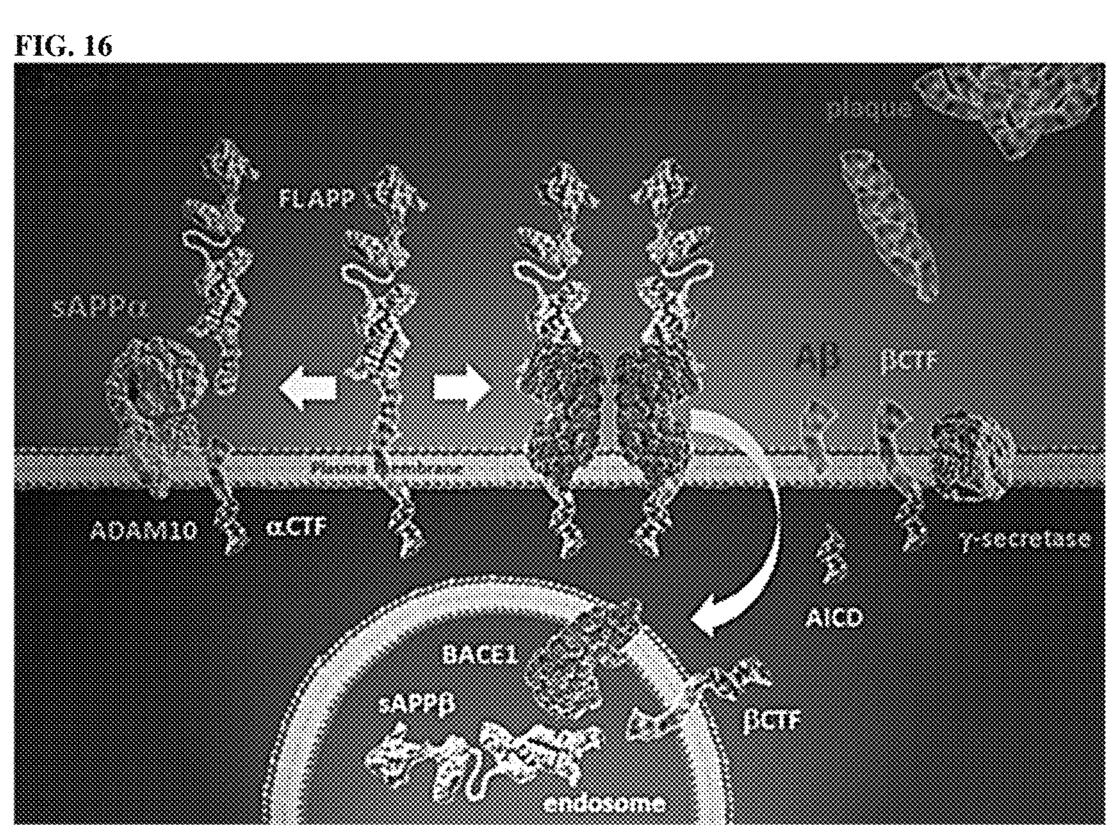
FIG. 16, shows that APP may be cleaved by ADAM10 to generate neurotrophic fragments sAPPα and αCTF or, alternatively, by BACE. In BACE cleavage, dimers of BACE and APP complex are endocytosed to a relatively acidic endocytic compartment wherein APP is cleaved generating sAPPβ and βCTF. The latter is then cleaved by γ-secretase to form amyloid-β—which can form oligomers, aggregates, fibrils, and ultimately plaques—and the APP intracellular domain (AICD).

Methods of synthesizing the allosteric inhibitors described herein are known to those of skill in the art. Additionally, synthesis schemes for various metformin analogs are shown in FIG. 15. In particular, Scheme 1 illustrates the synthesis of symmetrical metformin analogs. Scheme 2 illustrates the synthesis of unsymmetrical metformin analogs. Scheme 3 illustrates the synthesis of unsubstituted analogs. Scheme 4 illustrates the synthesis of alkyl and aryl analogs.

The foregoing allosteric BACE inhibitors are illustrative and non-limiting. Using the teachings provided herein, numerous other allosteric BACE inhibitors will be available to those of skill in the art.

The preliminary data shown herein indicate the feasibility of discovering a small molecule allosteric inhibitor of BACE. Through modeling studies, a new exosite on BACE that can interact and potentially displace Loop F has been identified. Furthermore, an initial round of in silico screening using this exosite led to the identification of a series of metformin analogs that had good binding to the exosite. These 'hits' were confirmed to be allosteric BACE inhibitors in the cell-free assay and as BACE inhibitors in CHO-7W cells.

Validation and Optimization of Allosteric Inhibitors.

Hit-to-lead optimization can lead to the identification of brain penetrant allosteric BACE inhibitors. The assays and methods described herein to elucidate the metformin analog BACE inhibitory effects are well-established during the course of the previous studies showing BACE inhibition by sAPPα (see, Example 1) and can be adapted to an HTS program to screen for additional small molecule allosteric BACE inhibitors. Hits identified in HTS can be validated in secondary and tertiary assays. The best 'hits' are subject to hit-to-lead optimization and iterative structure-based design using co-crystal/soaking structures with BACE. In addition, exosite docking analysis of new hits from HTS can be used to prioritize their selection for secondary analysis. Taken together, the data provides strong support for the screening approach. The preliminary data supports the goals to obtain potent, brain-penetrant, and safe allosteric BACE inhibitors for proof-of-concept testing in AD models as described herein. It is believed this work has led to a new class of pre-clinical candidates for therapeutic development in MCI/AD.

The recent finding that sAPPβ is a potent endogenous inhibitor of BACE that exerts this effect by an allosteric mechanism provided the basis for a new pharmacotherapeutic approach to identify new candidates for MCI and/or AD as described herein. It has been established the assays and other methods such as in silico screening, SPR, co-crystallization, and Top-down MS analysis to characterize such small molecule allosteric BACE inhibitors. The data presented herein demonstrate the feasibility of discovering small molecule allosteric BACE inhibitors. Specifically, it is believed that: a) HTS can be to identify additional BACE inhibitors using a primary AlphaLISA-based MBP-APPC125 assay (see, e.g., FIG. 1) to detect the CTF fragment generated by BACE cleavage of the substrate as well as conduct in silico screening to identify small molecules for primary (MBP-C125 substrate) and secondary assay (P5-P5' substrate) screening to identify allosteric inhibitors; conduct validation of hits in the cell models for effects on sAPPβ, sAPPα, and Aβ1-40/42; use in silico analysis to prioritize 'hits' that bind to the new exosite; b) Medicinal chemistry hit-to-lead optimization starting with the metformin analog 'hits' described herein can be used to identify lead candidates with good brain penetrance and ADME-T profiles; c) Mechanistic studies of leads in SPR or ITC analysis can utilize top-down MS, and co-crystallization/soaking studies to characterize sites of interaction of inhibitors with BACE; and d) Proof-of-concept evaluations of the best candidates in in vivo AD models can readily be performed. Lead candidates can be identified for dose-ranging efficacy and non-GLP toxicity testing.

Identification of Validated 'Hits' Through Screening for Allosteric BACE Inhibitors and In Silico Analysis for Virtual Screening for Allosteric BACE Inhibitors and Support of Hit Validation.

A chemical library was screened using the primary BACE inhibition AlphaLISA assay with the MBP-APPC125 substrate to obtain (e.g., about 200) hits that repeat after cherry-picking. These hits can undergo secondary screening in the P5-P5' BACE cleavage assay and those that do not inhibit cleavage would thus be potential allosteric BACE inhibitors. These putative allosteric inhibitors are validated in CHO-7W, human SH-SY5Y neuroblastoma cells stably transfected with human wtAPP. These cells would be treated for 24 hours at 1 μM and then both cells and media collected for analysis of sAPPα, sAPPβ, Aβ1-40, and Aβ1-42 by AlphaLISA and CTF by ELISA. Further in silico exosite-docking analysis can be performed for prioritization of 'hits'.

As shown in FIGS. 6 and 9, cell-free assays can be used to identify potential allosteric BACE inhibitors.

Primary Allosteric Inhibitor Screening HTS Assay.

A primary assay that is HTS formatable in 384 plates was developed. The assay uses recombinant BACE expressed and purified by the method of Sussman et al in the UCLA protein production core; alternately BACE can be purchased from R&D Systems (931-AS-050). MBP-APPC125—a fusion protein of maltose-binding protein and the last 125 C-terminal residues of APP695 wild type—has already been expressed and purified in the core. The AlphaLISA signal is detected using the PE Enspire instrument. Hit confirmation can be done by cherry-picking and purchase of commercially available compounds. The primary HTS assay can be optimized as desired. The screening optimization strategy can include miniaturization of the assay to 384-well plate, linearity, CVs for HTS assay run in triplicate, and Z-values (Z>0.6). The compound libraries consist of over 200,000 compounds that are split into 4 segments: pharmacological validation and repurposing libraries (Biomol, Prestwick and Microsource spectrum and NIH clinical collection), targeted libraries, lead-like libraries, diverse libraries (UCLA) and diverse sets of smart libraries (see resource section). All of the compounds are at least 90% pure, typically better. With the exception of the diverse library, which is a pre-plated set, all of the sets are custom sets and are not likely to be found in another screening facility. Extensive filtering against liabilities such as reactive groups, aggregators, etc. was applied.

Secondary, Short Substrate Assay for Allosteric Inhibitor Identification.

Hits from the primary screen that give a dose-response can be re-evaluated in a BACE assay utilizing a commercially available fluorogenic P5-P5' peptide substrate (R&D Systems ES004) to determine selectivity for inhibition of cleavage of the long, but not the short, BACE substrate. In this protocol, BACE stock at 200 μg/mL is thawed on ice and diluted in BACE assay buffer to a BACE working concentration of 7.5 ng/μL. Small molecule stock solutions at 10 mM in DMSO are serially diluted at concentrations along an 11 point two-fold dilution series starting at 50 μM. The substrate is diluted in BACE assay buffer to a concentration of 50 μM and kept protected from light, then, 4 μL of assay buffer are loaded to each well, followed by 2 μL of BACE diluted in assay buffer to 7.5 ng/μL. Following this, 2 μL of compound stock are added to appropriate wells and incubated for 30 minutes at room temperature, followed by addition of 2 μL of fluorogenic short substrate diluted to 50 μM in assay buffer to each well. The fluorescence is read immediately in a SpectraMax M2 fluorescence reader from Molecular Devices set at an excitation wavelength of 320 nm and emission wavelength at 405 nm every 30 min for 2 h.

Validation of 'Hits' in Dose Response.

Figure 14:
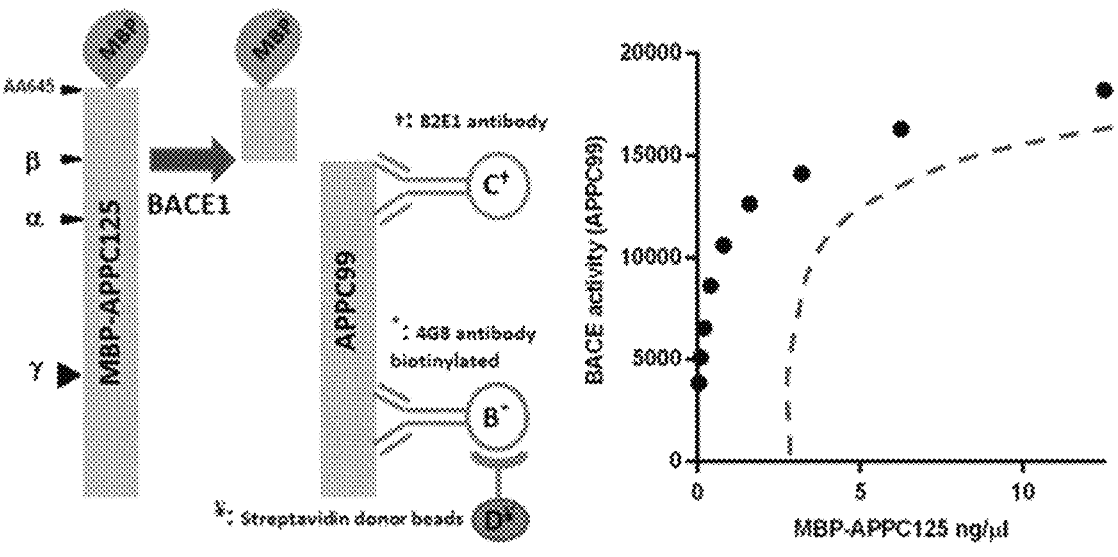
FIG. 14 decpits an HTS AlphaLISA MBP-APPC125 BACE cleavage assay. (Left) The readily HTS-formatable AlphaLISA uses capture beads (C) and biotinylated-antibody beads (B) that interact with streptavidin donor beads (D) resulting in the emittance of light quantified using a plate reader. (Right) Increasing amounts of BACE-cleaved substrate leads to the formation of b-CTF that are accurately quantified by the assay.

BACE stock at 200 μg/mL is thawed on ice and diluted in BACE assay buffer to a working concentration of 7.5 ng/μL. MBP-APPC125 stock solution at 0.1 mg/mL is diluted in water to a working concentration of 12.5 ng/μL. Small molecule stock solution at 10 mM in DMSO are serially diluted at concentrations along an 11 point two-fold dilution series starting at 50 μM. The AlphaLISA assay is composed of an antibody mix and a donor mix. The antibody mix has anti-Aβ acceptor beads (Cat #AL275) having the 82E1 antibody specific for Aβ N-terminus and anti-Aβ from the AL202 kit (Cat #AL202AC) having the 4G8 antibody biotinylated (see FIG. 14). The donor mix has the streptavidin-coated donor beads. Perkin Elmer standard protocol is followed to prepare the mix. In this assay, 2 μL of BACE are added to each well, then, 2 μL of inhibitor (or library compound) are loaded to into the wells and incubated for 30 minutes at room temperature. After incubation, 2 μL of the MBP-APPC125 are added to each well and incubated for another 2 hours at room temperature. The cleavage of MBP-APPC125 is assessed per AlphaLISA protocol in which 2 μL acceptor and biotinylated antibodies are added to each well, incubated for 1 hour at room temperature, the 2 μL of donor beads added to each well and incubated for 30 minutes at room temperature.

Modeling Studies for Allosteric Inhibitors.

The 'hits' from the screening can also be subject to in silico docking with the BACE exosite that has been discovered to obtain binding scores for prioritization. An initial virtual screening run of the compound library to identify molecules that bind to the putative allosteric site was performed and it identified several metformin analogs that are allosteric BACE inhibitors at 10 μM. These analogs, along with new validated hits from HTS, can be prioritized by in silico analysis based on binding. The best analogs from these studies would enter the flow scheme for further development in exploratory medicinal chemistry and for 'hit-to-lead' optimization in an iterative fashion. Molecular simulation studies using AMBER16 software package for promising candidates can also be performed.

Tertiary Cell Assays in huAPPwt Stably-Transfected Cells.

Using CHO-7W and human neuroblastoma SH-SY5Y cells stably transfected with human APP wildtype, it is possible to determine the capability of these molecules for BACE inhibition. The first assay would be in CHO-7W cells, similar to 4-FPBG (see, e.g., data, FIG. 11), where it is possible to look for inhibition of sAPPβ and Aβ along with effects on sAPPα. The best 'hits' can then be evaluated in the human SH-SY5Y cells stably transfected with human wtAPP. The biomarkers sAPPα and sAPPβ secreted into the cellular media can be measured using the AlphaLISA assay (PerkinElmer). Aβ 1-40 and 1-42 can be determined in both media and cell lysates. In the SH-SY5Y cells effect of 'hits' on βCTF, total tau and ptau can also be determined in cell lysates using an ELISA. The standards, blanks, and media would be diluted with the buffer provided in the kit and added to the plate. During the first incubation step, the analyte is captured either by an antibody recognizing the α-secretase cleavage site at sAPPα C-terminus (clone 2B3) or the sAPPβ C-terminus, and then by a second biotin-labeled antibody specific to the N-terminal common domain of sAPP. In the second incubation step, the biotinylated anti-analyte antibody is bound to the streptavidin-coated donor beads. At the end of this reaction, the plates are read on an EnSpire Alpha 2390 multilabel plate reader equipped with the AlphaScreen module. For Aβ1-40 and 1-42 (with AlphaLISA kits AL275C and AL276C, respectively), Aβ would be quantified from a standard curve and normalized to total cellular protein. Total tau would be determined using AlphaLISA kit AL271C and ptau by using the tau kit but substituting A T8-biotin or Ser404-biotin for the biotinylated antibody beads. βCTF would be determined by ELISA following manufacturer's instructions.

Recombinant MBP-APPC125 and BACE for Studies.

MBP-APPC125 WT Substrate for the HTS Assay.

This substrate has already been produced using a protocol previously described in "Purification and cloning of amyloid precursor protein beta-secretase from human brain" *Nature* 402, 537-540 (1990). The purified MBP-APPC125 for the HTS assay and stored at ~2 mg/ml.

Recombinant BACE (rBACE) Production.

The rBACE production was done using the Sussman protocol described in "Flexibility of the flap in the active site of BACE1 as revealed by crystal structures and molecular dynamics simulations", *Acta crystallographica. Section D, Biological crystallography* 68, 13-25 (2012). The $His_6$-BACE1 expression construct in the pET24a vector encompasses human BACE1 (amino acids 43-454) with two mutations (K136A/E138A) that alter crystal packing under the control of the T7 promoter and with an N-terminus hexa-histidine tag. The vector confers kanamycin resistance. ON cultures of *E. coli* BL21 can be started by inoculation of media with colonies from the transformation plate; then the ON cultures are expanded to several 1 L flasks and grown in the presence of kanamycin at 37° C. with shaking (200-220 rpm) until OD600 reaches ~0.8-0.9. Throughout production and purification, aliquots are taken for SDS-PAGE analysis. The protein can be purified by a standard protocol as outlined in the Sussman publication. The protein can be refolded using the published protocol and enzyme activity can be determined. A small scale expression and purification has been performed and active BACE has been obtained.

Alternative Strategies.

In certain embodiments the primary screening assay could yield more than the desired number of hits, in which case the selection criteria can be adjusted to keep the hit rate at 0.2%. In certain embodiments about 200 validated hits are obtained after secondary and tertiary screens. Higher numbers can be triaged based on adjustment to the selection criteria and 'druggable' structures and in silico scores for binding to the exosite.

Optimization of Potency, Selectivity and Permeability Through an Exploratory Medicinal Chemistry Program to Discover Leads for In Vivo Validation.

Medicinal chemistry and SAR analysis can be used to increase potency of validated hits and to generate analogs such as shown in Schemes 1-4 (see, FIG. 15). Lead analogs achieved through synthetic modifications that meet potency (e.g., EC50<1 μM) and selectivity criteria receive further evaluation. In addition, the potential for brain penetrance can be ascertained in the parallel artificial membrane permeability assay (PAMPA) and in Caco-2 cells, the best candidates go on to in vivo pharmacokinetic (PK) analysis.

Optimization of Validated Hits.

Based on the identification of metformin analogs from the initial round of virtual screening, a hit-to-lead optimization effort is planned to be conducted. The goal is to identify allosteric BACE inhibitor analogs with an IC50<10 μM using strategies such as shown below (Schemes 1-4) for further evaluation in Aims 3 and 4. The overall goal of the SAR effort would be to develop novel, potent analogs of these hits that are allosteric BACE inhibitors with improved cell efficacy, physicochemical properties such as aqueous solubility, bioavailability, and increased brain penetrance. Iterative data can be used in the SAR effort to optimize lead candidates for further testing. The optimal analogs would exert the desired effects in the primary, secondary, tertiary, and permeability assays.

Design Strategies for Synthesis of Novel Metformin Analogs.

Synthetic schemes 1-4 (FIG. 15) can be used to generate symmetrical and unsymmetrical metformin analogs identified from the initial in silico screening. A number of such analogs that have been synthesized are illustrated in FIGS. 9 and 10. These analogs are tested in the primary, secondary, and tertiary assays. "Hits" from the HTS analysis that are validated can move into the hit-to-lead optimization effort that would comply with Lipinski's Rule of Five. Information from the mechanistic analyses, PAMPA/Caco-2 studies, SPR, Top down MS, and co-crystallization of promising candidates can be used in the design of more potent and orally brain penetrant analogs. Using these strategies a set of focused exploratory analogs can be generated to identify the structural features essential for enhancing potency and brain penetrance. New compounds can be synthesized by both standard batch chemistry and flow chemistry.

Medicinal Chemistry Strategy.

As part of the exploratory SAR studies synthesis can be performed using flow chemistry. In certain embodiments the potency of new analogs can be increased to achieve EC50s<1 μM for BACE inhibition as well as substrate- and enzyme-selectivity. Simultaneously the pharmacological profile of the leads can be addressed based on iterative data generated, e.g., as described above.

Testing of Analogs.

Analogs can be tested in the primary and secondary assays to identify active allosteric BACE inhibitors. The analogs can also be tested in the assays (tertiary assays) and in permeability assays. The data can be used to iteratively inform new analog synthesis.

b) Substrate and Enzyme Selectivity of Optimized Leads.

NRG1 Cleavage Assay.

A custom AlphaLISA can be used for determination of NRG1 cleavage by BACE. BACE stock is diluted in BACE assay buffer to a working concentration of 17 ng/μL and recombinant NRG1 (R &D Systems cat #396-HB/CF) diluted in water to a working concentration of 12.5 ng/μL. The detection kit has an anti-N-terminal NRG1 acceptor bead (SigmaAldrich SAB2101655) and biotinylated anti-C-terminal NRG1 (Abcam 191139) donor bead antibody mix. The donor mix has the streptavidin-coated donor beads. Perkin Elmer standard protocol is followed to prepare the mix. In this assay, 1 μL of NRG1 working solution is incubated with 2 μL of protein for 15 min and then 3 μl of BACE working solution is loaded into each well and incubated for 60 min at 37° C. Then, 2 μL of the antibody mix is loaded into each well and incubated for 1 h at room temperature. After this time, the donor mix is added into the wells and incubated for 30 min followed by signal detection using an PE Enspire instrument. A cell based assay would be used for PSGL1.

BACE2 and Cathepsin D (Cat-D) Assays.

To evaluate selectivity of optimized leads they can be tested in BACE2 and Cat-D protease assays. These are commercially available assays.

c) In Vitro Permeability Testing in PAMPA and Caco-2 Cells.

PAMPA.

Cell-free permeability can be evaluated in the parallel artificial membrane permeability assay (PAMPA) using immobilized artificial membranes and chromatography using the IAM column from Regis technology (www.registech.com) using a Agilent HPLC system. This assay is routinely performed and the data shows that compounds with $K_{IAMPerm}=K_{IAM/}{}^{4}>0.65$ have increased brain permeability, and compounds with $K_{IAMPerm}>1$ have high brain/plasma ratios.

Caco-2 Cells.

In certain embodiments, for the Caco-2 cell assay, monolayers are grown on filters and used 14-21 days post-seeding to determine compound permeability. Monolayer integrity is determined by Lucifer yellow permeability as quantified by fluorescent emission or Transepithelial Electrical Resistance (TEER) using an Ohm meter. Test compounds are added to the apical chamber, and 2 hours later, compound levels in the basolateral (B) and apical (A) chambers are determined using LC-MS to yield A-B and B-A efflux as routinely performed. As an alternative to the custom AlphaLISA for detection of NRG1 cleavage, one can perform the NRG1 assay in cells transfected with NRG1 plasmid with ALP and detect the cleavage product in the media.

Evaluation of Leads in In Vitro ADME/T Assays; Molecular Mechanism Studies to Determine Site of Binding on BACE.

Binding of promising candidates to BACE can be performed to obtain information on mechanism of allosteric inhibition. This can be done by competitive ELISA/fluorescence polarization analysis, SPR, Top-down MS, and co-crystallization studies.

Competitive ELISA Assays for Compound-BACE Exosite Binding.

Competitive assays can be used to study compound: BACE interaction to ascertain if there is competition with a known active-site BACE inhibitor such as OM-99 (A Known BACE inhibitor). An active-site inhibitor desirably does not compete with an allosteric inhibitor for BACE binding. In the second competitive binding assay, displacement of AlexaFluor488-labeled peptide 65005 or analogs (FIG. 17C) binding to BACE by candidate compound can be used to determine if the allosteric small molecule inhibitor interacts with the same binding site. Testing can be done at a single concentration of (10 μM) for both labeled peptide and small molecule.

SPR for Identification of Protein-Compound Interactions.

SPR binding analysis methodology is well-established and gives a facile technique to identify and quantify molecular interactions. In this optical technique, one molecule—BACE—is immobilized on a CMS sensor chip (Biacore) by amine coupling and one is mobile (the analyte). The chip is inserted into the flow chamber of the Biacore 3000 instrument (Biacore, AB, Uppsala, Sweden), and the analyte dissolved in a solution phase comprising HBS-EP buffer, which contains 150 mM NaCl, 10 mM HEPES, pH 7.4, 3 mM EDTA, and 0.005% polysorbate 20 traverses the sensors at a typical flow rate of 50 μl/min resulting in binding to the immobilized BACE, producing a change in refractive index which can be precisely quantified and binding affinities determined. Costar low-retention polypropylene tubes (catalog number 3207) can be used throughout. Binding results can be expressed in resonance units and kinetic studies can be analyzed with BIA evaluation Software Version 4.1 to determine rate constants (Ka and Kd) and affinity. SPR thus can be used to quantify BACE-inhibitor interactions and would be done on many 'hits'.

Top-Down MS Determination of Compound-BACE Interaction Site.

Experiments to determine compound:BACE site of interaction can be done. In these experiments, native Top-down MS with the electrospray ionization technique can be utilized. By combining various activation/dissociation techniques, including collisionally-activated dissociation, infrared multiphoton dissociation (IRMPD), and in particular electron capture dissociation, the amino acid sequence of the sites of binding between BACE and allosteric inhibitors can be revealed. Since ECD dissociates backbone bonds of protein complexes, the noncovalent ligand interaction is retained (FIG. 15) and the data generated can be used to determine directly the sites of ligand binding to protein targets. Using the ultra-high resolution 15-Tesla Fourier transform ion cyclotron resonance mass spectrometer available at UCLA, the Loo group has mapped the binding sites of a variety of small molecule ligands to protein targets. The data from these studies can complement structural data obtained from co-crystallization studies and can greatly help with modeling of the exosite(s) and analog design. These studies can be done on selected lead candidates.

Co-Crystallization Screening Trials.

The Crystallization Condition Screening Core used for these studies is capable of setting up 288 unique crystallization experiments in three minutes, using the nanoliter liquid handling device TTP LabTech Mosquito. Prior to each trial, each sample is scrutinized using dynamic light-scattering to prevent samples with impurities, or those that form nonspecific oligomers, from entering crystallization trials. The best samples are placed in vapor-diffusion crystallization setups and monitored. Crystals that appear are viewed using a Korima PRS-1000 UV Microscope. The Condition Screening Core receives feedback from the Crystallography Technology Center and is able to select the most appropriate conditions for optimization, if the need exists. In certain embodiments the use soaking and co-crystallization experiments described below can be utilized.

Soaking of Various Inhibitors into Native Crystals with BACE.

Native crystals of BACE can be placed in a solution containing mother liquor and allosteric BACE inhibitor, and soaked for various periods. Diffraction data can be collected after the soak to determine whether the uptake of the inhibitor produces a co-crystal structure.

Co-Crystallization of BACE with Allosteric Inhibitors.

In addition to soaking, BACE can be co-crystalized with allosteric inhibitors as needed.

Diffraction Data Collection & Structure Analysis.

Crystals from other samples can be either subjected to Coomassie-blue dye or are sent for diffraction screening to the UCLA-DOE X-Ray Crystallography Technology Center (Macromolecular). Crystals that show appreciable diffraction can have a full dataset collected in-house, and may be sent to the APS beamline in Chicago for further refinement.

Solubility, Protein Binding, Metabolic Stability & Cell Toxicity.

For promising allosteric BACE inhibitors solubility and protein binding would be ascertained using chemiluminescence and filtration/dialysis assays routinely used (62, 63). For determination of metabolic stability, the compound(s) can be incubated with S9 fraction liver microsomes and stability measured by HPLC over a period of 1 hour (64, 65), as is routine. For the toxicity assay, cell viability can be assessed by ATP content using CellTiter Glo® (Promega Corp., Madison, WI Rapid protein binding can be done by using a 5 μm Chiral-HSA, 50 mm column (Chrom Tech, France) for HPLC.

Alternative Strategies:

Should SPR not reveal interactions, as an alternative to or in conjunction with SPR, Isothermal Titration Calorimetry may be used to determine compound-BACE interactions.

Evaluation of Oral Brain Availability, Efficacy, and Safety of Selected Leads.

Compounds meeting desired criteria can progress to PK studies to ascertain brain penetrance and efficacy studies in AD model mice to determine lead compound behavioral and biochemical effects.

Pharmacokinetics.

Both oral and subcutaneous injection can be used; the latter in anticipation of proof-of-concept studies with compounds that are found to be orally unavailable. For each route, 12 adult male mice can receive 10 or 30 mg/kg test compound and 2 mice can be euthanized at 30 min, 1, 2, 4, 6, and 8 hour time points. Mice can be over-anesthetized with ketamine/xylazine and the chest opened for cardiac puncture and collection of blood for plasma isolation by centrifugation. This can be immediately followed by saline perfusion and dissection of brain tissue for compound level analysis at Integrated Analytical Solutions (IAS, Berkeley, CA). Compound peak, Cmax and exposure can determined using PK Solutions software (Summit PK).

Efficacy Testing.

Lead candidates with good brain penetrance can progress to efficacy testing in the J20 model.

AD Model Mice.

Mice, expressing of human APP with Familial Alzheimer's disease mutations such as the J20 mice which is under the control of the platelet-derived growth factor promoter (PDAPP) will be used. Target engagement in these mice can be measured by changes in sAPPβ and Aβ42. Impairment of working object & spatial memory can also be monitored.

Efficacy Studies.

Cohorts of 12 (6 male, 6 female) 5 month-old J20 mice (N # chosen to power statistics) can be used to compare test compound and vehicle-only. For example, in certain embodiments, 12 non-transgenic mice will receive vehicle-only. Mice can be treated orally daily for 28 days at a dose determined by in vitro IC50 analysis and brain penetrance/exposure. Cohorts can be sibling- and aged-matched amongst groups. Working and spatial memory can be assessed pre- and end-study using the Novel Object Recognition and Novel Location Recognition paradigms. At the end of the study, mice can be euthanized as described above for PK, with the addition of hippocampal and entorhinal cortical micro-dissection for snap freezing on dry ice and later biochemical analysis. Remaining tissue can be sent to IAS for compound level analysis. Biochemical readouts from Hip/ECx can include sAPPα and sAPPβ by AlphaLISA (Perkin-Elmer) and Aβ 1-40, 1-42, βCTF, total tau, and ptau by ELISA. In the standard protocol, all tissue is sonicated at 20% weight/volume in AlphaLISA buffer complemented with Complete Protease Inhibitor and phosphatase inhibitor (Roche) on ice. Samples are used directly for AlphaLISA and 43CTF, total tau and ptau ELISA, but sonicates are diluted with 5M guanidine HCl for Aβ ELISA analysis. IHC studies on advanced leads will include labeling of brain tissue for Aβ and synaptophysin.

Safety Panel Testing.

On advanced leads a safety profile analysis can be conducted. As in vitro safety profiling services are important to test for off-target interactions of advanced lead compounds, one can use the SafetyScreen 44 offered by Eurofins Cerep (www.cerep.com) for this testing. All the 44 selected targets, recommended by 4 pharmaceutical companies, are gathered in a cost-effective panel that associates robustness and strategy.

Uses of Allosteric BACE Inhibitors.

As evidenced by their ability to inhibit BACE in AD animal models, it is believed the compounds described herein find utility, inter alia, in the prophylaxis and/or treatment of pathologies characterized by a BACE derived amyloidogenic process.

Without being bound to a particular theory, it is believed the compounds described herein also find utility in the treatment of various psychiatric disorders and neurological diseases including depression, anxiety-related disorders and feeding disorders, and in the etiology and pathophysiology of Parkinson's disease, Huntington's disease, progressive supranuclear palsy and amyotrophic lateral sclerosis. Additionally, it is believed the compounds described herein can be used in the prophylaxis and treatment of conditions such as Cushing's disease, hypertension, stroke, irritable bowel syndrome, stress-induced gastric ulceration, premenstrual syndrome, sexual dysfunction, premature labor, inflammatory disorders, allergies, multiple sclerosis, visceral pain, sleep disorders, pituitary tumors or ectopic pituitary-derived tumors, chronic fatigue syndrome and fibromyalgia.

With respect to amyloidogenic pathologies such as Alzheimer's disease (and amyloidogenic MCI), it is noted that the prevailing view of Alzheimer's disease is that amyloid-beta peptides cause toxicity through chemical and physical mechanisms, such as metal binding, ROS production, and membrane damage. Our data suggest an alternative view of AD as an imbalance in physiological signaling mediated by APP. In this model, Aβ functions physiologically as an anti-trophin, and Aβ binding to APP induces the formation of peptides that mediate neurite retraction and cell death (see, e.g., Lu et al., (2000) Nat. Med., 6: 397-404). This imbalance in physiological signaling can result in increased processing of APP by an amyloidogenic pathway and reduced processing of APP by a non-amyloidogenic pathway.

In the amyloidogenic pathway is initiated when β-secretase cleaves APP at the amino terminus of the Aβ, thereby releasing the APPsβ ectodomain ("sAPPβ"). In contrast, in the non-amyloidogeic pathway, APP is first cleaved by α-secretase within the Aβ sequence, releasing the APPsα ectodomain ("sAPPα"). APP processing by the nonamyloidogenic and amyloidogenic pathways is known in the art and reviewed, e.g., by Xu (2009) J Alzheimers Dis. 16(2):211-224 and De Strooper et al. (2010) Nat Rev Neurol 6(2):99-107.

Without being bound to a particular theory, it is believe the compounds described herein can be used, inter alia, by specifically inhibiting BACE activity, to promote processing of APP by the non-amyloidogenic pathway and/or reduce or inhibit processing of APP by the amyloidogenic pathway.

Accordingly, in various embodiments compositions and methods are provided for mitigating in a mammal one or more symptoms associated with a disease characterized by amyloid deposits in the brain (e.g., Alzheimer's disease, Cerebrovascular dementia, Parkinson's disease, Huntington's disease, Cerebral amyloid angiopathy, etc.), or delaying or preventing the onset of symptoms. Compositions and methods are also provided for reducing the risk, lessening the severity, or delaying the progression or onset of a disease characterized by beta-amyloid deposits in the brain of a mammal (e.g., Alzheimer's disease, Cerebrovascular dementia, Parkinson's disease, Huntington's disease, Cerebral amyloid angiopathy, etc.). In certain embodiments compositions and methods are provided for preventing or delaying the onset of a pre-Alzheimer's condition and/or cognitive dysfunction, and/or ameliorating one or more symptoms of a pre-Alzheimer's condition and/or cognitive dysfunction, or preventing or delaying the progression of a pre-Alzheimer's condition or cognitive dysfunction to Alzheimer's disease in a mammal. In certain embodiments compositions and methods are provided for promoting the processing of amyloid precursor protein by the non-amyloidogenic pathway as characterized by increasing sAPP β and/or the sAPPβ/A β42 ratio in a mammal.

Accordingly, in various embodiments, the use of one or more allosteric BACE inhibitors described herein (see, e.g., Formula I, Formula II, Formula III, FIGS. 9 and 10 and the like) or formulations thereof and/or an enantiomer thereof, and/or a mixture of enantiomers, and/or a mixture of two or more diastereomers thereof, and/or a pharmaceutically acceptable salt, ester, amide, solvate, hydrate, or prodrug thereof, and/or a derivative thereof for the modulation, and in particular in the reduction of amyloidogenic pathologies (e.g., MCI, Alzheimer's disease, age-related macular degeneration, Cerebrovascular dementia, Parkinson's disease, and the like) is provided. In certain embodiments, the compounds and/or formulations described herein are used to prevent or delay the onset of a pre-Alzheimer's condition and/or cognitive dysfunction, and/or to ameliorate one or more symptoms of a pre-Alzheimer's condition and/or cognitive dysfunction, and/or to prevent or delay the progression of a pre-Alzheimer's condition or cognitive dysfunction to Alzheimer's disease. In certain embodiments, the compounds and formulations described herein are used in a method of mitigating in a mammal one or more symptoms associated with a disease characterized by amyloid deposits in the brain, or delaying or preventing the onset of said symptoms. In certain embodiments, methods of reducing the risk, lessening the severity, or delaying the progression or onset of a disease characterized by beta-amyloid deposits in the brain of a mammal are also provided. In addition, methods of promoting the processing of amyloid precursor protein by the non-amyloidogenic pathway in a mammal are provided.

Typically each of these methods involve administering to a subject in need thereof, one or more allosteric BACE inhibitor(s) described herein compound or formulations thereof and/or an enantiomer thereof, and/or a mixture of enantiomers thereof, and/or a mixture of two or more diastereomers thereof, and/or a pharmaceutically acceptable salt, ester, amide, solvate, hydrate, or prodrug thereof, and/or a derivative thereof, in an amount sufficient to produce the desired activity (e.g., mitigating one or more symptoms associated with a disease characterized by amyloid deposits in the brain, or delaying or preventing the onset of said symptoms, and/or reducing the risk, lessening the severity, or delaying the progression or onset of a disease characterized by beta-amyloid deposits in the brain of a mammal, and/or promoting the processing of amyloid precursor protein (APP) by the non-amyloidogenic pathway).

While the methods described herein are detailed primarily in the context of mild cognitive impairment (MCI) and Alzheimer's disease (AD) it is believed they can apply equally to other pathologies characterized by amyloidosis. Illustrative, but non-limiting list of conditions characterized by amyloid plaque formation are shown in Table 1.

TABLE 1

Illustrative, but non-limiting pathologies characterized by amyloid formation/deposition.

| Disease | Characteristic Protein | Abbreviation |
|---|---|---|
| Alzheimer's disease | Beta amyloid | Aβ |
| Diabetes mellitus type 2 | IAPP (Amylin) | AIAPP |
| Parkinson's disease | Alpha-synuclein | |
| Transmissible spongiform encephalopathy e.g. Bovine spongiform encephalopathy | Prion | APrP |
| Huntington's Disease | Huntingtin | |
| Medullary carcinoma of the thyroid | Calcitonin | ACal |
| Cardiac arrhythmias, Isolated atrial amyloidosis | Atrial natriuretic factor | AANF |
| Atherosclerosis | Apolipoprotein AI | AApoA1 |
| Rheumatoid arthritis | Serum amyloid A | AA |
| Aortic medial amyloid | Medin | AMed |
| Prolactinomas | Prolactin | APro |
| Familial amyloid polyneuropathy | Transthyretin | ATTR |
| Hereditary non-neuropathic systemic amyloidosis | Lysozyme | ALys |
| Dialysis related amyloidosis | Beta 2 microglobulin | Aβ2M |
| Finnish amyloidosis | Gelsolin | AGel |
| Lattice corneal dystrophy | Keratoepithelin | AKer |
| Cerebral amyloid angiopathy | Beta amyloid | Aβ |
| Cerebral amyloid angiopathy (Icelandic type) | Cystatin | ACys |
| systemic AL amyloidosis | Immunoglobulin light chain AL | AL |
| Sporadic Inclusion Body Myositis | S-IBM | none |
| Age-related macular degeneration (AMD) | | |
| Cerebrovascular dementia | | |

Subjects Who can Benefit from the Present Methods

Subjects/patients amenable to treatment using the methods described herein include individuals at risk of disease (e.g., a pathology characterized by amyloid plaque formation) but not showing symptoms, as well as subjects presently showing symptoms. Accordingly, certain subjects include subjects at increased risk for the onset of a pre-Alzheimer's condition and/or cognitive dysfunction (e.g., MCI), and/or subjects diagnosed as having a pre-Alzheimer's condition and/or cognitive dysfunction (e.g., MCI).

Accordingly, in various embodiments, therapeutic and/or prophylactic methods are provided that utilize the allosteric BACE inhibitor(s) (or formulations thereof and/or an enantiomer thereof, a mixture of enantiomers, or a mixture of two or more diastereomers thereof; or a pharmaceutically acceptable salt, ester, amide, solvate, hydrate, or prodrug thereof, or a derivative thereof) are provided. Typically, the methods involve administering one or more allosteric BACE inhibitor (s) described herein and/or a formulation thereof to a subject (e.g., to a human in need thereof) in an amount sufficient/effective to realize the desired therapeutic or prophylactic result.

Prophylaxis

In certain embodiments, the allosteric BACE inhibitor(s) described herein (or enantiomer thereof, a mixture of enantiomers, or a mixture of two or more diastereomers thereof; or a pharmaceutically acceptable salt, ester, amide, solvate, hydrate, or prodrug thereof or derivatives thereof, and/or formulations comprising any of these) are utilized in various prophylactic contexts. Thus, for example, in certain embodiments, the allosteric BACE inhibitor(s) can be used to prevent or delay the onset of a pre-Alzheimer's cognitive dysfunction, and/or to ameliorate one more symptoms of a pre-Alzheimer's condition and/or cognitive dysfunction, and/or to prevent or delay the progression of a pre-Alzheimer's condition and/or cognitive dysfunction to Alzheimer's disease.

Accordingly, in certain embodiments, the prophylactic methods described herein are contemplated for subjects identified as "at risk" and/or as having evidence of early MCI and/or early Alzheimer's Disease (AD) pathological changes, but who do not meet clinical criteria for MCI or dementia. Without being bound to a particular theory, it is believed that even this "preclinical" stage of the disease represents a continuum from completely asymptomatic individuals with biomarker evidence suggestive of AD-pathophysiological process (abbreviated as AD-P, see, e.g., Sperling et al., (2011) Alzheimer's & Dementia, 1-13) at risk for progression to AD dementia to biomarker-positive individuals who are already demonstrating very subtle decline but not yet meeting standardized criteria for MCI (see, e.g., Albert et al., (2011) Alzheimer's and Dementia, 1-10 (doi: 10.1016/j.jalz.2011.03.008)).

This latter group of individuals might be classified as "not normal, not MCI" but can be designated "pre-symptomatic" or "pre-clinical or "asymptomatic" or "premanifest"). In various embodiments, this continuum of pre-symptomatic AD can also encompass (1) individuals who carry one or more apolipoprotein E (APOE) ε4 alleles who are known or believed to have an increased risk of developing AD dementia, at the point they are AD-P biomarker-positive, and (2) carriers of autosomal dominant mutations, who are in the presymptomatic biomarker-positive stage of their illness, and who will almost certainly manifest clinical symptoms and progress to dementia.

A biomarker model has been proposed in which the most widely validated biomarkers of AD-P become abnormal and likewise reach a ceiling in an ordered manner (see, e.g., Jack et al., (2010) Lancet Neurol., 9: 119-128.). This biomarker model parallels proposed pathophysiological sequence of (pre-AD/AD), and is relevant to tracking the preclinical (asymptomatic) stages of AD (see, e.g., FIG. 3 in Sperling et al., (2011) Alzheimer's & Dementia, 1-13). Biomarkers of brain amyloidosis include but are not limited to reductions in CSF Aβ42 and increased amyloid tracer retention on positron emission tomography (PET) imaging. Elevated CSF tau is not specific to AD and is thought to be a biomarker of neuronal injury. Decreased fluorodeoxyglucose 18F (FDG) uptake on PET with a temporoparietal pattern of hypometabolism is a biomarker of AD-related synaptic dysfunction. Brain atrophy on structural magnetic resonance imaging (Mill) in a characteristic pattern involving the medial temporal lobes, paralimbic and temporoparietal cortices is a biomarker of AD-related neurodegeneration. Other markers include, but are not limited to volumetric MRI, FDG-PET, or plasma biomarkers (see, e.g., Vemuri et al., (2009) Neurology, 73: 294-301; Yaffe et al., (2011) JAMA 305: 261-266).

In certain embodiments, the subjects suitable for the prophylactic methods contemplated herein include but are not limited to subject characterized as having asymptomatic cerebral amyloidosis. In various embodiments, these individuals have biomarker evidence of Aβ accumulation with elevated tracer retention on PET amyloid imaging and/or low Aβ42 in CSF assay, but typically no detectable evidence of additional brain alterations suggestive of neurodegeneration or subtle cognitive and/or behavioral symptomatology.

It is noted that currently available CSF and PET imaging biomarkers of Aβ primarily provide evidence of amyloid accumulation and deposition of fibrillar forms of amyloid. Data suggest that soluble or oligomeric forms of Aβ are likely in equilibrium with plaques, which may serve as reservoirs. In certain embodiments, it is contemplated that there is an identifiable preplaque stage in which only soluble forms of Aβ are present. In certain embodiments, it is contemplated that oligomeric forms of amyloid may be critical in the pathological cascade, and provide useful markers. In addition, early synaptic changes may be present before evidence of amyloid accumulation.

In certain embodiments, the subjects suitable for the prophylactic methods contemplated herein include, but are not limited to, subjects characterized as amyloid positive with evidence of synaptic dysfunction and/or early neurodegeneration. In various embodiments, these subjects have evidence of amyloid positivity and presence of one or more markers of "downstream" AD-P-related neuronal injury. Illustrative, but non-limiting markers of neuronal injury include, but are not limited to (1) elevated CSF tau or phospho-tau, (2) hypometabolism in an AD-like pattern (e.g., posterior cingulate, precuneus, and/or temporoparietal cortices) on FDG-PET, and (3) cortical thinning/gray matter loss in a specific anatomic distribution (e.g., lateral and medial parietal, posterior cingulate, and lateral temporal cortices) and/or hippocampal atrophy on volumetric MRI. Other markers include but are not limited to fMRI measures of default network connectivity. In certain embodiments, early synaptic dysfunction, as assessed by functional imaging techniques such as FDG-PET and fMRI, can be detectable before volumetric loss. Without being bound to a particular theory, it is believed that amyloid-positive individuals with evidence of early neurodegeneration may be farther down the trajectory (e.g., in later stages of preclinical (asymptomatic) AD).

In certain embodiments, the subjects suitable for the prophylactic methods contemplated herein include, but are not limited to, subjects characterized as amyloid positive with evidence of neurodegeneration and subtle cognitive decline. Without being bound to a particular theory, it is believed that those individuals with biomarker evidence of amyloid accumulation, early neurodegeneration, and evidence of subtle cognitive decline are in the last stage of preclinical (asymptomatic) AD and are approaching the border zone with clinical criteria for mild cognitive impairment (MCI). These individuals may demonstrate evidence of decline from their own baseline (particularly if proxies of cognitive reserve are taken into consideration), even if they still perform within the "normal" range on standard cognitive measures. Without being bound to a particular theory, it is believed that more sensitive cognitive measures, particularly with challenging episodic memory measures, may detect very subtle cognitive impairment in amyloid-positive individuals. In certain embodiments, criteria include, but are not limited to, self-complaint of memory decline or other subtle neurobehavioral changes.

As indicated above, subjects/patients amenable to prophylactic methods described herein include individuals at risk of disease (e.g., a pathology characterized by amyloid plaque formation such as MCI) but not showing symptoms, as well as subjects presently showing certain symptoms or markers. It is known that the risk of MCI and later Alzheimer's disease generally increases with age. Accordingly, in asymptomatic subjects with no other known risk factors, in certain embodiments, prophylactic application is contemplated for subjects over 50 years of age, or subjects over 55 years of age, or subjects over 60 years of age, or subjects over 65 years of age, or subjects over 70 years of age, or subjects over 75 years of age, or subjects over 80 years of age, in particular to prevent or slow the onset or ultimate severity of mild cognitive impairment (MCI), and/or to slow or prevent the progression from MCI to early stage Alzheimer's disease (AD).

In certain embodiments, the methods described herein present methods are especially useful for individuals who do have a known genetic risk of Alzheimer's disease (or other amyloidogenic pathologies), whether they are asymptomatic or showing symptoms of disease. Such individuals include those having relatives who have experienced MCI or AD (e.g., a parent, a grandparent, a sibling), and those whose risk is determined by analysis of genetic or biochemical markers. Genetic markers of risk toward Alzheimer's disease include, for example, mutations in the APP gene, particularly mutations at position 717 and positions 670 and 671 referred to as the Hardy and Swedish mutations respectively (see, e.g., Hardy (1997) Trends. Neurosci., 20: 154-159). Other markers of risk include mutations in the presenilin genes (PS1 and PS2), family history of AD, having the familial Alzheimer's disease mutation, the APOE ε4 allele, hypercholesterolemia or atherosclerosis. Further susceptibility genes for the development of Alzheimer's disease are reviewed, e.g., in Sleegers, et al., (2010) Trends Genet. 26(2): 84-93.

In some embodiments, the subject is asymptomatic but has familial and/or genetic risk factors for developing MCI or Alzheimer's disease. In asymptomatic patients, treatment can begin at any age (e.g., 20, 30, 40, 50, years of age). Usually, however, it is not necessary to begin treatment until a patient reaches at least about 40, 50, 60, 70 or 80 years of age.

In some embodiments, the subject is one who exhibits symptoms, for example, of mild cognitive impairment (MCI) or Alzheimer's disease (AD). Individuals presently suffering from Alzheimer's disease can be recognized from characteristic dementia, as well as the presence of risk factors described above. In addition, a number of diagnostic tests are available for identifying individuals who have AD. These include, but are not limited to measurement of CSF Tau, phospho-tau (pTau), Aβ42 levels and C-terminally cleaved APP fragment (APPneo). Elevated total-Tau (tTau), phospho-Tau (pTau), APPneo, soluble Aβ40, pTau/Aβ42 ratio and tTau/Aβ42 ratio, and decreased Aβ42 levels, Aβ42/Aβ40 ratio, Aβ42/Aβ38 ratio, sAPPα levels, sAPPα/sAPPβ ratio, sAPPα/Aβ40 ratio, and sAPPα/Aβ42 ratio signify the presence of AD. In some embodiments, the subject or patient is clinically diagnosed as having MCI. Increased levels of neural thread protein (NTP) in urine and/or increased levels of α2-macroglobulin (α2M) and/or complement factor H (CFH) in plasma are also biomarkers of MCI and/or AD (see, e.g., Anoop et al., (2010) Int. J. Alzheimer's Dis. 2010:606802).

In certain embodiments, subjects amenable to treatment may have age-associated memory impairment (AAMI), or mild cognitive impairment (MCI). The methods described herein are particularly well-suited to the prophylaxis and/or treatment of MCI, particularly MCI characterized by an amyloidogenic process. In such instances, the methods can delay or prevent the onset of MCI, and or reduce one or more symptoms characteristic of MCI and/or delay or prevent the progression from MCI to early-, mid- or late-stage Alzheimer's disease, and/or reduce the ultimate severity of the disease.

Mild Cognitive Impairment (MCI)

In various embodiments, the allosteric BACE inhibitor(s) described herein (e.g., or formulations thereof, and/or an enantiomer, a mixture of enantiomers, or a mixture of two or more diastereomers thereof, or a pharmaceutically acceptable salt, ester, amide, solvate, hydrate, or prodrug thereof or derivatives thereof) can be used for the treatment and/or prophylaxis of age-related cognitive decline and/or for the treatment and/or prophylaxis of mild cognitive impairment (MCI). Mild cognitive impairment, also known as incipient dementia, or isolated memory impairment) is a diagnosis given to individuals who have cognitive impairments beyond that expected for their age and education, but that typically do not interfere significantly with their daily activities (see, e.g., Petersen et al., (1999) Arch. Neurol. 56(3): 303-308). It is considered in many instances to be a boundary or transitional stage between normal aging and dementia. Although MCI can present with a variety of symptoms, when memory loss is the predominant symptom it is termed "amnestic MCI" and is can be a risk factor for Alzheimer's disease (see, e.g., Grundman et al., (2004) Arch. Neurol. 61(1): 59-66; and on the internet at en.wikipedia.org/wiki/Mild_cognitive_impairment-cite_note-Grundman-1). When individuals have impairments in domains other than memory it is often classified as non-amnestic single- or multiple-domain MCI and these individuals are believed to be more likely to convert to other dementias (e.g. dementia with Lewy bodies). There is evidence suggesting that while amnestic MCI patients may not meet neuropathologic criteria for Alzheimer's disease, patients may be in a transitional stage of evolving Alzheimer's disease; patients in this hypothesized transitional stage demonstrated diffuse amyloid in the neocortex and frequent neurofibrillary tangles in the medial temporal lobe (see, e.g., Petersen et al., (2006) Arch. Neurol., 63(5): 665-72).

The diagnosis of MCI typically involves a comprehensive clinical assessment including clinical observation, neuroimaging, blood tests and neuropsychological testing. In certain embodiments, diagnostic criteria for MCI include, but are not limited to those described by Albert et al., (2011) Alzheimer's & Dementia. 1-10. As described therein, diagnostic criteria include (1) core clinical criteria that could be used by healthcare providers without access to advanced imaging techniques or cerebrospinal fluid analysis, and (2) research criteria that could be used in clinical research settings, including clinical trials. The second set of criteria incorporate the use of biomarkers based on imaging and cerebrospinal fluid measures. The final set of criteria for mild cognitive impairment due to AD has four levels of certainty, depending on the presence and nature of the biomarker findings.

In certain embodiments, clinical evaluation/diagnosis of MCI involves: (1) Concern reflecting a change in cognition reported by patient or informant or clinician (e.g., historical or observed evidence of decline over time); (2) Objective evidence of Impairment in one or more cognitive domains, typically including memory (e.g., formal or bedside testing to establish level of cognitive function in multiple domains); (3) Preservation of independence in functional abilities; (4) Not demented; and in certain embodiments, (5) An etiology of MCI consistent with AD pathophysiological processes. Typically, vascular, traumatic, medical causes of cognitive decline are ruled out where possible. In certain embodiments, evidence of longitudinal decline in cognition is identified, when feasible. Diagnosis is reinforced by a history consistent with AD genetic factors, where relevant.

With respect to impairment in cognitive domain(s), there should be evidence of concern about a change in cognition, in comparison with the person's previous level. There should be evidence of lower performance in one or more cognitive domains that is greater than would be expected for the patient's age and educational background. If repeated assessments are available, then a decline in performance should be evident over time. This change can occur in a variety of cognitive domains, including memory, executive function, attention, language, and visuospatial skills. An impairment in episodic memory (e.g., the ability to learn and retain new information) is seen most commonly in MCI patients who subsequently progress to a diagnosis of AD dementia.

With respect to preservation of independence in functional abilities, it is noted that persons with MCI commonly have mild problems performing complex functional tasks which they used to perform shopping. They may take more time, be less efficient, and make more errors at performing such activities than in the past. Nevertheless, they generally maintain their independence of function in daily life, with minimal aids or assistance.

With respect to dementia, the cognitive changes should be sufficiently mild that there is no evidence of a significant impairment in social or occupational functioning. If an individual has only been evaluated once, change will be inferred from the history and/or evidence that cognitive performance is impaired beyond what would have been expected for that individual.

Cognitive testing is optimal for objectively assessing the degree of cognitive impairment for an individual. Scores on cognitive tests for individuals with MCI are typically 1 to 1.5 standard deviations below the mean for their age and education matched peers on culturally appropriate normative data (e.g., for the impaired domain(s), when available).

Episodic memory (i.e., the ability to learn and retain new information) is most commonly seen in MCI patients who subsequently progress to a diagnosis of AD dementia. There are a variety of episodic memory tests that are useful for identifying those MCI patients who have a high likelihood of progressing to AD dementia within a few years. These tests typically assess both immediate and delayed recall, so that it is possible to determine retention over a delay. Many, although not all, of the tests that have proven useful in this regard are wordlist learning tests with multiple trials. Such tests reveal the rate of learning over time, as well as the maximum amount acquired over the course of the learning trials. They are also useful for demonstrating that the individual is, in fact, paying attention to the task on immediate recall, which then can be used as a baseline to assess the relative amount of material retained on delayed recall. Examples of such tests include (but are not limited to: the Free and Cued Selective Reminding Test, the Rey Auditory Verbal Learning Test, and the California Verbal Learning Test. Other episodic memory measures include, but are not limited to: immediate and delayed recall of a paragraph such as the Logical Memory I and II of the Wechsler Memory Scale Revised (or other versions) and immediate and delayed recall of nonverbal materials, such as the Visual Reproduction subtests of the Wechsler Memory Scale-Revised I and II.

Because other cognitive domains can be impaired among individuals with MCI, it is desirable to examine domains in addition to memory. These include, but are not limited to executive functions (e.g., set-shifting, reasoning, problem-solving, planning), language (e.g., naming, fluency, expressive speech, and comprehension), visuospatial skills, and attentional control (e.g., simple and divided attention). Many clinical neuropsychological measures are available to assess these cognitive domains, including (but not limited to the Trail Making Test (executive function), the Boston Naming Test, letter and category fluency (language), FIG. copying (spatial skills), and digit span forward (attention).

As indicated above, genetic factors can be incorporated into the diagnosis of MCI. If an autosomal dominant form of AD is known to be present (e.g., mutation in APP, PS1, PS2), then the development of MCI is most likely the precursor to AD dementia. The large majority of these cases develop early onset AD (e.g., onset below 65 years of age).

In addition, there are genetic influences on the development of late onset AD dementia. For example, the presence of one or two ε4 alleles in the apolipoprotein E (APOE) gene is a genetic variant broadly accepted as increasing risk for late-onset AD dementia. Evidence suggests that an individual who meets the clinical, cognitive, and etiologic criteria for MCI, and is also APOE ε4 positive, is more likely to progress to AD dementia within a few years than an individual without this genetic characteristic. It is believed that additional genes play an important, but smaller role than APOE and also confer changes in risk for progression to AD dementia (see, e.g., Bertram et al., (2010) Neuron, 21: 270-281).

In certain embodiments, subjects suitable for the prophylactic methods described herein (e.g., administration of a allosteric BACE inhibitor(s) described herein, and/or an enantiomer, a mixture of enantiomers, or a mixture of two or more diastereomers thereof; or a pharmaceutically acceptable salt, ester, amide, solvate, hydrate, or prodrug thereof or derivatives thereof, and/or a formulation comprising any of these) include, but need not be limited to subjects identified having one or more of the core clinical criteria described above and/or subjects identified with one or more "research criteria" for MCI, e.g., as described below.

"Research criteria" for the identification/prognosis of MCI include, but are not limited to biomarkers that increase the likelihood that MCI syndrome is due to the pathophysiological processes of AD. Without being bound to a particular theory, it is believed that the conjoint application of clinical criteria and biomarkers can result in various levels of certainty that the MCI syndrome is due to AD pathophysiological processes. In certain embodiments, two categories of biomarkers have been the most studied and applied to clinical outcomes are contemplated. These include "Aβ" (which includes CSF Aβ42 and/or PET amyloid imaging) and "biomarkers of neuronal injury" (which include, but are not limited to CSF tau/p-tau, hippocampal, or medial temporal lobe atrophy on MRI, and temporoparietal/precuneus hypometabolism or hypoperfusion on PET or SPECT).

Without being bound to a particular theory, it is believed that evidence of both Aβ, and neuronal injury (either an increase in tau/p-tau or imaging biomarkers in a topographical pattern characteristic of AD), together confers the highest probability that the AD pathophysiological process is present. Conversely, if these biomarkers are negative, this may provide information concerning the likelihood of an alternate diagnosis. It is recognized that biomarker findings may be contradictory and accordingly any biomarker combination is indicative (an indicator) used on the context of a differential diagnosis and not itself dispositive. It is recognized that varying severities of an abnormality may confer different likelihoods or prognoses, that are difficult to quantify accurately for broad application.

For those potential MCI subjects whose clinical and cognitive MCI syndrome is consistent with AD as the etiology, the addition of biomarker analysis effects levels of certainty in the diagnosis. In the most typical example in which the clinical and cognitive syndrome of MCI has been established, including evidence of an episodic memory disorder and a presumed degenerative etiology, the most likely cause is the neurodegenerative process of AD. However, the eventual outcome still has variable degrees of certainty. The likelihood of progression to AD dementia will vary with the severity of the cognitive decline and the nature of the evidence suggesting that AD pathophysiology is the underlying cause. Without being bound to a particular theory it is believed that positive biomarkers reflecting neuronal injury increase the likelihood that progression to dementia will occur within a few years and that positive findings reflecting both Ab accumulation and neuronal injury together confer the highest likelihood that the diagnosis is MCI due to AD.

A positive Aβ biomarker and a positive biomarker of neuronal injury provide an indication that the MCI syndrome is due to AD processes and the subject is well suited for the methods described herein (e.g., treatment with a allosteric BACE inhibitor(s) described herein).

A positive Aβ biomarker in a situation in which neuronal injury biomarkers have not been or cannot be tested or a positive biomarker of neuronal injury in a situation in which Aβ biomarkers have not been or cannot be tested indicate an intermediate likelihood that the MCI syndrome is due to AD. Such subjects are believed to be well suited for the methods described herein Negative biomarkers for both Aβ and neuronal injury suggest that the MCI syndrome is not due to AD. In such instances the subjects may not be well suited for the methods described herein.

There is evidence that magnetic resonance imaging can observe deterioration, including progressive loss of gray matter in the brain, from mild cognitive impairment to full-blown Alzheimer disease (see, e.g., Whitwell et al., (2008) Neurology 70(7): 512-520). A technique known as PiB PET imaging is used to clearly show the sites and shapes of beta amyloid deposits in living subjects using a C11 tracer that binds selectively to such deposits (see, e.g., Jack et al., (2008) Brain 131(Pt 3): 665-680).

In certain embodiments, MCI is typically diagnosed when there is 1) Evidence of memory impairment; 2) Preservation of general cognitive and functional abilities; and 3) Absence of diagnosed dementia.

In certain embodiments, MCI and stages of Alzheimer's disease can be identified/categorized, in part by Clinical Dementia Rating (CDR) scores. The CDR is a five point scale used to characterize six domains of cognitive and functional performance applicable to Alzheimer disease and related dementias: Memory, Orientation, Judgment & Problem Solving, Community Affairs, Home & Hobbies, and Personal Care. The information to make each rating is obtained through a semi-structured interview of the patient and a reliable informant or collateral source (e.g., family member).

The CDR table provides descriptive anchors that guide the clinician in making appropriate ratings based on interview data and clinical judgment. In addition to ratings for each domain, an overall CDR score may be calculated through the use of an algorithm. This score is useful for characterizing and tracking a patient's level of impairment/dementia: 0=Normal; 0.5=Very Mild Dementia; 1=Mild Dementia; 2=Moderate Dementia; and 3=Severe Dementia. An illustrative CDR table is shown in Table 2.

TABLE 2

Illustrative clinical dementia rating (CDR) table.

| Impairment: CDR: | None 0 | Questionable 0.5 | Mild 1 | Moderate 2 | Severe 3 |
|---|---|---|---|---|---|
| Memory | No memory loss or slight inconsistent forgetfulness | Consistent slight forgetfulness; partial recollection of events' "benign" forgetfulness | Moderate memory loss; more marked for recent events; defect interferes with everyday activities | Severe memory loss; only highly learned material retained; new material rapidly lost | Severe memory loss; only fragments remain |
| Orientation | Fully oriented | Fully oriented except for slight difficulty with time relationships | Moderate difficulty with time relationships; oriented for place at examination; may have geographic disorientation elsewhere | Severe difficulty with time relationships; usually disoriented to time, often to place. | Oriented to person only |
| Judgment & Problem Solving | Solves everyday problems & handles business & financial affairs well; judgment good in relation to past performance | Slight impairment in solving problems, similarities, and differences | Moderate difficulty in handling problems, similarities and differences; social judgment usually maintained | Severely impaired in handling problems, similarities and differences; social judgment usually impaired | Unable to make judgments or solve problems |
| Community Affairs | Independent function at usual level in job, shopping, volunteer, and social groups | Slight impairment in these activities | Unable to function independently at these activities although may still be engaged in some; appears normal to casual inspection | No pretense of independent function outside of home Appears well enough to be taken to functions outside a family home | Appears too ill to be taken to functions outside a family home. |
| Home and Hobbies | Life at home, hobbies, and intellectual interests well maintained | Life at home, hobbies, and intellectual interests slightly impaired | Mild bit definite impairment of function at home; more difficult chores abandoned; more complicated hobbies and interests abandoned | Only simple chores preserved; very restricted interests, poorly maintained | No significant function in home |

TABLE 2-continued

| Illustrative clinical dementia rating (CDR) table. | | | | | |
|---|---|---|---|---|---|
| Impairment: CDR: | None 0 | Questionable 0.5 | Mild 1 | Moderate 2 | Severe 3 |
| Personal Care | Fully capable of self-care | | Needs prompting | Requires assistance in dressing, hygiene, keeping of personal effects | Requires much help with personal care; frequent incontinence |

A CDR rating of ~0.5 or ~0.5 to 1.0 is often considered clinically relevant MCI. Higher CDR ratings can be indicative of progression into Alzheimer's disease.

In certain embodiments, administration of one or more agents described herein (e.g., an allosteric BACE inhibitor described herein, and/or an enantiomer, a mixture of enantiomers, or a mixture of two or more diastereomers thereof; or a pharmaceutically acceptable salt, ester, amide, solvate, hydrate, or prodrug thereof or derivative thereof, or a formulation comprising any of the preceding) is deemed effective when there is a reduction in the CSF of levels of one or more components selected from Tau, phospho-Tau (pTau), APPneo, soluble Aβ40, soluble Aβ42, and/or Aβ42/Aβ40 ratio, and/or when there is a reduction of the plaque load in the brain of the subject, and/or when there is a reduction in the rate of plaque formation in the brain of the subject, and/or when there is an improvement in the cognitive abilities of the subject, and/or when there is a perceived improvement in quality of life by the subject, and/or when there is a significant reduction in clinical dementia rating, and/or when the rate of increase in clinical dementia rating is slowed or stopped and/or when the progression from MCI to early stage AD is slowed or stopped.

In some embodiments, a diagnosis of MCI can be determined by considering the results of several clinical tests. For example, Grundman, et al., (2004) Arch Neurol 61: 59-66, report that a diagnosis of MCI can be established with clinical efficiency using a simple memory test (paragraph recall) to establish an objective memory deficit, a measure of general cognition (Mini-Mental State Exam (MMSE), discussed in greater detail below) to exclude a broader cognitive decline beyond memory, and a structured clinical interview with patients and caregivers to verify the patient's memory complaint and memory loss and to ensure that the patient was not demented. Patients with MCI perform, on average, less than 1 standard deviation below normal on nonmemory cognitive measures included in the battery. Tests of learning, attention, perceptual speed, category fluency, and executive function may be impaired in patients with MCI, but these are far less prominent than the memory deficit.

Alzheimer's Disease.

In certain embodiments, the allosteric BACE inhibitor(s) described herein (and/or an enantiomer, a mixture of enantiomers, or a mixture of two or more diastereomers thereof, or a pharmaceutically acceptable salt, ester, amide, solvate, hydrate, or prodrug thereof or derivative thereof) and/or formulations thereof are contemplated for the prophylaxis or therapeutic treatment of Alzheimer's disease. In such instances the methods described herein are useful in preventing or slowing the onset of Alzheimer's disease (AD), in reducing the severity of AD when the subject has transitioned to clinical AD diagnosis, and/or in mitigating one or more symptoms of Alzheimer's disease.

In particular, where the Alzheimer's disease is early stage, the methods can reduce or eliminate one or more symptoms characteristic of AD and/or delay or prevent the progression from MCI to early or later stage Alzheimer's disease, and/or prevent or delay the progression from an early stage of Alzheimer's disease to a later stage of Alzheimer's disease.

Individuals presently suffering from Alzheimer's disease can be recognized from characteristic dementia, as well as the presence of risk factors described above. In addition, a number of diagnostic tests are available for identifying individuals who have AD. Individuals presently suffering from Alzheimer's disease can be recognized from characteristic dementia, as well as the presence of risk factors described above. In addition, a number of diagnostic tests are available for identifying individuals who have AD. These include measurement of CSF Tau, phospho-tau (pTau), sAPPα, sAPPβ, Aβ40, Aβ42 levels and/or C terminally cleaved APP fragment (APPneo). Elevated Tau, pTau, sAPPβ and/or APPneo, and/or decreased sAPPα, soluble Aβ40 and/or soluble Aβ42 levels, particularly in the context of a differential diagnosis, can signify the presence of AD.

In certain embodiments, subjects amenable to treatment may have Alzheimer's disease. Individuals suffering from Alzheimer's disease can also be diagnosed by Alzheimer's disease and Related Disorders Association (ADRDA) criteria. The NINCDS-ADRDA Alzheimer's criteria were proposed in 1984 by the National Institute of Neurological and Communicative Disorders and Stroke and the Alzheimer's Disease and Related Disorders Association (now known as the Alzheimer's Association) and are among the most used in the diagnosis of Alzheimer's disease. McKhann, et al., (1984) Neurology 34(7): 939-944. According to these criteria, the presence of cognitive impairment and a suspected dementia syndrome should be confirmed by neuropsychological testing for a clinical diagnosis of possible or probable AD. However, histopathologic confirmation (microscopic examination of brain tissue) is generally used for a dispositive diagnosis. The NINCDS-ADRDA Alzheimer's Criteria specify eight cognitive domains that may be impaired in AD: memory, language, perceptual skills, attention, constructive abilities, orientation, problem solving and functional abilities). These criteria have shown good reliability and validity.

Baseline evaluations of patient function can made using classic psychometric measures, such as the Mini-Mental State Exam (MMSE) (Folstein et al., (1975) J. Psychiatric Research 12 (3): 189-198), and the Alzheimer's Disease Assessment Scale (ADAS), which is a comprehensive scale for evaluating patients with Alzheimer's Disease status and function (see, e.g., Rosen, et al., (1984) Am. J. Psychiatr., 141: 1356-1364). These psychometric scales provide a measure of progression of the Alzheimer's condition. Suitable qualitative life scales can also be used to monitor treatment. The extent of disease progression can be determined using a Mini-Mental State Exam (MMSE) (see, e.g., Folstein, et al., supra). Any score greater than or equal to 25 points (out of 30) is effectively normal (intact). Below this, scores can indicate severe (≤9 points), moderate (10-20 points) or mild (21-24 points) Alzheimer's disease.

Alzheimer's disease can be broken down into various stages including: 1) Moderate cognitive decline (mild or early-stage Alzheimer's disease), 2) Moderately severe cognitive decline (moderate or mid-stage Alzheimer's disease), 3) Severe cognitive decline (moderately severe or mid-stage Alzheimer's disease), and 4) Very severe cognitive decline (severe or late-stage Alzheimer's disease) as shown in Table 3.

TABLE 3

| Illustrative stages of Alzheimer's disease. |
|---|
| Moderate Cognitive Decline (Mild or early stage AD) |
| At this stage, a careful medical interview detects clear-cut deficiencies in the following areas:<br>Decreased knowledge of recent events.<br>Impaired ability to perform challenging mental arithmetic.<br>For example, to count backward from 100 by 7 s.<br>Decreased capacity to perform complex tasks, such as marketing, planning dinner for guests, or paying bills and managing finances.<br>Reduced memory of personal history.<br>The affected individual may seem subdued and withdrawn, especially in socially or mentally challenging situations. |
| Moderately severe cognitive decline (Moderate or mid-stage Alzheimer's disease) |
| Major gaps in memory and deficits in cognitive function emerge.<br>Some assistance with day-to-day activities becomes essential.<br>At this stage, individuals may:<br>Be unable during a medical interview to recall such important details as their current address, their telephone number, or the name of the college or high school from which they graduated.<br>Become confused about where they are or about the date, day of the week or season.<br>Have trouble with less challenging mental arithmetic; for example, counting backward from 40 by 4 s or from 20 by 2 s.<br>Need help choosing proper clothing for the season or the occasion.<br>Usually retain substantial knowledge about themselves and know their own name and the names of their spouse or children.<br>Usually require no assistance with eating or using the toilet. |
| Severe cognitive decline (Moderately severe or mid-stage Alzheimer's disease) |
| Memory difficulties continue to worsen, significant personality changes may emerge, and affected individuals need extensive help with daily activities. At this stage, individuals may:<br>Lose most awareness of recent experiences and events as well as of their surroundings.<br>Recollect their personal history imperfectly, although they generally recalltheir own name.<br>Occasionally forget the name of their spouse or primary caregiver but generally can distinguish familiar from unfamiliar faces.<br>Need help getting dressed properly; without supervision, may make such errors as putting pajamas over daytime clothes or shoes on wrong feet.<br>Experience disruption of their normal sleep/waking cycle.<br>Need help with handling details of toileting (flushing toilet, wiping and disposing of tissue properly).<br>Have increasing episodes of urinary or fecal incontinence.<br>Experience significant personality changes and behavioral symptoms, including suspiciousness and delusions (for example, believing that their caregiver is an impostor); hallucinations (seeing or hearing things that are not really there); or compulsive, repetitive behaviors such as hand-wringing or tissue shredding.<br>Tend to wander and become lost. |

TABLE 3-continued

| Illustrative stages of Alzheimer's disease. |
|---|
| Very severe cognitive decline (Severe or late-stage Alzheimer's disease) |
| This is the final stage of the disease when individuals lose the ability to respond to their environment, the ability to speak, and, ultimately, the ability to control movement.<br>Frequently individuals lose their capacity for recognizable speech, although words or phrases may occasionally be uttered.<br>Individuals need help with eating and toileting and there is general incontinence.<br>Individuals lose the ability to walk without assistance, then the ability to sit without support, the ability to smile, and the ability to hold their head up.<br>Reflexes become abnormal and muscles grow rigid.<br>Swallowing is impaired. |

In various embodiments, administration of one or more agents described herein to subjects diagnosed with Alzheimer's disease is deemed effective when the there is a reduction in the CSF of levels of one or more components selected from Tau, phospho-Tau (pTau), APPneo, soluble Aβ40, soluble Aβ42, and/or and Aβ42/Aβ40 ratio, and/or when there is a reduction of the plaque load in the brain of the subject, and/or when there is a reduction in the rate of plaque formation in the brain of the subject, and/or when there is an improvement in the cognitive abilities of the subject, and/or when there is a perceived improvement in quality of life by the subject, and/or when there is a significant reduction in clinical dementia rating of the subject, and/or when the rate of increase in clinical dementia rating is slowed or stopped and/or when the progression of AD is slowed or stopped (e.g., when the transition from one stage to another as listed in Table 3 is slowed or stopped).

In certain embodiments, subjects amenable to the present methods generally are free of a neurological disease or disorder other than Alzheimer's disease. For example, in certain embodiments, the subject does not have and is not at risk of developing a neurological disease or disorder such as Huntington's Disease, and/or Parkinson's disease, and/or schizophrenia, and/or psychosis.

In various embodiments, the effectiveness of treatment can be determined by comparing a baseline measure of a parameter of disease before administration of the allosteric BACE inhibitor(s) and/or formulation(s) thereof is commenced to the same parameter one or more time points after the compound/formulation has been administered. One illustrative, but non-limiting, parameter that can be measured is a biomarker (e.g., a peptide oligomer) of APP processing. Such biomarkers include, but are not limited to increased levels of sAPPβ, p3 (Aβ 17-42 or Aβ 17-40), βAPPβ, soluble Aβ40, and/or soluble Aβ42 in the blood, plasma, serum, urine, mucous or cerebrospinal fluid. Detection of increased levels of sAPPα and/or p3, and decreased levels of βAPPβ and/or APPneo is an indicator that the treatment is effective. Conversely, detection of decreased levels of sAPPα and/or p3, and/or increased levels of βAPPβ, APPneo, Tau or phospho-Tau (pTau) is an indicator that the treatment is not effective.

Another parameter to determine effectiveness of treatment is the level of amyloid plaque deposits in the brain. Amyloid plaques can be determined using any method known in the art, e.g., as determined by CT, PET, PIB-PET and/or MM.

In various embodiments, administration of the allosteric BACE inhibitor(s) described herein can result in a reduction in the rate of plaque formation, and even a retraction or reduction of plaque deposits in the brain. Effectiveness of treatment can also be determined by observing a stabilization and/or improvement of cognitive abilities of the subject. Cognitive abilities can be evaluated using any art-accepted method, including for example, Clinical Dementia Rating, the mini-mental state examination (MMSE) or Folstein test, evaluative criteria listed in the DSM-IV (Diagnostic and Statistical Manual of Mental Disorders, Fourth Edition) or DSM-V, and the like.

In certain embodiments, the monitoring methods can entail determining a baseline value of a measurable biomarker or parameter (e.g., amyloid plaque load or cognitive abilities) in a subject before administering a dosage of the multi-component formulation and optionally one or more pharmaceuticals, and comparing this biomarker or parameter with a value for the same measurable biomarker or parameter after treatment.

In other methods, a control value (e.g., a mean and standard deviation) of the measurable biomarker or parameter is determined for a control population. In certain embodiments, the individuals in the control population have not received prior treatment and do not have AD, MCI, nor are at risk of developing AD or MCI. In such cases, if the value of the measurable biomarker or clinical parameter approaches the control value, then treatment is considered efficacious. In other embodiments, the individuals in the control population have not received prior treatment and have been diagnosed with AD or MCI. In such cases, if the value of the measurable biomarker or clinical parameter approaches the control value, then treatment is considered inefficacious.

In other methods, a subject who is not presently receiving treatment but has undergone a previous course of treatment is monitored for one or more of the biomarkers or clinical parameters to determine whether a resumption of treatment is required. The measured value of one or more of the biomarkers or clinical parameters in the subject can be compared with a value previously achieved in the subject after a previous course of treatment. Alternatively, the value measured in the subject can be compared with a control value (mean plus standard deviation/ANOVA) determined in population of subjects after undergoing a course of treatment. Alternatively, the measured value in the subject can be compared with a control value in populations of prophylactically treated subjects who remain free of symptoms of disease, or populations of therapeutically treated subjects who show amelioration of disease characteristics. In such cases, if the value of the measurable biomarker or clinical parameter approaches the control value, then treatment is considered efficacious and need not be resumed. In all of these cases, a significant difference relative to the control level (e.g., more than a standard deviation) is an indicator that treatment should be resumed in the subject.

In various embodiments, the tissue sample for analysis is typically blood, plasma, serum, urine, mucous or cerebrospinal fluid from the subject.

Pharmaceutical Formulations.

In certain embodiments, one or more allosteric BACE inhibitor(s) described herein or an enantiomer, a mixture of enantiomers, or a mixture of two or more diastereomers thereof, a pharmaceutically acceptable salt, ester, amide, solvate, hydrate, prodrug thereof or derivative thereof) are administered to a mammal in need thereof, e.g., to a mammal at risk for or suffering from a neurodegenerative pathology including, but not limited to a pathology characterized by abnormal processing of amyloid precursor proteins (e.g., amyloidogenic MCI, Alzheimer's disease, etc.), a mammal at risk for progression from a pre-symptomatic condition to a symptomatic condition (e.g., from an asymptomatic condition to MCI, from an asymptomatic condition to AD, from MCI to AD, and the like).

The allosteric BACE inhibitor(s) described herein can be administered in the "native" form or, if desired, in the form of salts, esters, amides, prodrugs, derivatives, and the like, provided the salt, ester, amide, prodrug or derivative is suitable pharmacologically, e.g., effective in the present method(s). Salts, esters, amides, prodrugs and other derivatives of the allosteric BACE inhibitor(s) can be prepared using standard procedures known to those skilled in the art of synthetic organic chemistry and described, for example, by March (1992) Advanced Organic Chemistry; Reactions, Mechanisms and Structure, 4th Ed. N.Y. Wiley-Interscience.

Methods of formulating such derivatives are known to those of skill in the art. For example, a pharmaceutically acceptable salt can be prepared for any compound described herein having a functionality capable of forming a salt (e.g., such as a carboxylic acid functionality of the compounds described herein). A pharmaceutically acceptable salt is any salt that retains the activity of the parent compound and does not impart any deleterious or untoward effect on the subject to which it is administered and in the context in which it is administered.

Methods of pharmaceutically formulating the compounds described herein as salts, esters, amide, prodrugs, and the like are well known to those of skill in the art. For example, salts can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the compounds described herein can include halide salts, such as may be prepared using hydrochloric or hydrobromic acids. Conversely, preparation of basic salts of the allosteric BACE inhibitor(s) described herein can be prepared in a similar manner using a pharmaceutically acceptable base such as sodium hydroxide, potassium hydroxide, ammonium hydroxide, calcium hydroxide, trimethylamine, or the like. In certain embodiments basic salts include alkali metal salts, e.g., the sodium salt, and copper salts.

For the preparation of salt forms of basic drugs, the pKa of the counterion is preferably at least about 2 pH units lower than the pKa of the drug. Similarly, for the preparation of salt forms of acidic drugs, the pKa of the counterion is preferably at least about 2 pH units higher than the pKa of the drug. This permits the counterion to bring the solution's pH to a level lower than the pHmax to reach the salt plateau, at which the solubility of salt prevails over the solubility of free acid or base. The generalized rule of difference in pKa units of the ionizable group in the active pharmaceutical ingredient and in the acid or base is meant to make the proton transfer energetically favorable. When the pKa of the API and counterion are not significantly different, a solid complex may form but may rapidly disproportionate (e.g., break down into the individual entities of drug and counterion) in an aqueous environment.

In various embodiments, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, formate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

Preparation of esters typically involves functionalization of hydroxyl and/or carboxyl groups that are present within the molecular structure of the active agent (e.g., allosteric BACE inhibitor. In certain embodiments, the esters are typically acyl-substituted derivatives of free alcohol groups, e.g., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

In various embodiments, the compounds identified herein are useful for parenteral, topical, oral, nasal (or otherwise inhaled), rectal, or local administration, such as by aerosol or transdermally, for prophylactic and/or therapeutic treatment of one or more of the pathologies/indications described herein (e.g., amyloidogenic pathologies).

The active agent(s) described herein (e.g., a allosteric BACE inhibitor, and/or an enantiomer, a mixture of enantiomers, or a mixture of two or more diastereomers thereof; or a pharmaceutically acceptable salt, ester, amide, solvate, hydrate, or prodrug thereof or derivatives thereof) can also be combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the allosteric BACE inhibitor(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the allosteric BACE inhibitor(s), or excipients or other stabilizers and/or buffers.

Other physiologically acceptable compounds, particularly of use in the preparation of tablets, capsules, gel caps, and the like include, but are not limited to binders, diluent/fillers, disintegrants, lubricants, suspending agents, and the like.

In certain embodiments, to manufacture an oral dosage form (e.g., a tablet), an excipient (e.g., lactose, sucrose, starch, mannitol, etc.), an optional disintegrator (e.g., calcium carbonate, carboxymethylcellulose calcium, sodium starch glycollate, crospovidone etc.), a binder (e.g., alpha-starch, gum arabic, microcrystalline cellulose, carboxymethylcellulose, polyvinylpyrrolidone, hydroxypropylcellulose, cyclodextrin, etc.), and an optional lubricant (e.g., talc, magnesium stearate, polyethylene glycol 6000, etc.), for instance, are added to the active component or components (e.g., allosteric BACE inhibitor described herein or a formulation thereof, and/or an enantiomer, a mixture of enantiomers, or a mixture of two or more diastereomers thereof, a pharmaceutically acceptable salt, ester, amide, solvate, hydrate, prodrug thereof or derivatives thereof) and the resulting composition is compressed. Where necessary the compressed product is coated, e.g., known methods for masking the taste or for enteric dissolution or sustained release. Suitable coating materials include, but are not limited to ethyl-cellulose, hydroxymethylcellulose, polyoxyethylene glycol, cellulose acetate phthalate, hydroxypropylmethylcellulose phthalate, and Eudragit (Rohm & Haas, Germany; methacrylic-acrylic copolymer).

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the allosteric BACE inhibitor(s) described herein and on the particular physiochemical characteristics of the allosteric BACE inhibitor(s).

In certain embodiments, the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectable, implantable sustained-release formulations, mucoadherent films, topical varnishes, lipid complexes, etc.

Pharmaceutical compositions comprising the allosteric BACE inhibitor(s) described herein can be manufactured by means of conventional mixing, dissolving, granulating, dragee-making, levigating, emulsifying, encapsulating, entrapping or lyophilizing processes. Pharmaceutical compositions can be formulated in a conventional manner using one or more physiologically acceptable carriers, diluents, excipients or auxiliaries that facilitate processing of the allosteric BACE inhibitor(s) into preparations that can be used pharmaceutically. Proper formulation is dependent upon the route of administration chosen.

For topical administration the allosteric BACE inhibitor (s) described herein can be formulated as solutions, gels, ointments, creams, suspensions, and the like as are well-known in the art. Systemic formulations include, but are not limited to, those designed for administration by injection, e.g., subcutaneous, intravenous, intramuscular, intrathecal or intraperitoneal injection, as well as those designed for transdermal, transmucosal oral or pulmonary administration. For injection, the allosteric BACE inhibitor(s) described herein can be formulated in aqueous solutions, preferably in physiologically compatible buffers such as Hanks solution, Ringer's solution, or physiological saline buffer and/or in certain emulsion formulations. The solution can contain formulatory agents such as suspending, stabilizing and/or dispersing agents. In certain embodiments, the allosteric BACE inhibitor(s) can be provided in powder form for constitution with a suitable vehicle, e.g., sterile pyrogen-free water, before use. For transmucosal administration, penetrants appropriate to the barrier to be permeated can be used in the formulation. Such penetrants are generally known in the art.

For oral administration, the compounds can be readily formulated by combining the allosteric BACE inhibitor(s) with pharmaceutically acceptable carriers well known in the art. Such carriers enable the compounds described herein to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone; granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like can be added. For buccal administration, the compositions may take the form of tablets, lozenges, etc. formulated in conventional manner.

For administration by inhalation, the compound(s) described herein are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

In various embodiments, the compound(s) described herein can be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations can be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems can be employed. Liposomes and emulsions are well known examples of delivery vehicles that may be used to protect and deliver pharmaceutically active compounds. Certain organic solvents such as dimethylsulfoxide also can be employed, although usually at the cost of greater toxicity. Additionally, the compounds may be delivered using a sustained-release system, such as semipermeable matrices of solid polymers containing the therapeutic agent. Various uses of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

In certain embodiments, the compound(s) and/or formulations described herein are administered orally. This is readily accomplished by the use of tablets, caplets, lozenges, liquids, and the like.

In certain embodiments, the compound(s) and/or formulations described herein are administered systemically (e.g., orally, or as an injectable) in accordance with standard methods well known to those of skill in the art. In other embodiments, the agents can also be delivered through the skin using conventional transdermal drug delivery systems, e.g., transdermal "patches" wherein the compound(s) and/or formulations described herein are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one illustrative embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the allosteric BACE inhibitor(s) and any other materials that are present.

In certain embodiments, one or more allosteric BACE inhibitor(s) described herein can be provided as a "concentrate", e.g., in a storage container (e.g., in a premeasured volume) ready for dilution, or in a soluble capsule ready for addition to a volume of water, alcohol, hydrogen peroxide, or other diluent.

In certain embodiments, the allosteric BACE inhibitor(s) herein are suitable for oral administration. In various embodiments, the compound(s) in the oral compositions can be either coated or non-coated. The preparation of enteric-coated particles is disclosed for example in U.S. Pat. Nos. 4,786,505 and 4,853,230.

In various embodiments, compositions contemplated herein typically comprise one or more of the various allosteric BACE inhibitor(s) described herein in an effective amount to achieve a pharmacological effect or therapeutic improvement without undue adverse side effects. Various effects deemed therapeutic are described above. Illustrative pharmacological effects or therapeutic improvements include, but are not limited to a reduction in the CSF of levels of one or more components selected from Tau, phospho-Tau (pTau), APPneo, soluble Aβ 40 and soluble Aβ 42, and/or when a reduction of the plaque load in the brain of the subject, and/or a reduction in the rate of plaque formation in the brain of the subject, and/or an improvement in the cognitive abilities of the subject, and/or a perceived improvement in quality of life by the subject, and/or a significant reduction in clinical dementia rating of the subject, and/or a slowing in the rate of increase in clinical dementia rating, and/or when a slowing or stopping in the progression of AD (e.g., when the transition from one stage to another as listed in Table 3 is slowed or stopped).

The active ingredients are preferably formulated in a single oral dosage form containing all active ingredients. Such oral formulations include solid and liquid forms. It is noted that solid formulations typically provide improved stability as compared to liquid formulations and can often afford better patient compliance.

In one illustrative embodiment, the one or more of the various compound(s) described herein are formulated in a single solid dosage form such as single- or multi-layered tablets, suspension tablets, effervescent tablets, powder, pellets, granules or capsules comprising multiple beads as well as a capsule within a capsule or a double chambered capsule. In another embodiment, the compound(s) described herein may be formulated in a single liquid dosage form such as suspension containing all active ingredients or dry suspension to be reconstituted prior to use.

In certain embodiments, the compound(s) are formulated as enteric-coated delayed-release granules or as granules coated with non-enteric time-dependent release polymers in order to avoid contact with the gastric juice. Non-limiting examples of suitable pH-dependent enteric-coated polymers are: cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures of any of the foregoing. A suitable commercially available enteric material, for example, is sold under the trademark EUDRAGIT L 100-55®. This coating can be spray coated onto a substrate.

Illustrative non-enteric-coated time-dependent release polymers include, for example, one or more polymers that swell in the stomach via the absorption of water from the gastric fluid, thereby increasing the size of the particles to create thick coating layer. The time-dependent release coating generally possesses erosion and/or diffusion properties that are independent of the pH of the external aqueous medium. Thus, the active ingredient is slowly released from the particles by diffusion or following slow erosion of the particles in the stomach.

Illustrative non-enteric time-dependent release coatings are for example: film-forming compounds such as cellulosic derivatives, such as methylcellulose, hydroxypropyl methylcellulose (HPMC), hydroxyethylcellulose, and/or acrylic polymers including the non-enteric forms of the EUDRAGIT® brand polymers. Other film-forming materials can be used alone or in combination with each other or with the ones listed above. These other film forming materials generally include, for example, poly(vinylpyrrolidone), Zein, poly(ethylene glycol), poly(ethylene oxide), poly(vinyl alcohol), poly(vinyl acetate), and ethyl cellulose, as well as other pharmaceutically acceptable hydrophilic and hydrophobic film-forming materials. These film-forming materials may be applied to the substrate cores using water as the vehicle or, alternatively, a solvent system. Hydro-alcoholic systems may also be employed to serve as a vehicle for film formation.

Other materials suitable for making the time-dependent release coating of the compounds described herein include, by way of example and without limitation, water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as hydroxymethylcellulose, hydroxyethylcellulose, and hydroxypropylcellulose; synthetic water-soluble cellulose-based lamina formers such as methyl cellulose and its hydroxyalkyl methylcellulose cellulose derivatives such as a member selected from hydroxyethyl methylcellulose, hydroxypropyl methylcellulose, and hydroxybutyl methylcellulose; other cellulose polymers such as sodium carboxymethylcellulose; and other materials known to those of ordinary skill in the art. Other lamina forming materials that can be used for this purpose include, but are not limited to poly(vinylpyrrolidone), polyvinylalcohol, polyethylene oxide, a blend of gelatin and polyvinyl-pyrrolidone, gelatin, glucose, saccharides, povidone, copovidone, poly(vinylpyrrolidone)-poly(vinyl acetate) copolymer.

While the compositions and methods are described herein with respect to use in humans, they are also suitable for animal, e.g., veterinary use. Thus certain illustrative organisms include, but are not limited to humans, non-human primates, canines, equines, felines, porcines, ungulates, largomorphs, and the like.

The foregoing formulations and administration methods are intended to be illustrative and not limiting. It will be appreciated that, using the teaching provided herein, other suitable formulations and modes of administration can be readily devised.

Deformable Nanoscale Drug Delivery Vehicle(s).

In certain embodiments the allosteric BACE inhibitors and/or metformin, and/or proguanil, and/or TPPU, and/or sAPPα are provided as a formulation comprising a deformable nanoscale vesicle(s) (DNV(s)), e.g., as described in International Application No: PCT/US2016/062552, filed on Nov. 27, 2016, which is incorporated herein by reference for the DNVs described therein.

In various embodiments the DNVs described herein are capable of crossing the blood-brain barrier and can be used to deliver a cargo (e.g., one or more allosteric BACE inhibitors and/or metformin, and/or proguanil, and/or TPPU, and/or sAPPα) to the brain/CNS. Such delivery across the blood-brain barrier can be accomplished by administration of the DNVs according to any of a number of modalities including, but not limited to, aerosol administration including nasal inhalation, oral inhalation, and the like, oral delivery, isophoretic delivery, subdermal delivery, transdermal delivery, parenteral delivery, intravenous administration, intra-arterial administration, depot delivery, and rectal administration.

In certain embodiments the DNVs are provided in transdermal patches for delivery of cargo across the blood-brain barrier to the central nervous system. In addition to methods of synthesizing the DNVs themselves, transdermal patches loaded with CNS-targeted DNVs for delivery of cargo (drugs, proteins, antibodies, RNA or DNA) to the brain are provided.

In certain embodiments the DNVs can be provided as patch, capsule, liquid (and the like) for non-CNS localized delivery of DNVs. In some cases, very localized non-CNS delivery is required for effective treatment, with avoidance of systemic distribution of DNVs. DNVs with increased charge and therefore restricted distribution can be synthesized.

In various embodiments the DNVs comprise one or more vesicle-forming lipids, generally including amphipathic lipids having both hydrophobic tail groups and polar head groups, cholesterol, and a detergent. A characteristic of a vesicle-forming lipid is its ability to either (a) form spontaneously into bilayer vesicles in water, as exemplified by the phospholipids, or (b) be stably incorporated into lipid bilayers, by having the hydrophobic portion in contact with the interior, hydrophobic region of the bilayer membrane, and the polar head group oriented toward the exterior, polar surface of the membrane. In certain embodiments a vesicle-forming lipid for use in the DNVs may include any conventional lipid possessing one of the characteristics described above.

In certain embodiments the vesicle-forming lipids of this type are those having two hydrocarbon tails or chains, typically acyl groups, and a polar head group. Included in this class are the phospholipids, such as phosphatidylcholine, phosphatidylethanolamine, phosphatidic acid, phosphatidylglycerol, and phosphatidylinositol, where the two hydrocarbon chains are typically between about 14-22 carbon atoms in length, and have varying degrees of unsaturation. In certain embodiments suitable phospholipids include PE and PC. One illustrative PC is hydrogenated soy phosphatidylcholine (HSPC). Single chain lipids, such as sphingomyelin, and the like can also be used. In certain embodiments the phospholipids comprise one or more phospholipids such as 1,2-Dipalmitoyl-sn-glycero-3-phosphocholine (DPPC), N-(2,3-Dioleoyloxy-1-propyl) trimethylammonium (DOTAP), and/or 1,2-Dioleoyl-sn-glycero-3-phosphoethanolamine (DOPE).

The above-described lipids and phospholipids whose acyl chains have a variety of degrees of saturation can be obtained commercially or prepared according to published methods. Other lipids that can be included in certain embodiments are sphingolipids and glycolipids. The term "sphingolipid" as used herein encompasses lipids having two hydrocarbon chains, one of which is the hydrocarbon chain of sphingosine. The term "glycolipids" refers to shingolipids comprising also one or more sugar residues.

In various embodiments the DNVs additionally include lipids that can stabilize the a DNV composed predominantly of phospholipids. An illustrative lipid of this group is cholesterol at levels between 20 to 45 mole percent.

In various embodiments the DNVs, can further include a surface coating of a hydrophilic polymer chain. In certain embodiments the hydrophilic polymer can be included in the DNV by including in the DNV composition one or more lipids (e.g., phospholipids) derivatized with a hydrophilic polymer chain which can be used include, but are not limited to any of those described above, however, in certain embodiments, vesicle-forming lipids with diacyl chains, such as phospholipids, are preferred. One illustrative phospholipid is phosphatidylethanolamine, which contains a reactive amino group convenient for coupling to the activated polymers which can be coupled with targeting molecules such as transferrin, folic acid, and the like One illustrative PE is distearoyl PE (DSPE). Another example is non-phospholipid double chain amphiphilic lipids, such as diacyl- or dialkylglycerols, derivatized with a hydrophilic polymer chain.

In certain embodiments a hydrophilic polymer for use on a DNV to increase serum half life and/or for coupling an antibody or ligand is polyethyleneglycol, in certain embodiments as a PEG chain having a molecular weight between 1,000-10,000 Daltons, or between 1,000-5,000 Daltons, or preferably between 2,000-5,000 Daltons. Methoxy or ethoxy-capped analogues of PEG are also useful hydrophilic polymers, commercially available in a variety of polymer sizes, e.g., 120-20,000 Daltons.

Other hydrophilic polymers that can be suitable include, but are not limited to polylactic acid, polyglycolic acid, polyvinylpyrrolidone, polymethyloxazoline, polyethyloxazoline, polyhydroxypropyl methacrylamide, polymethacrylamide, polydimethylacrylamide, and derivatized celluloses, such as hydroxymethylcellulose or hydroxyethylcellulose.

Preparation of lipid-polymer conjugates containing these polymers attached to a phospholipid have been described, for example in U.S. Pat. No. 5,395,619. In certain embodiments, typically, between about 0.1-20 mole percent of the polymer-derivatized lipid is included in the liposome-forming components during liposome formation. Polymer-derivatized lipids are also commercially available (e.g. SUNBRITE®, NOF Corporation, Japan).

In various embodiments the hydrophilic polymer chains provide a surface coating of hydrophilic chains sufficient to extend the blood circulation time of the DNVs in the absence of such a coating.

In one illustrative an non-limiting embodiment, the lipids (including cholesterol) and the edge activator are present in an 85:15 w/w ratio.

The exact molar ratio and types of lipid components used are determined based on the intended application of the DNVs. For example, for trans-oral mucosal and transdermal topical application, in one illustrative, but non-limiting embodiment, a 5:3:2 molar ratio (DPPC:Cholesterol:DOTAP) is used, with the mixture containing 15% Span 80 by weight.

These components, dissolved in an organic solvent such as isopropyl alcohol can be combined with aqueous solution (PBS or DI water) via separate inputs into a microfluidic reactor system for efficient and continuous synthesis at a temperature ranging from 25° C. to 40° C. and 1 bar pressure. The microfluidic reactor channels provide high shear stress and controlled mixing, with minimized turbulence, resulting in well-defined DNV populations, and eliminating the need for post-processing such as sonication or extrusion to obtain appropriate or uniform size. Upon transitioning from organic to aqueous phase, the components described self-configure into DNVs, according to their thermodynamic stability in aqueous solvent. They are non-toxic, prepared with high reproducibly with little batch to batch variability, scalable, very homogenous in population and distribution, of tunable size, and provide highly localized payload delivery. Our research shows that this method can produce homogenous DNV populations with sizes from 50 nm to the micron range.

In certain embodiments the DNVs range in size from about 50 nm up, or from about 60 nm, or from about 70 nm, or from about 80 nm, or from about 90 nm, or from about 100 nm, up to about 10 μm, or up to about 5 μm, or up to about 1 μm, or up to about 900 nm, or up to about 800 nm, or up to about 700 nm, or up to about 600 nm, or up to about 500 nm, or up to about 400 nm, or up to about 300 nm average diameter. In certain embodiments the DNVs range in size from about 50 nm up to about 275 nm average diameter. In certain embodiments the DNVs are about 50 nm average diameter, or about 100 nm average diameter, or about 150 nm average diameter, or about 200 nm average diameter or about 250 nm average diameter.

Resultant DNV size can be tuned primarily by the adjustment of the flow rate ratio between the aqueous phase and the organic, lipid containing, phase. Our investigations have shown that increasing the flow rate ratio directly decreases resultant DNV size as well as reducing size variability. For trans-oral mucosal and topical application, a FRR of 100 can be used, to obtain DNVs with a size centered at 250 nm from the aforementioned components. Note that the same FRR may produce different sized DNVs, depending on the particular types of components used.

In certain embodiments the charge on the DNV can be tuned/varied as desired. The charge on the DNVs will, in part, determine the degree of dispersion from the application site. DNVs of various charge concentrations (zeta potentials) can be created through the use of different combinations of charged phospholipid components. We have synthesized neutral (DPPC, cholesterol, DOPE), cationic (DPPC, cholesterol, DOTAP) and anionic (DPPC, cholesterol, DHP) DNVs. The amount of charge can be tuned by adjusting the concentration of a particular charged component in the DNV preparation mixture. By tuning charge, DNV delivery can be restricted to local delivery or permitted to allow systemic delivery.

In addition to size, cargo, deformability, and charge the half-life of DNVs can be increased by additional of polyethylene glycol (PEG) or other polymers. Depending upon the therapeutic goal, addition of PEG is an option.

In addition to cargo, size, and deformability, DNVs may be synthesized that are "decorated" on the exterior with targeting agents such as, but not limited to, transferrin or folic acid to allow targeting of cells that express transferrin (or folic acid receptors, respectively. These receptors are often expressed on the BBB or tumor cells and therefore DNV with these targeting agents could bind and cross the BBB and these cells can be targeted. Other cell types may specifically be targeted by use of other ligands on the DNV surface.

Generally, the targeting agents can associate with any target of interest, such as a target associated with an organ, tissues, cell, extracellular matrix or intracellular region. In certain embodiments, a target can be associated with a particular disease state, amyloid plaque deposition, or tissue necrosis. In some embodiments, the targeting agent can be specific to only one target, such as a receptor. Suitable targets can include, but are not limited to, a nucleic acid, such as a DNA, RNA, or modified derivatives thereof. Suitable targets can also include, but are not limited to, a protein, such as an extracellular protein, a receptor, a cell surface receptor, a tumor-marker, a transmembrane protein, an enzyme or an antibody. Suitable targets can include a carbohydrate, such as a monosaccharide, disaccharide or polysaccharide that can be, for example, present on the surface of a cell.

In certain embodiments, a targeting agent can include a target ligand, a small molecule mimic of a target ligand (e.g., a peptide mimetic ligand), or an antibody or antibody fragment specific for a particular target. In some embodiments, a targeting agent can further include folic acid derivatives, B-12 derivatives, integrin RGD peptides, NGR derivatives, somatostatin derivatives or peptides that bind to the somatostatin receptor, e.g., octreotide and octreotate, and the like. In certain embodiments the targeting agents can also include an aptamer. Aptamers can be designed to associate with or bind to a target of interest. Aptamers can be comprised of, for example, DNA, RNA and/or peptides, and certain aspects of aptamers are well known in the art (see, e.g., Klussman, S., Ed., The Aptamer Handbook, Wiley-VCH (2006); Nissenbaum (2008) Trends in Biotech. 26(8): 442-449; and the like).

In certain embodiments the DNV is attached to a ligand or antibody that binds to a cell surface marker. In certain embodiments the marker is a neural cell marker.

Methods of coupling lipid-containing constructs and targeting agents are well known to those of skill in the art. Examples include, but are not limited to the use of biotin and avidin or streptavidin (see, e.g., U.S. Pat. No. 4,885,172 A), by traditional chemical reactions using, for example, bifunctional coupling agents such as glutaraldehyde, diimide esters, aromatic and aliphatic diisocyanates, bis-p-nitrophenyl esters of dicarboxylic acids, aromatic disulfonyl chlorides and bifunctional arylhalides such as 1,5-difluoro-2,4-dinitrobenzene; p,p'-difluoro m,m'-dinitrodiphenyl sulfone, sulfhydryl-reactive maleimides, and the like. Appropriate reactions which may be applied to such couplings are described in Williams et al. Methods in Immunology and Immunochemistry Vol. 1, Academic Press, New York 1967.

Methods of manufacturing such DNVs are known to those of skill in the art, and described, inter alia, in PCT/US2016/062552. For example, in certain embodiments, the DNVs can be prepared in a microfluidic reactor by combining building blocks in organic and aqueous phases at a precisely controlled flow rate ratio, e.g., at room temperature and pressure, providing high shear stress at a fast rate and controlled mixing in micro-channels, reducing turbulence and minimizing the size and dispersity of the resultant DNVs.

Combined Treatment Methods and Combined Formulations

In certain instances, one or more of the allosteric BACE inhibitors described herein (or formulation, and/or an enantiomer, a mixture of enantiomers, or a mixture of two or more diastereomers thereof, a pharmaceutically acceptable salt, ester, amide, solvate, hydrate, prodrug thereof or derivative thereof) are administered in conjunction with one or more additional active agent(s) that are known, or believed, to have utility in the treatment of neurodegenerative diseases including, but not limited to Alzheimer's disease, age-related cognitive impairment, MCI, and the like. The two agents (e.g., an allosteric BACE inhibitor described herein and additional agent) can be administered simultaneously or sequentially. When administered sequentially the two agents are typically administered so that both achieve a physiologically relevant concentration and/or effect over a similar time period (e.g., so that both agents are active at some common time).

In certain instances, one or more of the allosteric BACE inhibitor(s) described herein (or formulation, and/or an enantiomer thereof, a mixture of enantiomers, or a mixture of two or more diastereomers thereof, and/or a pharmaceutically acceptable salt, ester, amide, solvate, hydrate, or prodrug thereof or derivative thereof) are administered before the one or more additional active agent(s) or they are administered after the one or more additional active agent(s). In certain embodiments one or more of the allosteric BACE inhibitor(s) described herein (or a formulation, and/or an enantiomer thereof, a mixture of enantiomers, or a mixture of two or more diastereomers thereof, and/or a pharmaceutically acceptable salt, ester, amide, solvate, hydrate, or prodrug thereof or derivative thereof) are administered simultaneously with one or more additional active agent(s) and in such instances may be formulated as a compound formulation.

Suitable additional active agent(s) include, but are not limited to, Donepezil (e.g., Aricept), Rivastigmine (e.g., EXELON®), Galantamine (e.g., RAZADINE®), Tacrine (e.g., COGNEX®), Memantine (e.g., NAMENDA®), NAMZARIC, Solanezumab, Bapineuzumab, Alzemed, Flurizan, ELND005, Valproate, Semagacestat, Rosiglitazone, Phenserine, Cernezumab, Dimebon, EGCg, Gammagard, PBT2, PF04360365, NIC5-15, Bryostatin-1, AL-108, Nicotinamide, EHT-0202, BMS708163, NP12, Lithium, ACC001, AN1792, ABT089, NGF, CAD106, AZD3480, SB742457, AD02, Huperzine-A, EVP6124, PRX03140, PUFA, HF02, MEM3454, TTP448, PF-04447943, Ent., GSK933776, MABT5102A, Talsaclidine, UB311, Begacestat, R1450, PF3084014, V950, E2609, MK0752, CTS21166, AZD-3839, AZD-3293, LY2886721, LY2811376, CHF5074, verubecestat (MK-8931), NB-360, CNP520, JNJ-54861911, R 05508887, anti-inflammatories (e.g., Flurizan (Myriad Genetics), Dapsone, anti-TNF antibodies (e.g., etanercept (Amgen/Pfizer)), and the like, statins (e.g., atorvastatin (LIPITOR®), simvastatin (ZOCOR®, etc.), BACE inhibitors and the like. In certain embodiments, treatment methods comprising administration of one or more allosteric BACE inhibitor(s) described herein in conjunction with any one of the foregoing additional active agent(s) is contemplated.

In certain embodiments, treatment methods comprising administration of one or more allosteric BACE inhibitor(s) described herein (or a formulation, and/or an enantiomer thereof, a mixture of enantiomers, or a mixture of two or more diastereomers thereof, and/or a pharmaceutically acceptable salt, ester, amide, solvate, hydrate, or prodrug thereof or derivative thereof) in conjunction with additional therapeutic agents such as disulfiram and/or analogues thereof, honokiol and/or analogues thereof, tropisetron and/or analogues thereof, nimetazepam and/or analogues thereof (e.g., as described in U.S. Ser. No. 13/213,960 (U.S. Patent Publication No: US-2012-0071468-A1), and PCT/US2011/048472 (PCT Publication No: WO 2012/024616) which are incorporated herein by reference for the compounds described therein) are contemplated. In certain embodiments the treatment method comprises administration of tropisetron in conjunction with of one or more allosteric BACE inhibitor(s) described herein.

In certain embodiments, combination formulations comprising one or more allosteric BACE inhibitor(s) described herein in combination with additional therapeutic agents such as disulfiram and/or analogues thereof, honokiol and/or analogues thereof, tropisetron and/or analogues thereof, nimetazepam and/or analogues thereof (e.g., as described in U.S. Ser. No. 13/213,960 (U.S. Patent Publication No: US-2012-0071468-A1), and PCT/US2011/048472 (PCT Publication No: WO 2012/024616) which are incorporated herein by reference for the compounds described therein) are contemplated. In certain embodiments the combination formulation comprises a allosteric BACE inhibitor(s) in combination with tropisetron and/or of one or more tropinol esters, related esters, derivatives thereof, analogs thereof, polymorphs thereof (e.g. as described in PCT/US2012/049223), and the like is contemplated.

Kits.

In various embodiments the active agents described herein (e.g., allosteric BACE inhibitors) can be provided in kits. In certain embodiments the kits comprise the active agent(s) described herein enclosed in multiple or single dose containers. In certain embodiments the kits can comprises component parts that can be assembled for use. For example, an active agent in lyophilized form and a suitable diluent may be provided as separated components for combination prior to use. A kit may include an active agent and a second therapeutic agent for co-administration. The active agent and second therapeutic agent may be provided as separate component parts. A kit may include a plurality of containers, each container holding one or more unit dose of the compounds. The containers are preferably adapted for the desired mode of administration, including, but not limited to tablets, gel capsules, sustained-release capsules, and the like for oral administration; depot products, pre-filled syringes, ampules, vials, and the like for parenteral administration; and patches, medipads, creams, and the like for topical administration, e.g., as described herein.

In certain embodiments the kits can further comprise instructional/informational materials. In certain embodiments the informational material(s) indicate that the administering of the compositions can result in adverse reactions including but not limited to allergic reactions such as, for example, anaphylaxis. The informational material can indicate that allergic reactions may exhibit only as mild pruritic rashes or may be severe and include erythroderma, vasculitis, anaphylaxis, Steven-Johnson syndrome, and the like. In certain embodiments the informational material(s) may indicate that anaphylaxis can be fatal and may occur when any foreign substance is introduced into the body. In certain embodiments the informational material may indicate that these allergic reactions can manifest themselves as urticaria or a rash and develop into lethal systemic reactions and can occur soon after exposure such as, for example, within 10 minutes. The informational material can further indicate that an allergic reaction may cause a subject to experience paresthesia, hypotension, laryngeal edema, mental status changes, facial or pharyngeal angioedema, airway obstruction, bronchospasm, urticaria and pruritus, serum sickness, arthritis, allergic nephritis, glomerulonephritis, temporal arthritis, eosinophilia, or a combination thereof.

While the instructional materials typically comprise written or printed materials they are not limited to such. Any medium capable of storing such instructions and communicating them to an end user is contemplated herein. Such media include but are not limited to electronic storage media (e.g., magnetic discs, tapes, cartridges, chips), optical media (e.g., CD ROM), and the like. Such media may include addresses to internet sites that provide such instructional materials.

In some embodiments, the kits can comprise one or more packaging materials such as, for example, a box, bottle, tube, vial, container, sprayer, insufflator, intravenous (I.V.) bag, envelope, and the like, and at least one unit dosage form of an agent comprising active agent(s) described herein and a packaging material. In some embodiments, the kits also include instructions for using the composition as prophylactic, therapeutic, or ameliorative treatment for the disease of concern.

In some embodiments, the articles of manufacture can comprise one or more packaging materials such as, for example, a box, bottle, tube, vial, container, sprayer, insufflator, intravenous (I.V.) bag, envelope, and the like; and a first composition comprising at least one unit dosage form of an agent comprising one or more allosteric BACE inhibitor (s) described herein within the packaging material.

Definitions

An "allosteric inhibitor" typically binds to other sites (than the native ligand (e.g., agonist) site) on the target (e.g., BACE) or they may interact at unique binding sites not normally involved in the biological regulation of the target's activity.

The terms "subject," "individual," and "patient" may be used interchangeably and typically a mammal, in certain embodiments a human or a non-human primate. While the compositions and methods are described herein with respect to use in humans, they are also suitable for animal, e.g., veterinary use. Thus, certain illustrative organisms include, but are not limited to humans, non-human primates, canines, equines, felines, porcines, ungulates, lagomorphs, and the like. Accordingly, certain embodiments contemplate the compositions and methods described herein for use with domesticated mammals (e.g., canine, feline, equine), laboratory mammals (e.g., mouse, rat, rabbit, hamster, guinea pig), and agricultural mammals (e.g., equine, bovine, porcine, ovine), and the like. The term "subject" does not require one to have any particular status with respect to a hospital, clinic, or research facility (e.g., as an admitted patient, a study participant, or the like). Accordingly, in various embodiments, the subject can be a human (e.g., adult male, adult female, adolescent male, adolescent female, male child, female child) under the care of a physician or other health worker in a hospital, psychiatric care facility, as an outpatient, or other, clinical context. In certain embodiments, the subject may not be under the care or prescription of a physician, or other, health worker. In certain embodiments the subject may not be under the care a physician or health worker and, in certain embodiments, may self-prescribe and/or self-administer the compounds described herein.

As used herein, the phrase "a subject in need thereof" refers to a subject, as described infra, that suffers or is at a risk of suffering (e.g., pre-disposed such as genetically pre-disposed) from the diseases or conditions listed herein.

A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount is less than the therapeutically effective amount.

The terms "treatment," "treating," or "treat" as used herein, refer to actions that produce a desirable effect on the symptoms or pathology of a disease or condition, particularly those that can be effected utilizing the multi-component formulation(s) described herein, and may include, but are not limited to, even minimal changes or improvements in one or more measurable markers of the disease or condition being treated. Treatments also refers to delaying the onset of, retarding or reversing the progress of, reducing the severity of, or alleviating or preventing either the disease or condition to which the term applies, or one or more symptoms of such disease or condition. "Treatment," "treating," or "treat" does not necessarily indicate complete eradication or cure of the disease or condition, or associated symptoms thereof. In one embodiment, treatment comprises improvement of at least one symptom of a disease being treated. The improvement may be partial or complete. The subject receiving this treatment is any subject in need thereof. Exemplary markers of clinical improvement will be apparent to persons skilled in the art.

An "effective amount" refers to an amount effective, at dosages and for periods of time necessary, to achieve the desired therapeutic or prophylactic result. A "therapeutically effective amount" of compound (e.g., a BACE inhibitor) or formulation thereof described herein may vary according to factors such as the disease state, age, sex, and weight of the individual, and the ability of the treatment to elicit a desired response in the individual. A therapeutically effective amount is also one in which any toxic or detrimental effects of a treatment are substantially absent or are outweighed by the therapeutically beneficial effects. The term "therapeutically effective amount" refers to an amount of one or more active agents described herein (e.g., BACE inhibitors) or composition comprising the same that is effective to "treat" a disease or disorder in a mammal (e.g., a patient). In one embodiment, a therapeutically effective amount is an amount sufficient to improve at least one symptom associated with a neurological disorder, improve neurological function, improve cognition, or one or more markers of a neurological disease, or to enhance the efficacy of one or more pharmaceuticals administered for the treatment or prophylaxis of a neurodegenerative pathology. In certain embodiments, an effective amount is an amount sufficient alone, or in combination with a pharmaceutical agent to prevent advancement or the disease, delay progression, or to cause regression of a disease, or which is capable of reducing symptoms caused by the disease.

The term "mitigating" refers to reduction or elimination of one or more symptoms of that pathology or disease, and/or a reduction in the rate or delay of onset or severity of one or more symptoms of that pathology or disease, and/or the prevention of that pathology or disease.

As used herein, the phrases "improve at least one symptom" or "improve one or more symptoms" or equivalents thereof, refer to the reduction, elimination, or prevention of one or more symptoms of pathology or disease. Illustrative symptoms of pathologies treated, ameliorated, or prevented by the compositions (active agents) described herein (e.g., allosteric BACE inhibitors, or an enantiomer, a mixture of enantiomers, or a mixture of two or more diastereomers thereof, or a pharmaceutically acceptable salt, ester, amide, solvate, hydrate, or prodrug thereof, or derivatives thereof) include, but are not limited to, reduction, elimination, or prevention of one or more markers that are characteristic of the pathology or disease (e.g., of total-Tau (tTau), phospho-Tau (pTau), APPneo, soluble Aβ40, pTau/Ap42 ratio and tTau/Ap42 ratio, and/or an increase in the CSF of levels of one or more components selected from Aβ42/Aβ40 ratio, Aβ42/Aβ38 ratio, sAPPα, βAPPα/βAPPβ ratio, βAPPα/Aβ40 ratio, βAPPα/Aβ42 ratio, etc.) and/or reduction, stabilization or reversal of one or more diagnostic criteria (e.g., clinical dementia rating). Illustrative measures for improved neurological function include, but are not limited to the use of the mini-mental state examination (MMSE) or Folstein test (a questionnaire test that is used to screen for cognitive impairment), the General Practitioner Assessment of Cognition (GPCOG), a brief screening test for cognitive impairment described by Brodaty et al., (2002) Geriatrics Society 50(3): 530-534, and the like.

As used herein, "administer" or "administering" means to introduce, such as to introduce to a subject a compound or composition. The term is not limited to any specific mode of delivery, and can include, for example, subcutaneous delivery, intravenous delivery, intramuscular delivery, intracisternal delivery, delivery by infusion techniques, transdermal delivery, oral delivery, nasal delivery, and rectal delivery. Furthermore, depending on the mode of delivery, the administering can be carried out by various individuals, including, for example, a health-care professional (e.g., physician, nurse, etc.), a pharmacist, or the subject (i.e., self-administration).

The phrase "cause to be administered" refers to the actions taken by a medical professional (e.g., a physician), or a person prescribing and/or controlling medical care of a subject, that control and/or determine, and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like.

A "derivative" of a compound means a chemically modified compound wherein the chemical modification takes place at one or more functional groups of the compound. The derivative however, is expected to retain, or enhance, the pharmacological activity of the compound from which it is derived and/or to reduce undesired side effects of the compound when administered to a mammal.

Generally, reference to a certain element such as hydrogen or H is meant to include all isotopes of that element. For example, if an R group is defined to include hydrogen or H, it also includes deuterium and tritium. Accordingly, isotopically labeled compounds are within the scope of this invention.

In certain embodiments, as used herein, the term "substituted" refers to substitution of one or more hydrogens of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient. As used herein, the phrases "substituted with one or more . . . " or "substituted one or more times . . . " refer to a number of substituents that equals from one to the maximum number of substituents possible based on the number of available bonding sites, provided that the above conditions of stability and chemical feasibility are met.

In other preferred embodiments, the term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "alkyl" includes both branched and straight chain alkyl groups. Typical alkyl groups are methyl, ethyl, n-propyl, isopropyl, n-butyl, sec-butyl, isobutyl, tert-butyl, n-pentyl, isopentyl, n-hexyl, n-heptyl, isooctyl, nonyl, decyl, undecyl, dodecyl, tetradecyl, hexadecyl, octadecyl, eicosyl and the like.

As used herein, for example, "C0-6 alkyl" is used to mean an alkyl having 0-6 carbons—that is 0, 1, 2, 3, 4, 5 or 6 carbons in a straight or branched configuration. An alkyl having no carbon is hydrogen when the alkyl is a terminal group. An alkyl having no carbon is a direct bond when the alkyl is a bridging (connecting) group. Non-limiting examples of alkyl groups include those with 0-1 carbon, 0-2 carbons, 0-3 carbons, 0-4 carbons, 0-5 carbons, 0-6 carbons, 1-2 carbons, 1-3 carbons, 1-4 carbons, 1-5 carbons, 1-6 carbons, 2-3 carbons, 2-4 carbons, 2-5 carbons, 2-6 carbons, 3-4 carbons, 3-5 carbons, 3-6 carbons, 4-5 carbons, 4-6 carbons, 5-6 carbons, 5 carbons or 6 carbons. These examples may be referred to, respectively, as C0-1 alkyl, C0-2 alkyl, C0-3 alkyl, respectively, etc.

The term "alkoxy" includes both branched and straight chain terminal alkyl groups attached to a bridging oxygen atom. Typical alkoxy groups include methoxy, ethoxy, n-propoxy, isopropoxy, tert-butoxy and the like.

The term "aminoalkyl" refers to an amino derivative of an alkyl radical.

The term "halo" or "halogen" refers to fluoro, chloro, bromo or iodo.

The term "aryl" refers to phenyl or naphthyl which may be optionally substituted. Typical aryl groups include, but are not limited to, phenyl, 4-chlorophenyl, 4-fluorophenyl, 4-bromophenyl, 3-chlorophenyl, 3-fluorophenyl, 3-nitrophenyl, 3-(trifluoromethyl)phenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl, 2-iodo-4-methylphenyl, and the like.

The terms "heteroaryl" or "hetaryl" refer to a substituted or unsubstituted 3-10 membered unsaturated ring containing one, two, three or four heteroatoms, preferably one or two heteroatoms independently selected from oxygen, nitrogen and sulfur or to a bicyclic unsaturated ring system containing up to 10 atoms including at least one heteroatom selected from oxygen, nitrogen and sulfur. Examples of heteroaryls include, but are not limited to, 2-pyridinyl (synonym: 2-pyridyl), 3-pyridinyl (synonym: 3-pyridyl) or 4-pyridinyl (synonym: 4-pyridyl), pyrazinyl, 2-, 4-, or 5-pyrimidinyl, pyridazinyl, triazolyl, tetrazolyl, imidazolyl, 2- or 3-thienyl (synonym: thiophenyl), 2- or 3-furyl (synonym: furanyl), pyrrolyl, oxazolyl, isoxazolyl, thiazolyl, isothiazolyl, oxadiazolyl, thiadiazolyl, quinolyl, isoquinolyl, benzimidazolyl, benzotriazolyl, benzofuranyl, and benzothienyl. In certain embodiments the heterocyclic ring may be optionally substituted with up to two substituents.

The term aminoaryl" refers to an amino substituted heteroaryl.

The term "phenoxide" is a conjugate base of phenol and can be synthesized by mixing phenol with a base (e.g. sodium hydride, sodium hydroxide etc.)

The term "homocycle" refers to a carbocycle.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "substantially pure" when used with respect to enantiomers indicates that one particular enantiomer (e.g. an S enantiomer or an R enantiomer) is substantially free of its stereoisomer. In various embodiments substantially pure indicates that a particular enantiomer is at least 70%, or at least 80%, or at least 90%, or at least 95%, or at least 98%, or at least 99% of the purified compound. Methods of producing substantially pure enantiomers are well known to those of skill in the art. For example, a single stereoisomer, e.g., an enantiomer, substantially free of its stereoisomer may be obtained by resolution of the racemic mixture using a method such as formation of diastereomers using optically active resolving agents (see, e.g., Stereochemistry of Carbon Compounds, (1962) by E. L. Eliel, McGraw Hill; Lochmuller (1975) J. Chromatogr., 113(3): 283-302). Racemic mixtures of chiral compounds of the can be separated and isolated by any suitable method, including, but not limited to: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. Another approach for separation of the enantiomers is to use a Diacel chiral column and elution using an organic mobile phase such as done by Chiral Technologies (www.chiraltech.com) on a fee for service basis.

EXAMPLES

The following examples are offered to illustrate, but not to limit the claimed invention.

Example 1

An Allosteric BACE Inhibitor Peptide that Interacts with the Loop F Region and Prevents APP Substrate Cleavage Inhibition of the aspartyl protease β-site amyloid precursor protein cleaving enzyme 1 (BACE1, BACE) has emerged as an appealing target for reduction of amyloid-β (Aβ), the principle component of the amyloid plaques that characterize Alzheimer's disease (AD). Presently, there are direct active-site BACE inhibitors under study in the clinic and while early reports indicate such inhibitors are safe in short-term studies, they may ultimately be hindered by induction of undesirable side effects due to inhibition of cleavage of non-amyloid precursor protein (APP) substrates. One approach to lessen this risk is directed at development of allosteric BACE inhibitors that interact with an exosite remote from the catalytic site and prevent APP binding and cleavage. Allosteric inhibition may be more specific for both substrate and enzyme. Previously, a series of peptides with a YPYF(I/L)P(L/Y) (SEQ ID NO:6) motif were identified that bound to an exosite and inhibited BACE cleavage of an APP-like substrate. This is similar to a BACE-binding antibody that was shown by co-crystallization to act as an allosteric inhibitor, binding to an exosite and inducing an alteration of conformation of Loop F of BACE thus preventing substrate docking and cleavage. This example provides evidence that an exosite-binding peptides act similarly to the antibody and can interact with Loop F to inhibit BACE cleavage of the long APP-like substrate MBP-APPC125, but not a short P5-P5' substrate. Our peptide-BACE binding model suggests that it is possible to identify brain-penetrant small molecule mimetics of the peptide that could induce similar Loop F conformational alteration.

Allosteric inhibition of BACE has previously been described by Kornacker et al. who found through screening combinatorial phage peptide libraries that peptides with a YPYFP motif bound to an exosite even in the presence of saturating amounts of a direct BACE inhibitor and inhibited cleavage of an APP-like substrate.

The allosteric mechanism of BACE inhibition is revealed by paradoxical effects in two assays, one which utilizes a long substrate such as chimeric protein MBP-APPC125 (maltose binding protein fused to the C-terminal 125 amino acids of APP comprising the α-, β-, and γ-cleavage sites) and the other a short substrate such as R&D Systems fluorogenic substrate P5-P5' (AS004). As shown in FIG. 4, panel A, when the exosite for allosteric inhibitor binding is empty, the long substrate docks properly and is cleaved. Upon binding of the allosteric inhibitor (FIG. 4, panel B) there is an alteration of conformation of docking subsites that prevents proper docking of the long substrate and cleavage is prevented. The short substrate does not interact with the altered subsites, however, and it can dock and be cleaved (FIG. 4, panel C).

In Kornacker et al. the relationship between the peptide binding exosite on BACE and any conformational effects on Loop F region was not elucidated. In silico molecular docking as well as molecular dynamic simulation analysis to were used to show that the exosite bound by Kornacker's Peptide 1-11 (here, termed Peptide 65005 or 65005) could in fact interact with and thus displace Loop F potentially modulating the binding of the long substrate to distal subsites S6 and S7 on BACE, and have thus provided a basis for identification and development of new allosteric BACE inhibitors. In vitro assays have been developed to screen for allosteric BACE inhibitors that could be used in a high throughput screening mode to identify small molecule brain-penetrant allosteric BACE inhibitors that would interact with Loop F and inhibit BACE similarly to the Genentech's Ab and the Kornacker peptide.

Results

Figure 17:
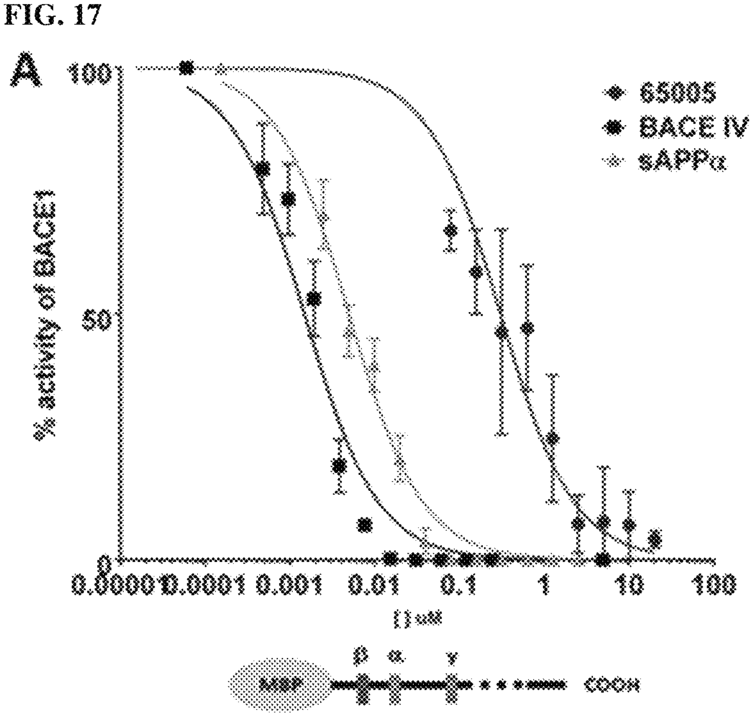
FIGS. 17A-E show that Peptide 65005 effects in P5-P5' and MBP-APPC125 assays, and inhibitors.
Figure 17:
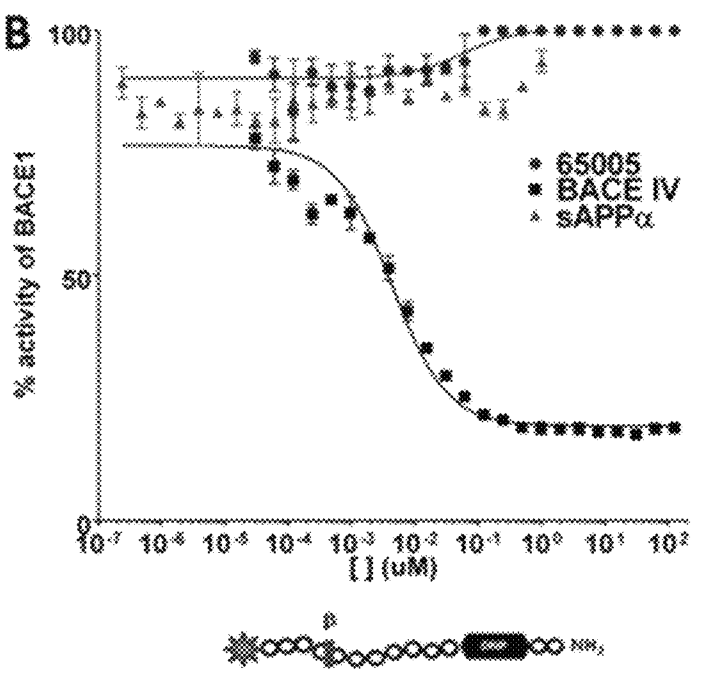
Figure 17:
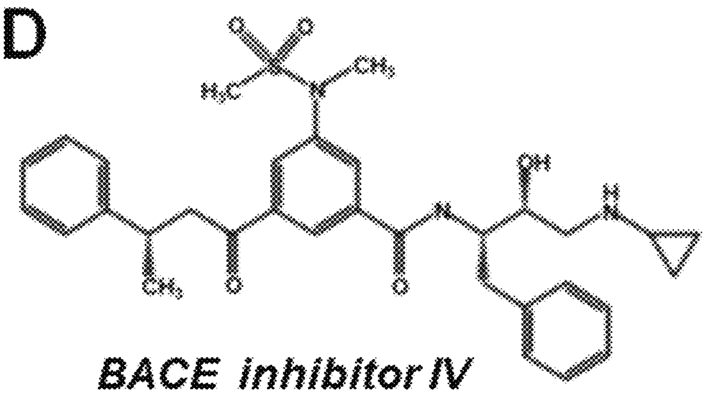

As shown in FIG. 17, panel A, direct BACE inhibitor IV (BACE IV), sAPPα, and Peptide 65005 all induced dose-response inhibition of BACE cleavage of the long MBP-APPC125 substrate. Peptide 65005 and sAPPα did not inhibit cleavage of the short P5-P5' substrate, but BACE IV showed dose-response inhibition (FIG. 17, panel B). These results support an allosteric mechanism for BACE inhibition by both Peptide 65005 and sAPPα, and are similar to those reported for the Genentech Ab and mAb 1A11 that inhibit cleavage of the long, but not the short, substrates; this is in contrast to a direct active site inhibitor such as BACE IV, which inhibited cleavage of both substrates.

Figure 18:
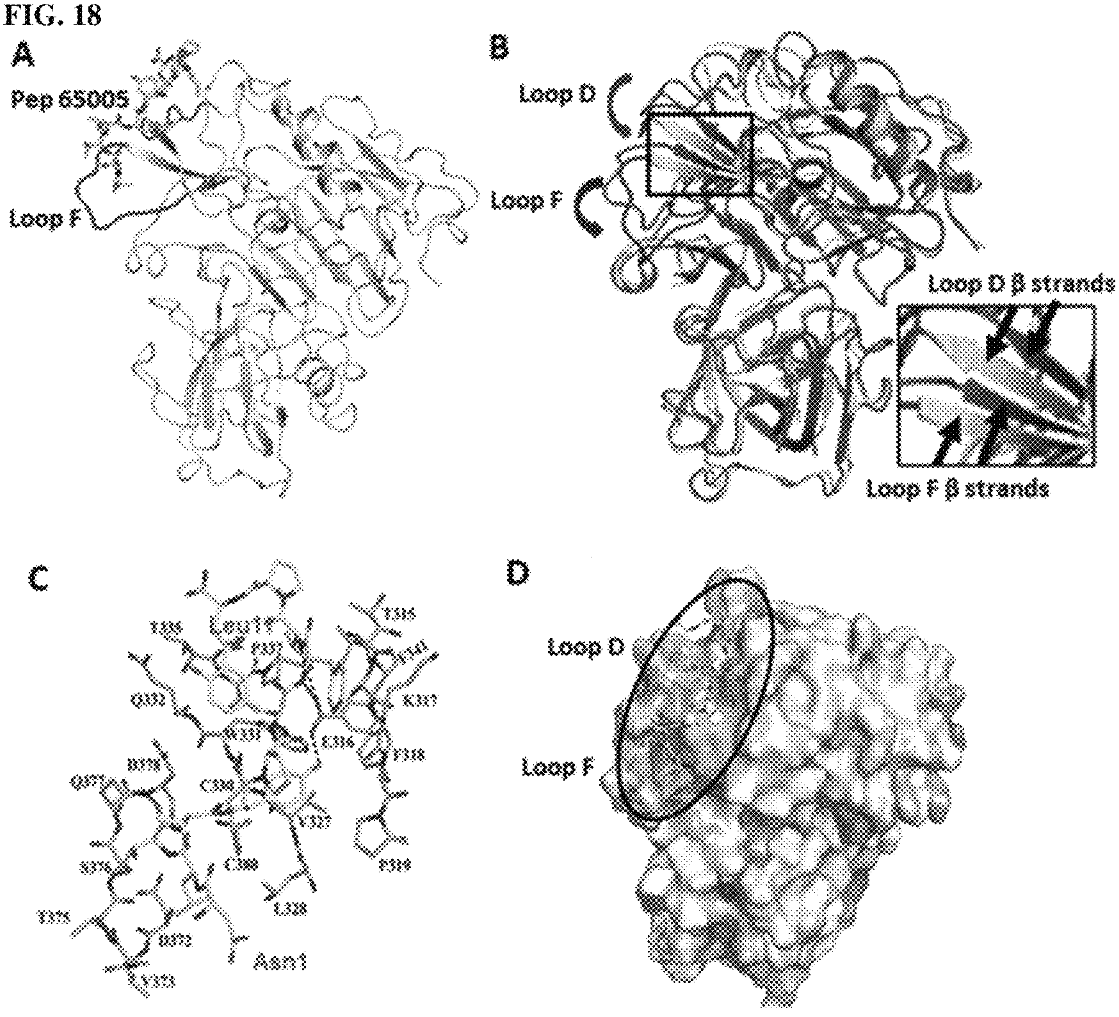
FIGS. 18A-D show that peptide 65005 binds at BACE exosite and alters Loops F and D.

To elucidate the mechanism by which Peptide 65005 exerts allosteric inhibition, in silico experiments were performed first by conducting molecular docking in Swissdock (www.swissdock.ch) with Peptide 65005 and BACE which showed strong binding of the Peptide to the Kornackers binding site. A Molecular Dynamics software simulation of Peptide 65005 interaction with BACE at the Kornacker exosite was performed. In a 5Ons experiment modeling Peptide 65005 binding to BACE structure (PDB ID: 1×N3) after removal of BACE inhibitor 1, significant displacement of Loop F was seen upon Peptide 65005 binding (FIG. 18, panel A) and additional changes in positions of Loop D and both the Loop F and D β strands were revealed by overlay of the Pep 65005-bound and unbound BACE structures (FIG. 18, panel B). It is the displacement of Loop F in particular that leads to compression of subsites S6 and S7 thus preventing docking and cleavage of the APP-like (but not the P5-P5') substrate. The BACE amino acid residues with which Peptide 65005 interacts as well as the location and electrostatic interaction of Peptide 65005 with the BACE were also determined (FIGS. 18, panels C and D, respectively) and were found to be very near Loops F and D.

Figure 19:
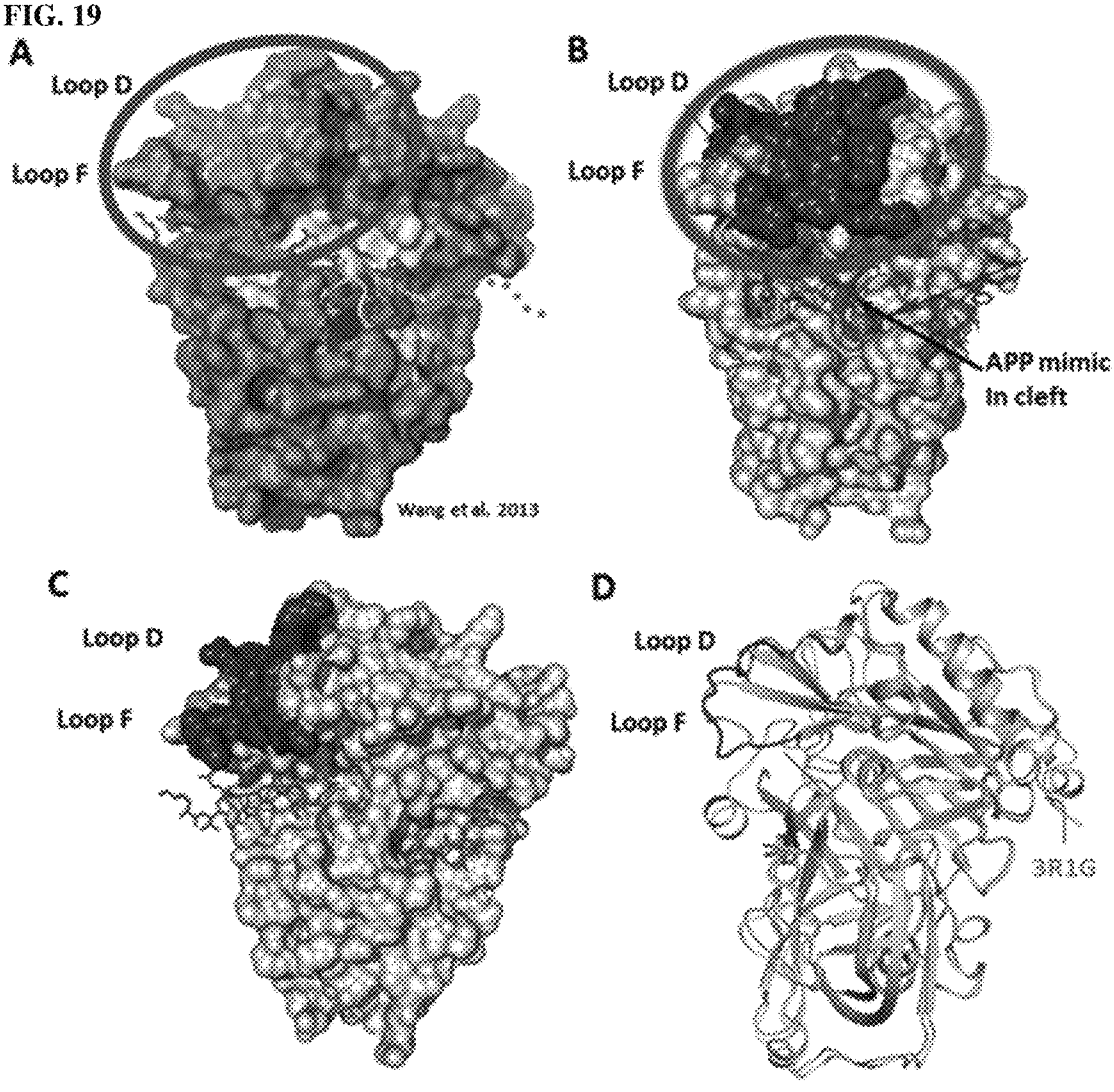
FIGS. 19A-D shows that Peptide 65005 binds and alters BACE conformation similarly to Genentech/Roche allosteric inhibitor antibody.

Further in silico modeling confirmed the location of the exosite bound by Peptide 65005, as well as the conformational effects of binding, are very similar to the Genentech/Roche allosteric inhibitor Ab. Side-by-side comparison of the Ab binding exosite as shown in Wang et al. (FIG. 19, panel A) and the Peptide 65005 exosite described by Kornacker et al. for Peptide 65005 (FIG. 19, panel B)—confirmed by the in silico analysis—reveal their similarity. Specifically, the Peptide 65005 exosite includes Loops F, D, and C (FIG. 19, panel C). To further confirm the similar conformational impact of Ab and Peptide 65005 binding, an overlay of BACE conformation when the Ab is bound and when Peptide 65005 is bound was generated (FIG. 19, panel D).

Discussion

Allosteric inhibition of BACE provides an opportunity to identify new AD therapeutics that could overcome potential obstacles to successful long-term use of inhibitors: inhibition of cleavage of non-APP substrates and brain penetrance. An allosteric inhibitor also offers an opportunity for enzyme specificity due to the presence of unique exosite binding sites. Such specificity was shown for the anti-BACE Ab, which did not inhibit either BACE2 or Cathepsin D, suggesting that the site with which the allosteric inhibitor interacts may be unique to BACE. Zhou et al. also described the Loop F and D region of BACE to be unique among aspartyl proteases. Because the in silico analysis suggests Peptide 65005 acts as a ligand for the same exosite, this peptide could be an initial lead for development of allosteric BACE inhibitors. The binding and effects of this peptide, and additional small molecule leads, will of course need to be verified by co-crystallization studies.

Given that individual substrates may interact with BACE with differing affinities at different subsites, it is anticipated that allosteric modulation of the S6 and S7 subsites by an allosteric inhibitor would depend on the affinity of the specific substrate residues to these sites. It is known that these affinities are different for APP and another substrate of BACE, NRG1. Therefore, size of the substrate is not the only factor contributing to effects of allosteric inhibitors on cleavage.

The in silico docking, simulations, and models provide insights into the binding of Peptide 65005 at the exosite and indicate, that similarly to the Ab, Peptide 65005 could interact with and displace Loop F, resulting in the observed allosteric BACE inhibition. Such in silico analysis, along with the AlphaLISA-based MBP-APPC125 assay that can be run in HTS mode to screen the UCLA compound library, and the P5-P5' substrate assay to determine an allosteric inhibitory profile, provides the first potential to identify small molecule Loop F-interacting allosteric BACE inhibitors that would also be cell- and brain-penetrant allowing the effects on sAPPα and Aβ 1-42 to be demonstrated in vitro and in vivo.

Utilizing the analytical and testing methods described here, it has been established a program to identify allosteric inhibitors of BACE with the goal of restoring normal APP processing in Mild Cognitive Impairment due to AD and AD itself. In addition, as upregulation of A43 production is implicated in development of cerebral amyloid angiopathy, poor outcome after traumatic brain injury or stroke, and progression of amyotrophic lateral sclerosis, an allosteric inhibitor of BACE may also have a role in treatment of these other neurological diseases/conditions.

Materials and Methods

The MBP-APPC125 Assay

The recombinant BACE (rBACE) used was expressed and purified by modification of the method of Sussman et al. BACE activity in the presence of Peptide 65005, sAPPα and direct active-site inhibitor BACE IV was determined using a commercially available detection kit (Sigma, CS0010).

For the long-substrate assay, MBP-APPC125 was expressed and purified in the UCLA DOE protein expression Core. BACE stock at 200 μg/mL was thawed on ice and diluted in BACE assay buffer to a working concentration of 17 ng/μL. MBP-APPC125 stock solution at 2.5 mg/mL was diluted in water to a working concentration of 12.5 ng/μL. Proteins stocks were at 1 μM in phosphate buffer (20 mM phosphate pH 6.8, 100 mM NaCl) and serially diluted. The AlphaLISA assay is composed of an antibody mix and a donor mix. The antibody mix has anti-A43 acceptor beads (Cat #AL275) having the 82E1 antibody specific for A43 N-terminus and anti-A43 from the AL202 kit (Cat #AL202AC) having the 4G8 antibody biotinylated. The donor mix has streptavidin-coated donor beads. Perkin Elmer standard protocol was followed to prepare the mix. In this assay, 1 μL of MBP-APPC125 working solution was incubated with 2 μL of protein for 15 min and then 3 μL of BACE working solution were loaded into each well and incubated for 60 min at 37° C. Then, 2 of the antibody mix was loaded into each well and incubated for 1 h at room temperature. After this time, the donor mix was added into the wells and incubated for 30 min. Then, the AlphaLISA signal was detected using the PE Enspire instrument. Data was graphed using GraphPad Prism software.

Secondary Short P5-P5' Substrate Assay

The P5-P5' fluorogenic substrate is available commercially (R&D Systems, ES004). In this protocol, BACE stock at 200 μg/mL was thawed on ice and diluted in BACE assay buffer to a BACE working concentration of 17 ng/μL. Proteins stocks were at 1 μM in phosphate buffer (20 mM phosphate pH 6.8, 100 mM NaCl). The protein was diluted serially in the same buffer. The substrate was diluted in BACE assay buffer to a concentration of 16 tM and kept protected from light. Then, 2 μL of BACE working solution and 2 μL of protein were incubated for 15 min at room temperature followed by the addition of 6 μL of substrate. The fluorescence was read immediately in a SpectraMax M2 fluorescence reader from Molecular Devices set at an excitation wavelength of 320 nm and emission wavelength at 405 nm every 30 min for 2 h.

MBP-APPC125 WT Substrate

This substrate has was produced using a protocol previously described "Purification and cloning of amyloid precursor protein beta-secretase from human brain", *Nature,* 402 (1999) 537-40. The purified MBP-APPC125 is stored at ~2 mg/ml.

Recombinant BACE (rBACE) Production

A His6-BACE1 expression construct in a pET24a vector encompassing human BACE1 (amino acids 43-454) with two mutations (K136A/E138A) that alter crystal packing under the control of the T7 promoter and with an N-terminus hexahistidine tag was used. The vector confers kanamycin resistance. ON cultures of *E. coli* BL21 were started by inoculation of media with colonies from the transformation plate; then the ON cultures were expanded to several 1 L flasks and grown in the presence of kanamycin at 37° C. with shaking (200-220 rpm) until $OD_{600}$ reached ~0.8-0.9. Throughout production and purification, aliquots were taken for SDS-PAGE analysis. The protein was purified by a standard protocol as outlined in the Sussman publication. The protein was refolded using the published protocol (extended time) and enzyme activity confirmed.

Recombinant sAPPα Production

A MBP-sAPPα expression construct in a pKM596 vector (Fox 2003) conferring carbenicillin resistance encompassing human sAPPα (amino acids 19-613) fused to maltose binding protein under control of the tac promoter was used to synthesize recombinant sAPPα. Overnight cultures of *E. coli* Rosetta-Gami B were started by inoculation of media with colonies from the transformation plate and grown ON with shaking at 30° C.; then the cultures were expanded to several 1 L flasks and grown in the presence of carbenicillin and chloramphenicol at 37° C. with shaking (200-220 rpm) until OD600 reached ~0.5-0.6 (6-10 hours). Shaker temperature was shifted to 18° C. and cultures were allowed to cool before induction of protein expression by addition of IPTG. Growth continued at 18° C. with shaking for 10-12 hours. The flasks were then moved to a cold room and incubated at 4° C. without shaking for ~10 hours to allow chaperones to assist in folding of sAPPα, increasing yield. Cells were harvested by centrifugation and pellets frozen at −80° C. before lysis. Immobilized-metal affinity chromatography (IMAC) beads were used for purification. Pellets were lysed in ice-cold lysis buffer using three passes through an Avestin Emulsiflex C-3. After centrifugation, the lysate supernatant was mixed and incubated with the beads for 4-20 hours at 4° C., and then the beads decanted into a gravity flow column. After washing, elute-bound protein was released with Elution buffer and dialysed against dialysis buffer at 4° C. for ~2 hours. The post-dialysis elution fraction was then further purified on a heparin column and by size exclusion chromatography. Concentrated protein was stored in the presence of protease inhibitors. The MBP fusion partner was then removed by TEV protease by incubation at 1:500 TEV:target at 4° C. sAPPα was further purified by anion exchange chromatography using a Q-sepharose column: MBP does not bind the column and is found in the flow-through. After extensive washing with buffer IEX-A, sAPPα was eluted with a gradient of IEX-B and pure protein dialyzed against 20 mM Tris pH 6.8, 100 mM NaCl, 2.5 mM EDTA.

In Silico Analysis of Exosite Peptide Binding Site

Molecular graphics and analyses were performed using the UCSF Chimera package. Chimera is developed by the Resource for Biocomputing, Visualization, and Informatics at the University of California, San Francisco (supported by NIGMS P41-GM103311).

Molecular Docking and Molecular Dynamic Simulation

To study the effect of Peptide 65005 binding to BACE1, molecular docking was done using Swissdock (www.swissdock.ch/). Analysis of the docking results was performed using Chimera and Pymol. The strongest binding energy was seen at the Kornackers binding site, and this result was used to proceed. Molecular dynamics simulations were performed using BACE1 (PDB ID: 1×N3) structure (after extraction of the BACE inhibitor 1) for docking and MD simulations. BACE1 and Peptide 65005 docking was modeled utilizing PEP-SiteFinder and RosettaDock. MD simulations were carried out for BACE1 with and without the peptide. The structural minimizations and MD simulations were carried out using the AMBER 16 program. After adding hydrogens, the protein structures were solvated in a truncated octahedral TIP3P box of 12 Å, and the system was neutralized with sodium ions. Periodic boundary conditions, Particle Mesh Ewald summation and SHAKE-enabled 2-femto seconds time steps were used. Langevin dynamics temperature control was employed with a collision rate equal to 1.0 $ps^{-1}$. A cutoff of 13 Å was used for nonbonding interactions. Initial configurations were subjected to a 1000-step minimization with the harmonic constraints of 10 $kcal \cdot mol^{-1} \cdot A^{o-2}$ on the protein heavy atoms. The systems were gradually heated from 0° K to 300° K over a period of 50 ps with harmonic constraints. The simulations at 300° K were then continued for 50 ps during which the harmonic constraints were gradually lifted. The systems were then equilibrated for a period of 500 ps before the 50 ns production runs. All simulations were carried out in the NPT ensemble. Equilibration and production run simulations were carried out using the Sander and PMEMD modules (optimized for CUDA) of AMBER 16.0 (ff14SB), respectively (4). Initial structures prior to MD were used as the reference structures for the root mean square deviation (RMSD) calculations. All analyses were performed using the cpptraj module of AmberTools 16.

Example 2

An Allosteric BACE Inhibitor Peptide that Interacts with the Loop F Region and Prevents APP Substrate Cleavage The most potent peptides reported by Kornacker et al. were synthesized it was shown that peptide 65007 (65007), can interact with the Loop F region of BACE, has the allosteric inhibition substrate profile, shows selectivity for both BACE as an enzyme and APP as a substrate, and can act as an inhibitor of APP cleavage in a cell model.

The effect of 65007 on the Loop F region was revealed by in silico molecular docking and molecular dynamic simulation analyses. Our data thus provide a lead peptide for exploratory medicinal chemistry to identify mimetics that interact at the Loop F region of BACE. In addition, a predictive in silico model for design and evaluation of such allosteric BACE inhibitors that would interact with Loop F and inhibit BACE has been developed.

Results

Figure 20A:
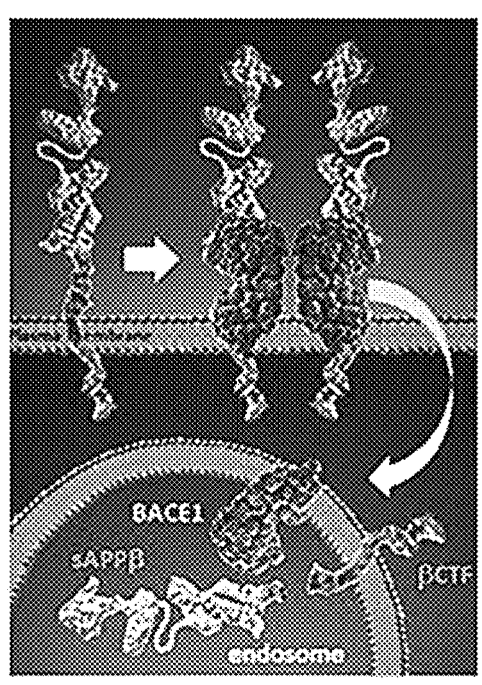
FIGS. 20A-D show the BACE processing of APP and allosteric inhibition of BACE as determined in long- and short-substrate assays.
Figure 20B:
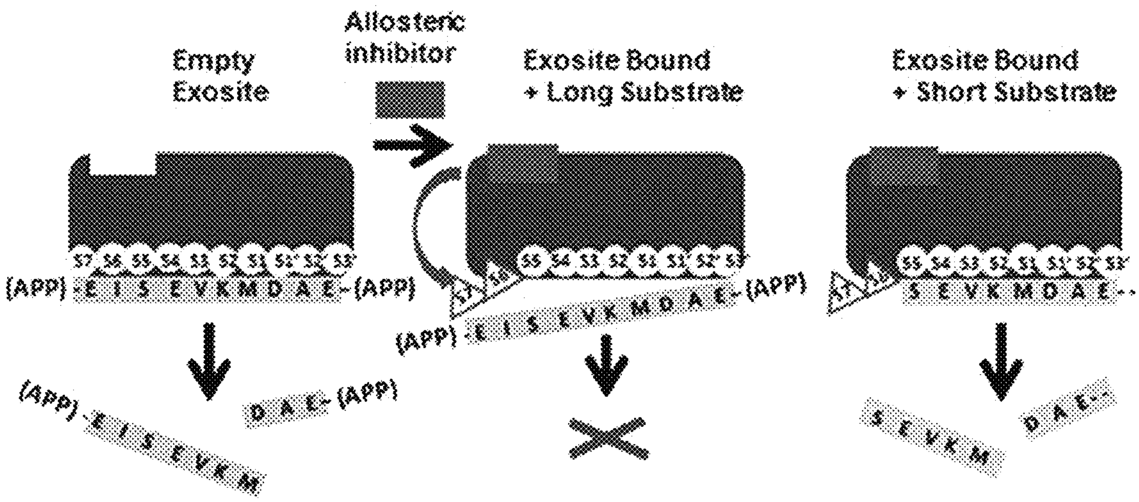
Figure 20C:
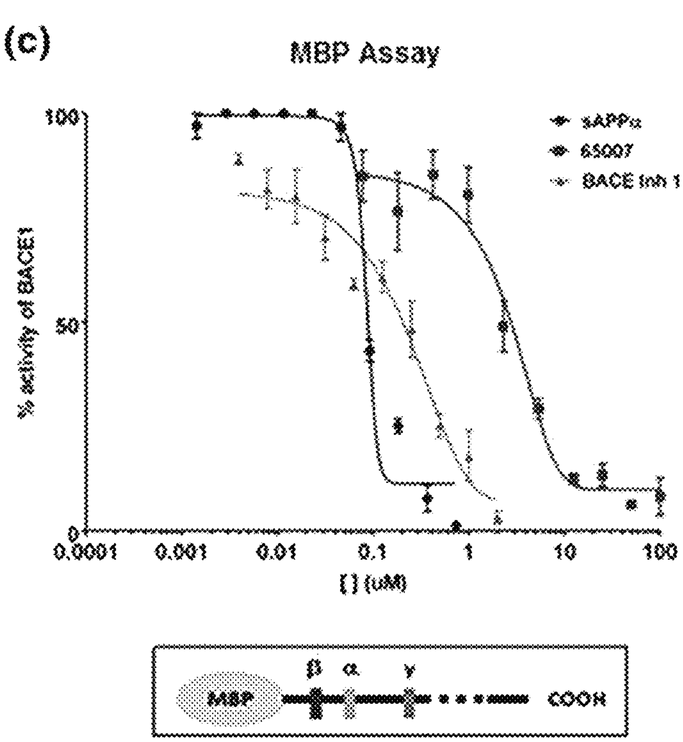
Figure 20D:
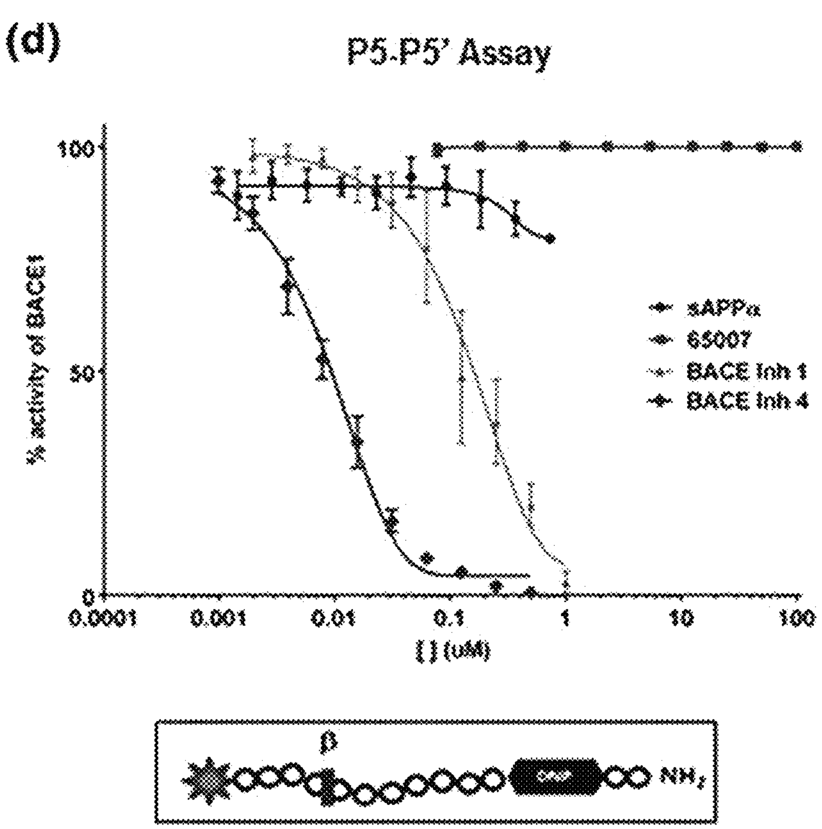

As shown in FIG. 20C, direct BACE inhibitor 1 (BACE Inh 1), recombinant sAPPα (rsAPPα, sAPPα), and 65007 all induced dose-response inhibition of BACE cleavage of the long MBP-APPC125 substrate with IC50s of 0.2, 0.08, and 2.8 μM respectively. Peptide 65007 and sAPPα did not, however, inhibit cleavage of the short substrate, but the direct BACE inhibitors BACE Inh 1 and BACE inhibitor 4 (BACE Inh 4) showed dose-response inhibition, with IC50s of >100, >2, 0.16, and 0.01 μM, respectively (FIG. 20D). These results support an allosteric mechanism for BACE inhibition by both 65007 and sAPPα, and these substrate cleavage profiles are similar to those reported for the Genentech Ab and mAb 1A11 that inhibit cleavage of the long, but not the short, substrate.

Figure 21A:
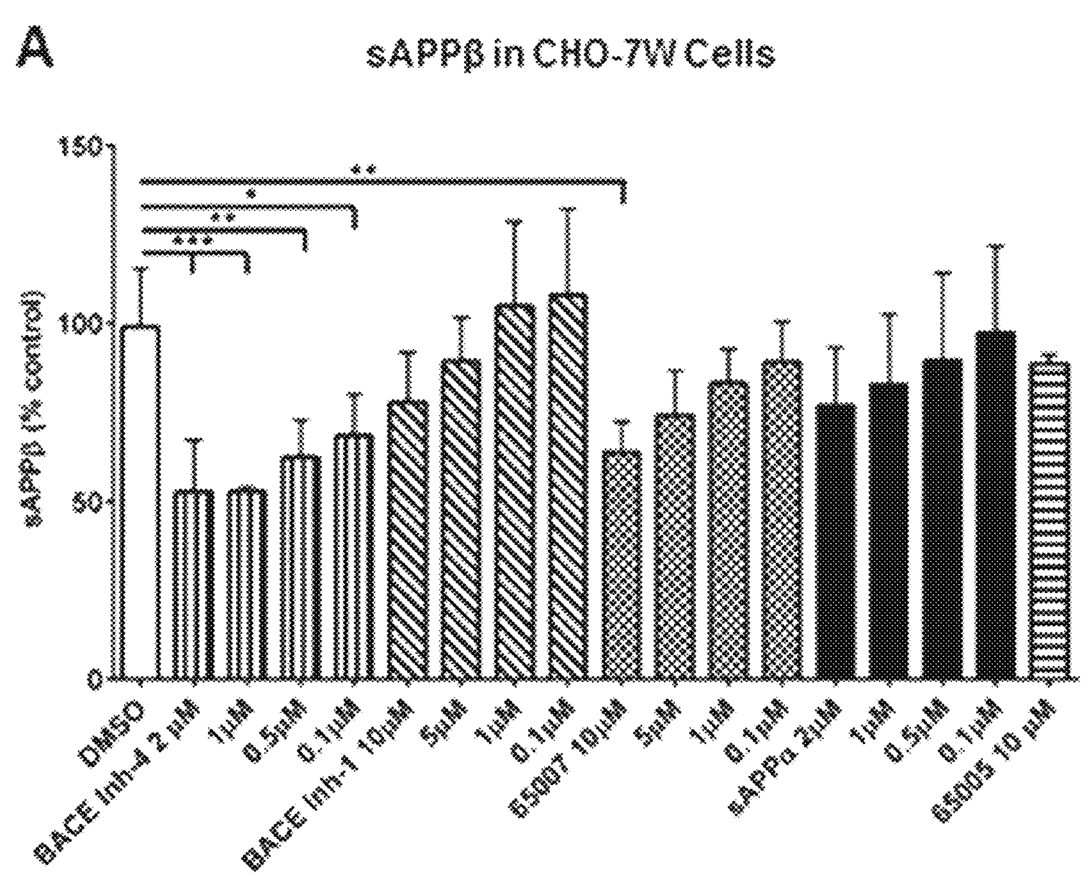
FIGS. 21A-E shows the effects of Peptide 65007, sAPPα, BACE inhibitor 1 and 4 on sAPPβ and Aβ production from CHO-7W cells.
Figures 21B, 21C, 21D:
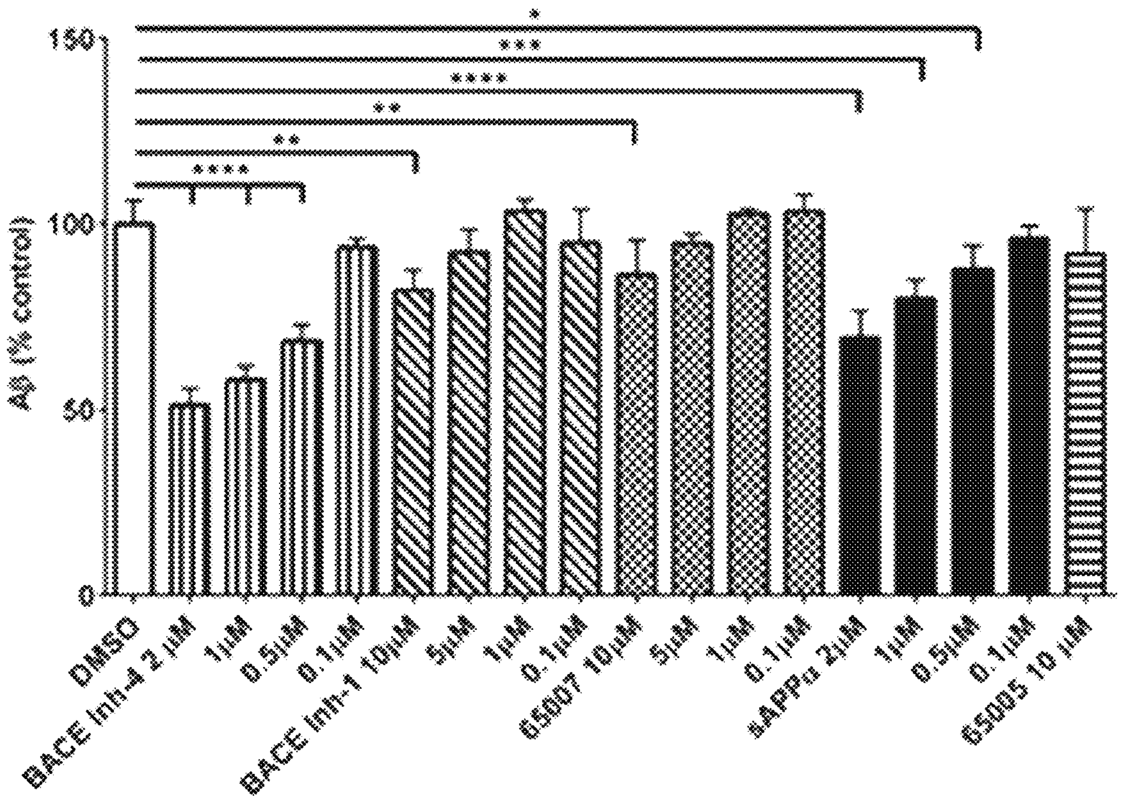
Figure 21E:
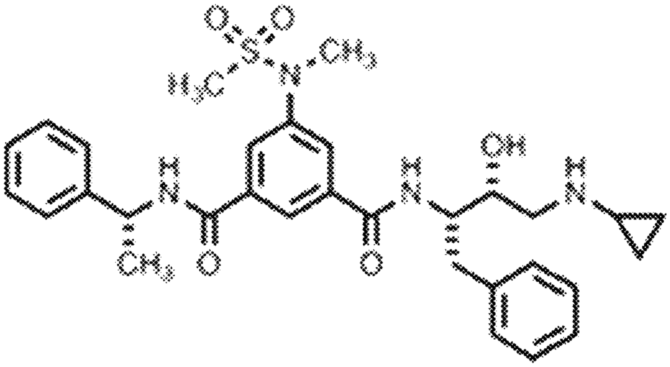

BACE inhibition was further confirmed in vitro in a cell-based system comprising Chinese hamster ovary (CHO) cells stably transfected with wildtype human APP (CHO-7W). Both 65007 and sAPPα were found to elicit a dose-response decrease BACE cleavage product sAPPβ (FIG. 21A) with EC50s of ~10 and <5 μM, respectively; and showed a trend to a dose-response decrease in Aβ with a significant decrease at the highest concentration used (FIG. 21B). These results confirm the ability of both 65007 and sAPPα to exert their effects on BACE in cell models.

Figure 22A:
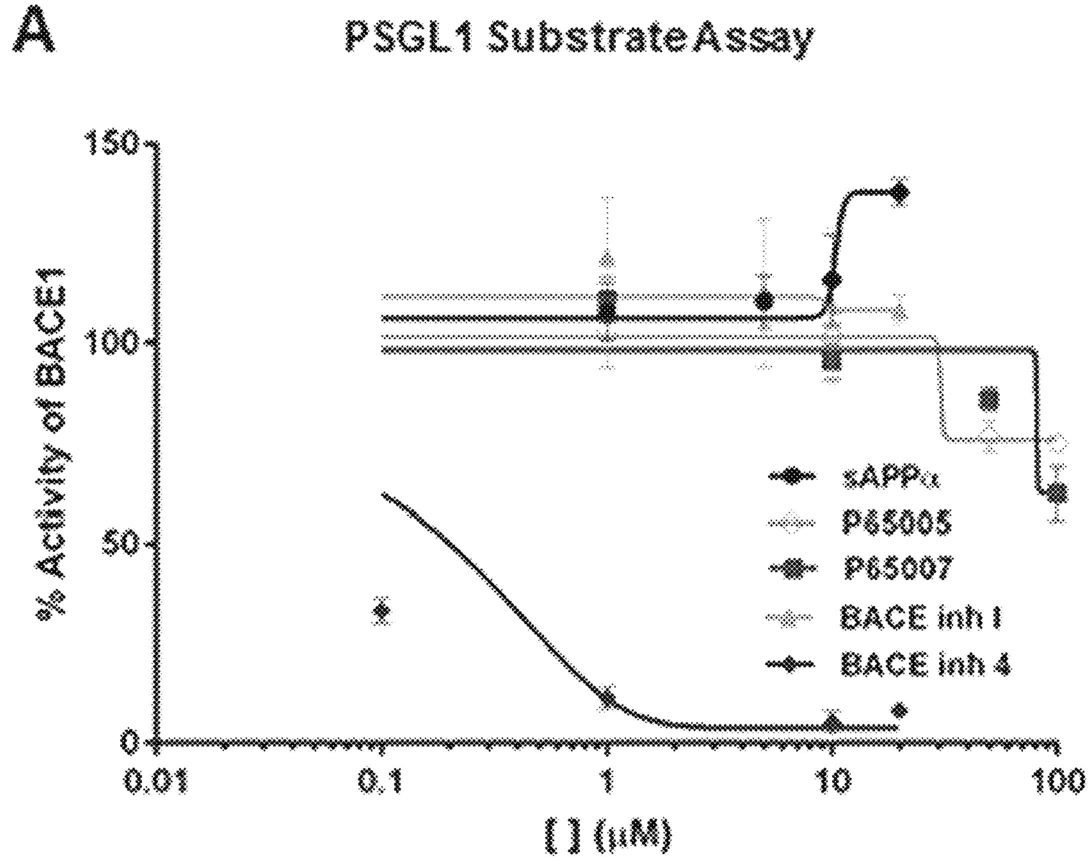
FIG. 22A-E shows the relative enzyme selectivity of peptide 65007 and sAPPα.
Figure 22B:
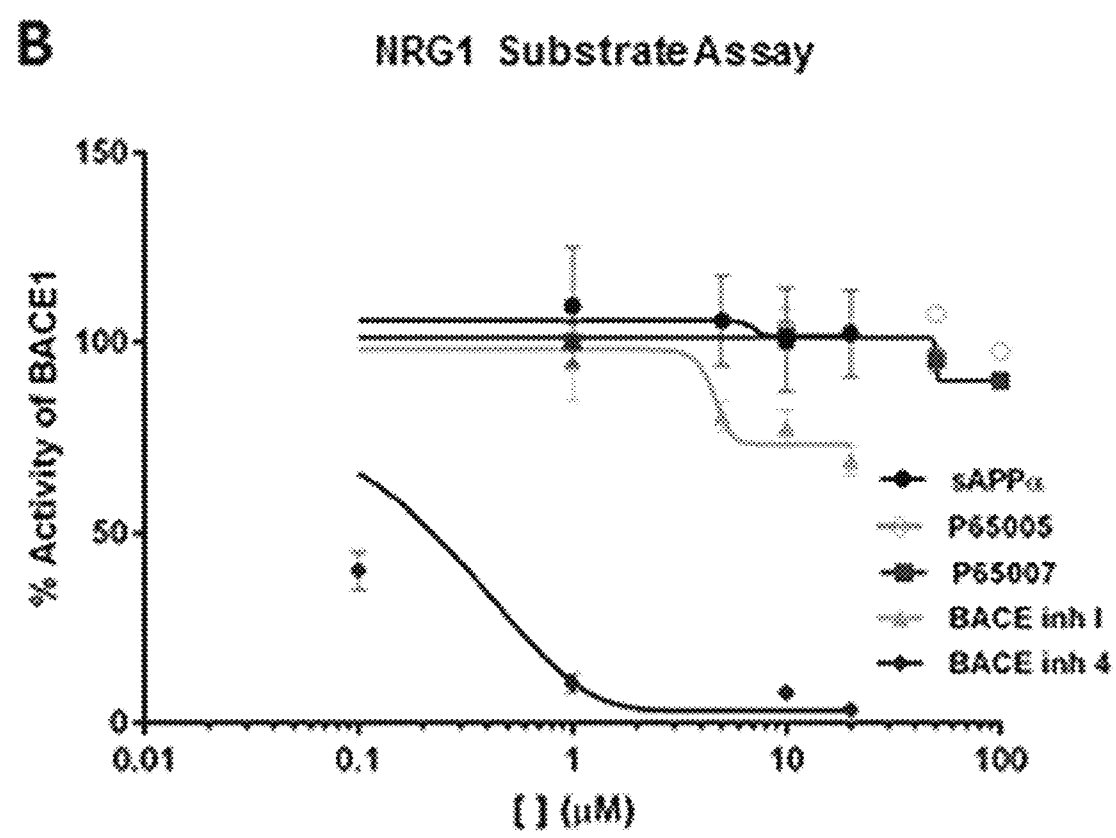
Figure 22C:
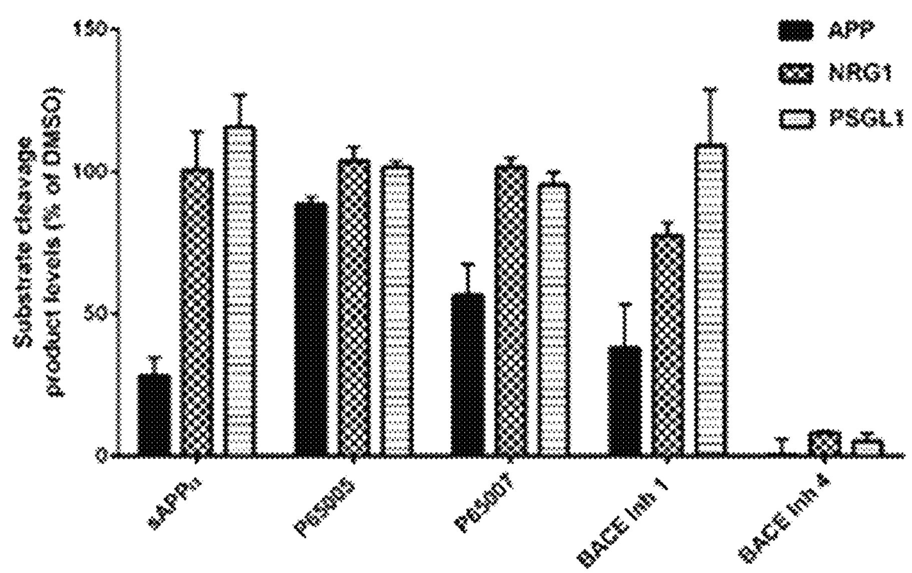
Figure 22D:
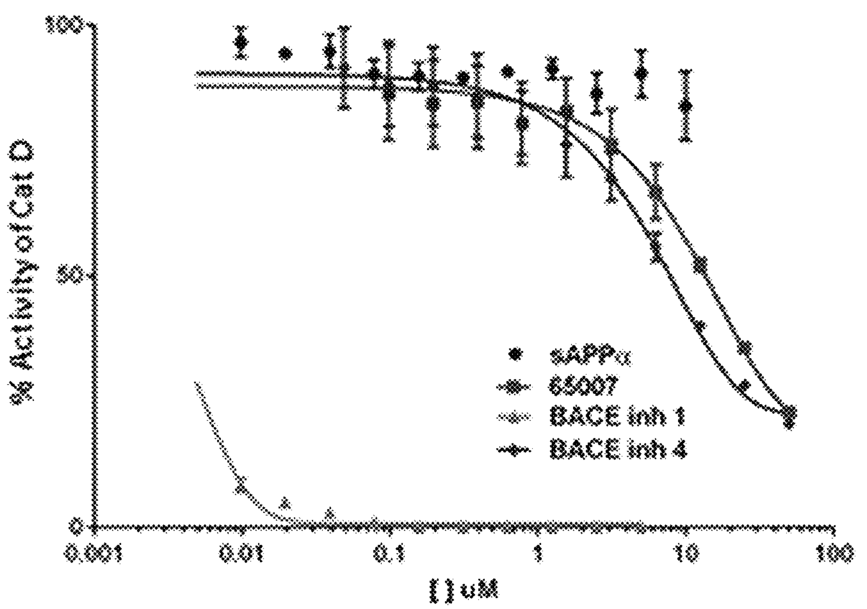

Peptide 65007 and sAPPα substrate selectivity is shown in FIGS. 22A & B, where neither one showed any significant inhibition of PSGL1 or NRG1 cleavage at concentrations below 50 μM. The $EC_{50}$s for both PSGL1 and NRG1 were >10 μM for 65007, sAPPα, and BACE Inh 1, and <1 μM for BACE Inh 4. Relative selectivity for APP as a substrate based on comparison of inhibition of APP, NRG1, and PSGL1 cleavage (FIG. 22C) was determined to be sAPPα>65007>BACE Inh 1>BACE Inh 4. Enzyme selectivity is shown in FIG. 22D, where sAPPα elicited no inhibition of Cat D activity, BACE Inh 1 inhibited Cat D at a relatively low concentration (IC50 of <0.01 μM), while 65007 did so at relatively high concentrations, with IC50s over 5 μM.

Figure 24A:
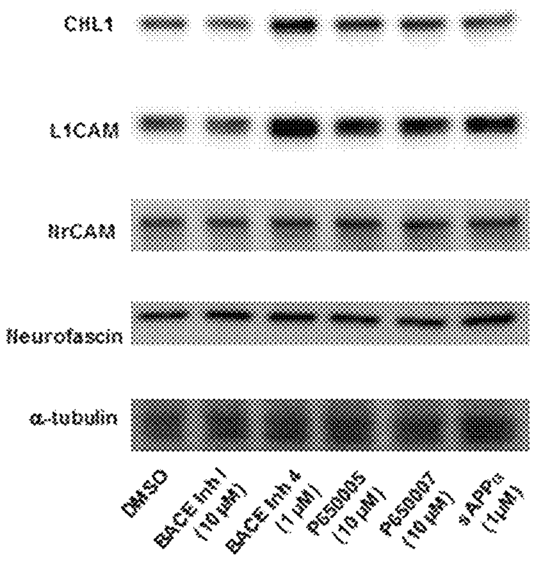
FIGS. 24A & B shows the inhibition of BACE cleavage of CHL1, L1CAM, NrCAM and neurofascin in primary neuronal culture.
Figure 25A:
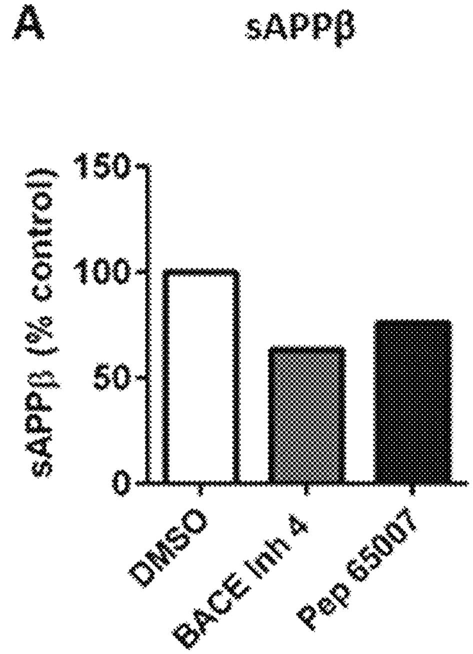
FIGS. 25A & B shows the selectivity for APP versus CHL1.
Figure 25B:
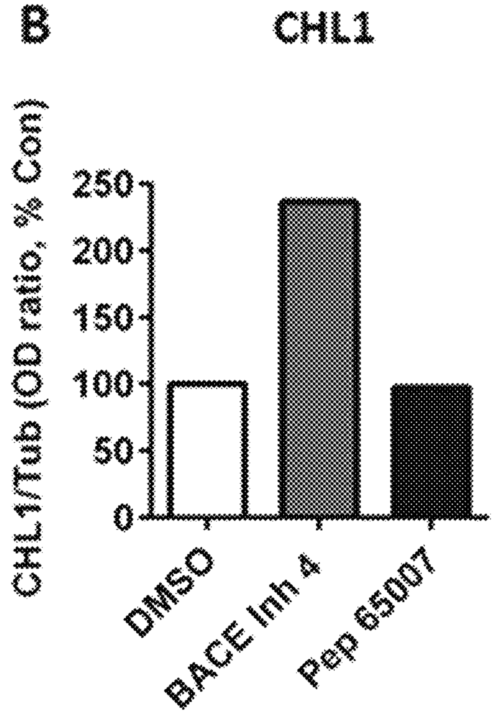
FIG. 25B shows that at the same concentrations, only BACE inhibitor 4, and not 65007, inhibits CHL1 cleavage and results in an increase in uncleaved substrate; data presented as CHL1/tubulin OD ratios as a percentage of control.

Additional preliminary substrate selectivity was revealed as a result of 24-hour treatment of mouse primary cortical neurons with the panel of inhibitors. Only BACE Inh 4 at 1 μM inhibited cleavage of CHL1 and L1CAM by BACE as reflected by the ratio of uncleaved substrate to loading control α-tubulin (FIGS. 24A & B). Also, only BACE Inh 4 and BACE Inh 1 (at 10 μM) treatment resulted in an increase of uncleaved NrCAM or neurofascin, respectively; none of the other inhibitors increased the amount of these substrates. Importantly, while 65007 did not inhibit cleavage of these substrates, at the same concentrations used, it shows inhibition of the BACE cleavage of APP (FIG. 25). These studies confirm the greater effect of direct inhibitor BACE Inh 4 on CHL1 and L1CAM cleavage than NrCAM and neurofascin cleavage as described in Zhou et al. 2012, and relevant to this report, further supports the selectivity of peptide 65007 and sAPPα for inhibition of BACE cleavage of APP.

Figures 22E, 23A:
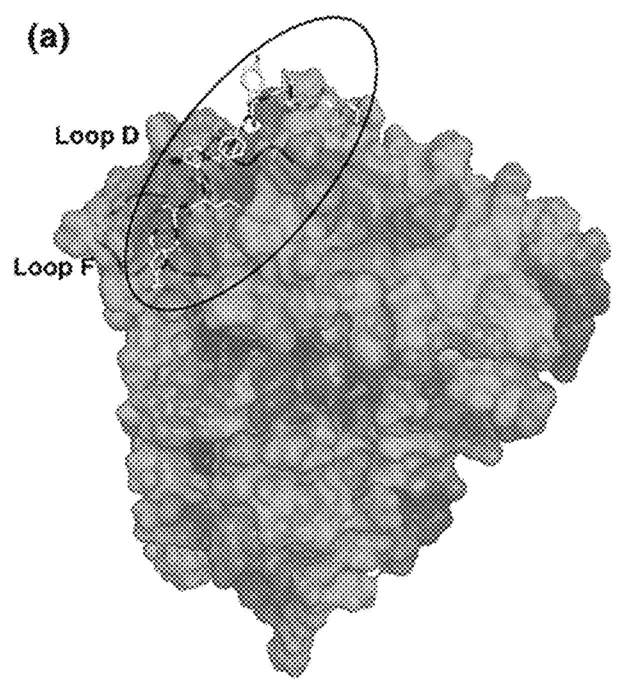
FIG. 23A-D shows the interaction of Peptide 65007 with an exosite, and effects on Loops D and F.
Figure 23B:
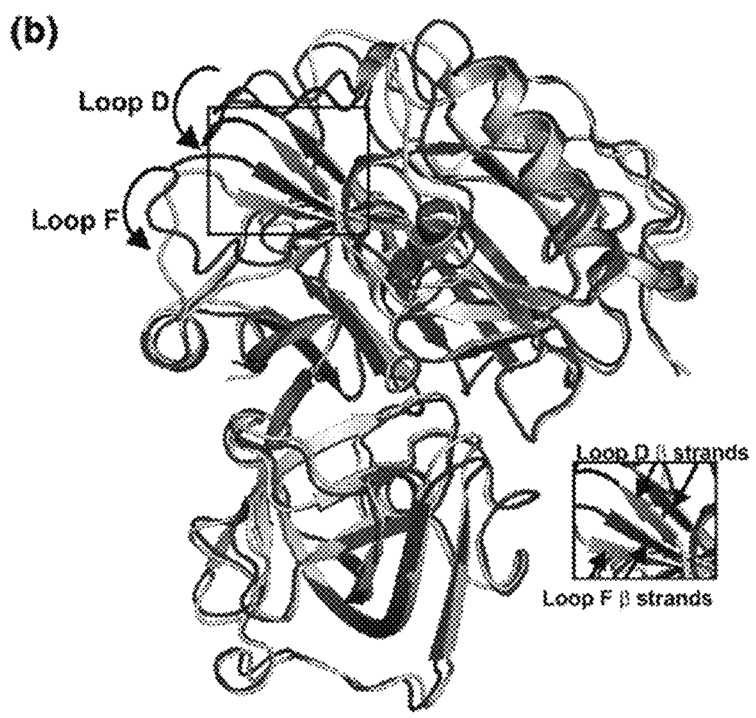
Figure 23C:
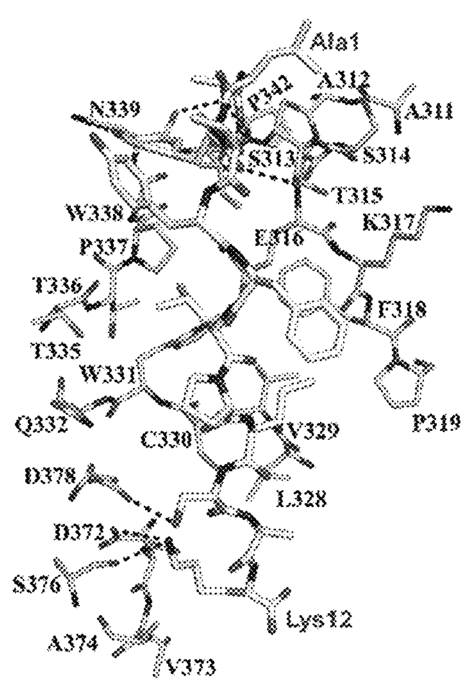
Figure 23D:
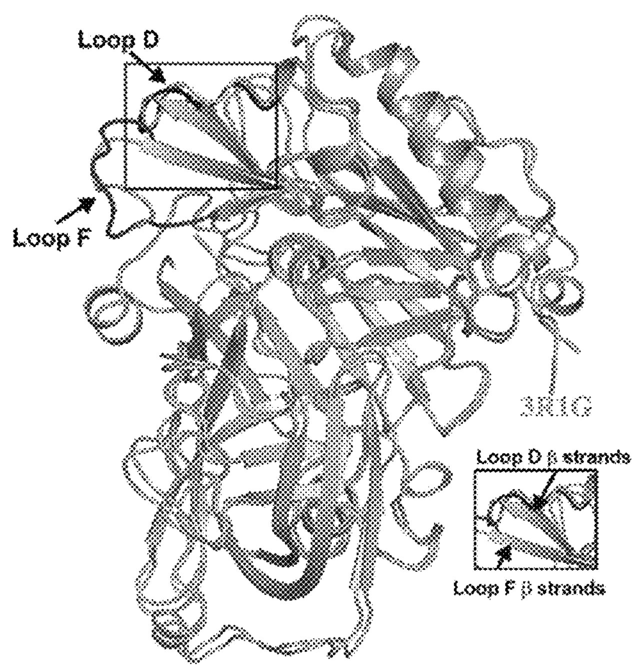

To elucidate the mechanism of Peptide 65007 allosteric inhibition, in silico experiments were performed first by conducting molecular docking in Swissdock (www.swissdock.ch/) with 65007 and comparing the model to the crystal structure of the Genentech Ab and BACE. This analysis also showed the location of 65007 interaction with BACE to be very near Loops F and D (FIG. 23A). A molecular dynamics simulation of 65007 interaction with BACE at the Loop F region was conducted. In a 50 ns experiment modeling binding of 65007 to BACE using the crystal structure (PDB ID: 1×N3) after removal of BACE Inh 1 to generate an apo BACE structure, significant displacement of Loop F was seen upon binding and simulation with 65007. At the end of the 50 ns simulation, the positions of both the Loop F and D β strands (FIG. 23B) show significant movement. The overlay of the BACE backbone when bound to 65007 and that when bound to the Ab seen in crystal structure (pdb:3R1G) were very similar (FIG. 23D). The 50 ns molecular dynamic simulation reveals that binding of 65007 to the Loop F region results in a change of the protein backbone from the apo BACE structure (pdb: 1×N3) to the BACE Ab structure (pdb: 3R1G). The displacement of Loop F can lead to a compression of subsites S6 and S7 that could prevent docking and cleavage of the long APP substrate but not affect the short substrate. The enzyme residues with which 65007 interacts with were (FIG. 4C) found to be very near Loops F and D.

Discussion

Allosteric inhibitors of BACE represent a new class of potential AD therapeutics directed to this key target that could overcome impediments in long-term use of direct BACE inhibitors. These impediments include inhibition of the cleavage of non-APP substrates and poor brain-penetrance. An allosteric inhibitor is likely to be enzyme-selective due to the presence of unique exosite binding sites in the Loop F region of BACE. The BACE inhibitor Ab, which was shown through co-crystallization to bind the Loop F region and cause a shift in the protein backbone (pdb:3R1G), did not inhibit other related aspartyl proteases such as BACE2 or Cathepsin D, suggesting that the site with which the allosteric inhibitor interacts may be unique to BACE. Zhou et al. also describe the Loop F and D region of BACE as being unique among aspartyl proteases.

Substrate selectivity—the absence of inhibition of cleavage of non-APP substrates—is conferred by an allosteric inhibitor inducing specific backbone and subsite perturbations. Given that individual substrates interact with BACE with varying affinities at different subsites, it is anticipated that any inhibitory effects resulting from the modulation of the distal S6 and S7 subsites by an inhibitor that interacts with the Loop F region would depend on the affinity of the specific substrate residues to these sites. It is known that these affinities are different for APP and another substrate of BACE, NRG1.

Figure 24B:
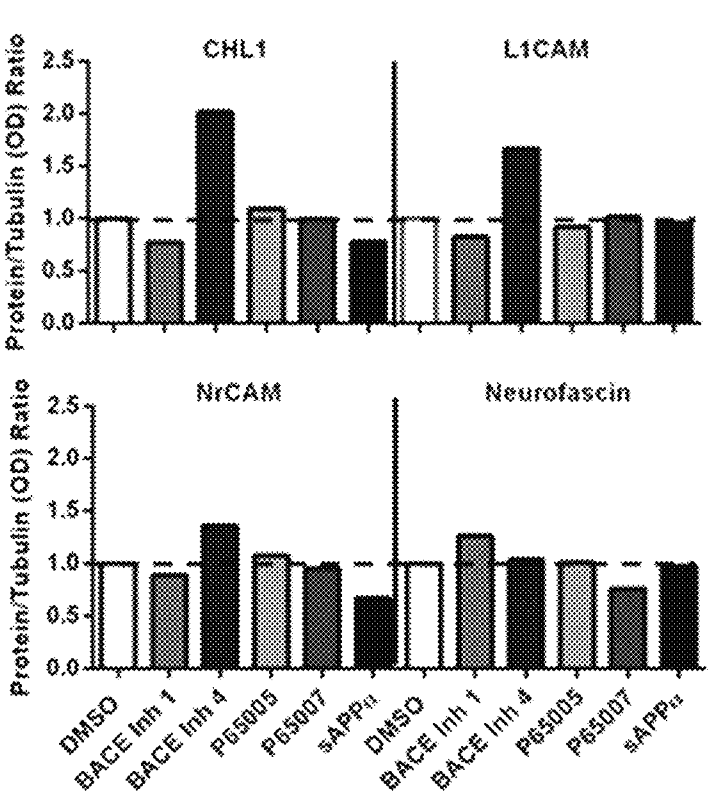
FIG. 24B (Upper) shows the ratios of ODs for CHL1/α-tubulin (left) and L1CAM/α-tubulin (right) are shown and only BACE Inh 4 (blue) clearly inhibited cleavage; BACE Inh 1, peptides 65005 and 65007 and sAPPα did not. (Lower) Only BACE Inh 4 and BACE Inh 1 treatment resulted in an increase of uncleaved NrCAM or neurofascin, respectively; none of the other inhibitors increased the amount of uncleaved NrCAM or neurofascin substrate.

Shown here—for the first time—is that a relatively small peptide inhibitor of BACE can, in a similar fashion to the Ab, interact with the Loop F region, inhibit cleavage of only a long APP-like but not a short substrate of BACE, decrease the levels of sAPPβ in cell models, and be selective for the APP substrate and BACE enzyme. In cell models the lead peptide 65007 shows little inhibition of NRG1 or PSGL1 relative to APP cleavage by BACE. Further evidence of substrate selectivity is observed in mouse primary cortical neurons, where treatment with peptide 65007 shows no significant inhibition of neural cell adhesion molecules such as LI and CHL1 when compared to treatment with the direct inhibitor BACE Inh 4 (FIG. 24).

The in silico docking and molecular dynamic simulations provide insights into the binding of 65007 to the exosite and indicate that like the Ab, 65007 could interact with and displace Loop F, causing a BACE protein backbone shift very similar to that observed in the Ab-BACE co-crystal (pdb:3R1G), resulting in the observed allosteric BACE inhibition. Thus, the in silico model could be used as a predictive tool in design of Loop F-interacting mimetics of 65007. Peptide 65007 itself is an initial lead for exploratory medicinal chemistry development to identify either peptidomimetics or small molecules that bind to the Loop F exosite and act as allosteric BACE inhibitors.

Utilizing the in silico docking, molecular dynamic simulations, dual substrate assays, and selectively/cell-based assays, it has been established as an approach to identify a new class of small allosteric inhibitors of BACE. Allosteric inhibitors showing good potency and selectivity would then be tested in in vitro and in vivo permeability assays, and ultimately in in vivo efficacy studies using models of AD. Such an allosteric inhibitor need not be as potent as the current direct BACE inhibitors in the clinic, as it is has been reported that even modest reductions in BACE activity can be of benefit (at least in a disease model) with time. The goal is to restore normal APP processing in Mild Cognitive Impairment (MCI) and AD. In addition, as upregulation of Aβ production is implicated in development of cerebral amyloid angiopathy (CAA), poor outcome after traumatic brain injury (TBI) or stroke, and progression of amyotrophic lateral sclerosis (ALS), an allosteric inhibitor of BACE may also have a role in treatment of these other neurological diseases/conditions.

Materials and Methods

The MBP-APPC125 Assay

The recombinant BACE (rBACE) used was expressed and purified by modification of the method of Sussman et al. BACE activity in the presence of Peptide 65007, sAPPα and direct active-site inhibitor BACE inhibitor 1 was determined using the long MBP-APPC125 substrate.

MBP-APPC125 was expressed and purified in the UCLA DOE Protein Expression Core using a protocol previously described in *Nature* 402 (1999) 537-40. The purified MBP-APPC125 is stored at ~2.5 mg/ml.

For the assay, BACE stock at 200 μg/mL was thawed on ice and diluted in BACE assay buffer to a working concentration of 10 ng/μL. MBP-APPC125 stock solution at 2.5 mg/mL was diluted to 0.1 mg/mL in 10 mM Tris, pH 7.5, 0.2% Triton X-100, and 150 mM guanidine hydrochloride to allow it to refold for 1 hour at room temperature. Then MBP-APPC125 was diluted in water to a working concentration of 12.5 ng/μL. Inhibitor working solutions were at 100 μM (peptide 65007), 0.25 uM (BACE inhibitor 1) and 0.73 μM (sAPPα) or DMSO and were serially diluted. The AlphaLISA assay is composed of an antibody mix and a donor mix. The antibody mix has anti-Aβacceptor beads (82E1 antibody specific for Aβ N-terminus) and the anti-Aβ 4G8 biotinylated antibody. The donor mix has streptavidin-coated donor beads. Perkin Elmer (PE) standard protocol was followed to prepare the mix. In this assay, 2 μL of MBP-APPC125 working solution was incubated with 2 μL of inhibitor for 2 hours and then 5 μL of BACE working solution were loaded into each well and incubated for 60 min at 37° C. Then 2 μL of the antibody mix was loaded into each well and incubated for 1 h at room temperature. After this time, the donor mix was added into the wells and incubated for 30 min. The AlphaLISA signal was then detected using the PE Envision instrument. Data was graphed using GraphPad Prism software.

Secondary Short Substrate Assay

The short fluorogenic BACE1 substrate is available commercially (R&D Systems, ES004). In this protocol, BACE stock at 200 μg/mL was thawed on ice and diluted in BACE assay buffer to a BACE working concentration of 7.5 ng/μL. Compound working solutions were at 100 μM (peptide 65007), 0.5 μM (BACE Inh 4), 0.73 μM (sAPPβ), and 1 μM (BACE inhibitor 1). sAPPα stocks were at 5 μM in TRIS buffer (20 mM TRIS pH 6.8, 100 mM NaCl) and the inhibitors were at 10 mM in DMSO. The inhibitors were diluted serially in the same buffer. The substrate was diluted in BACE assay buffer to a concentration of 50 μM and kept protected from light. Then, 4 μL of assay buffer, 2 μL of BACE working solution, and 2 μL of inhibitor were incubated for 15 min at room temperature followed by the addition of 2 μL of substrate. The fluorescence was read immediately in a SpectraMax M2 fluorescence reader from Molecular Devices set at an excitation wavelength of 320 nm and emission wavelength at 405 nm every 30 min for 2 h.

Peptide 65005, 65007 and Recombinant sAPPα Production

Peptides 65005 and 65007 were synthesized at Bachem (www.bachem.com) using standard solid phase synthesis protocol. The sAPPβ was prepared at the UCLA DOE Protein Expression Core using a MBP-sAPPα expression construct in a pKM596 vector (Fox 2003) conferring carbenicillin resistance encompassing human sAPPα (amino acids 19-613) fused to maltose binding protein (MBP) under control of the tac promoter was used to synthesize recombinant sAPPα. Overnight (ON) cultures of *E. coli* Rosetta-Gami B (DE3) were started by inoculation of media with colonies from the transformation plate and grown ON with shaking at 30° C.; then the cultures were expanded to several 1 L flasks and grown in the presence of carbenicillin and chloramphenicol at 37° C. with shaking (200-220 rpm) until $OD_{600}$ reached ~0.5-0.6 (6-10 hours). Shaker temperature was shifted to 18° C. and cultures were allowed to cool before induction of protein expression by addition of IPTG. Growth continued at 18° C. with shaking for 10-12 hours. The flasks were then moved to a cold room and incubated at 4° C. without shaking for ~10 hours to allow chaperones to assist in folding of sAPPα, increasing yield. Cells were harvested by centrifugation and pellets frozen at −80° C. before lysis. Immobilized-metal affinity chromatography (IMAC) beads were used for purification. Pellets were lysed in ice-cold lysis buffer using three passes through an Avestin Emulsiflex C-3. After centrifugation, the lysate supernatant was mixed and incubated with the beads for 4-20 hours at 4° C., and then the beads decanted into a gravity flow column. After washing, elute-bound protein was released with Elution buffer and dialysed against dialysis buffer at 4° C. for ~2 hours. The post-dialysis elution fraction was then further purified on a heparin column and by size exclusion chromatography. Concentrated protein was stored in the presence of protease inhibitors. The MBP fusion partner was then removed by TEV protease by incubation at 1:500 TEV:target at 4° C. sAPPα was further purified by anion exchange chromatography using a Q-sepharose column; MBP does not bind the column and is found in the flow-through. After extensive washing with buffer IEX-A, sAPPα was eluted with a gradient of IEX-B and pure protein dialyzed against 20 mM Tris pH 6.8, 100 mM NaCl, 2.5 mM EDTA.

The NRG1 and PSGL1 Assays

To assay NRG1 and PSGL1 cleavage, 293T cells were plated in 96-well plates at 40,000 cells/well and incubated overnight at 37° C. in 5% $CO_2$. The following day, cells were co-transfected with NRG1 and BACE plasmids or PSGL1 and BACE plasmids using Lipofectamine2000, as described previously. The pAPtag5-NRG1-β1 construct was kindly provided by Dr. Carl Blobel. The BACE1 construct was a gift from Dr. Michael Willem and Dr. Christian Haass.

Six hours after transfection, the reagents were removed and media containing the different inhibitors at various concentrations were loaded into each well and incubated overnight. Stock sAPPα at 110 μM was diluted to 20, 10, 5, and 1 μM in DMEM high glucose containing 10% FBS and 1% penicillin-streptomycin ("medium"). Stock BACE inhibitor I (Anaspec cat #AS-23958) at 1 mM in DMSO was diluted to 20, 10, 5, and 1 μM; stock BACE inhibitor 4 (EMD Millipore cat 565788) at 10 mM in DMSO was diluted to 10, 5, 1, and 0.1 μM; and stock Peptides 65005 and 65007 at 10 mM in DMSO were diluted to 100, 50, 10, and 1 μM all in medium with 1% DMSO final.

For the secreted alkaline phosphatase assay, 20 μL of media were removed and added to a new 96-well plate. Then, 200 μl of reaction solution (0.1 M glycine, pH 10.4, 1 mM $MgCl_2$, 1 mM $ZnCl_2$ containing 1 mg/ml 4-nitrophenyl phosphate disodium salt hexahydrate (Sigma S0942) was loaded into each well of the plate. The absorbance was read at 405 nm for 60 min in 30 min intervals in a SpectraMax M5.

The Cathepsin D Assay

The short fluorogenic CatD substrate and Recombinant Human Cathepsin D (CatD) is available commercially (R&D Systems, ES001; Biolegend, 556704, respectively). The CatD assay buffer used was made according Biolegend's Bioassay protocol (0.1 M NaOAc, 0.2 M NaCl, pH 3.5). First, CatD stock solution at 200 μg/mL was thawed on ice and diluted with assay buffer to 20 μg/mL and incubated at 37° C. for 30 min to activate the protein. Then CatD at 20 μg/mL was diluted in CatD assay buffer to a CatD working concentration of 5 ng/μL. Compound working solutions were at 50 μM and serially diluted at 2.5% DMSO. The substrate was diluted in CatD assay buffer to a concentration of 50 μM and kept protected from light. Then, 4 μL, of assay buffer, 2 μL, of CatD working solution, and 2 μL of inhibitor were incubated for 30 min at room temperature followed by the addition of 2 μL of substrate. The fluorescence was read immediately in a SpectraMax M5 fluorescence reader from Molecular Devices set at an excitation wavelength of 320 nm and emission wavelength at 405 nm every 30 min for 2 h. Briefly, the reaction mix with the assay components and sAPPα, Peptide 65005, BACE Inh 1, BACE Inh 4, or pepstatin at concentrations between 0.01-10 μM, 0.1-50 μM, 0.005-5 μM, 0.05-50 μM, and 0.05-50 μM, respectively, were incubated as described above; then read on a plate reader.

In Vitro Analysis of sAPPβ and Aβ in CHO-7W Cells

Chinese hamster ovary cells stably transfected with wild-type human APP were plated at a density of $4\times10^5$ cells/mL in DMEM/High Glucose media with 1% pen-strep and 10% FBS overnight and were treated with BACE Inh 1 or Peptide 65007 at 0.1, 1, 5, and 10 μM; BACE Inh 4 at 0.1, 0.2, 1, and 2 μM; or sAPPα at 0.1, 0.5, 1, and 2 μM overnight; peptide 65005 was used at a single concentration of 10 μM. For the AlphaLISA assay media was collected and complemented with protease inhibitor, and sAPPβ (see supplementary material) and Aβ (PE cat #AL276) levels were determined. The samples were read using the in the PE Envision plate reader according to manufacturer's instructions.

Cleavage of CHL1, L1CAM, NrCAM, Neurofascin and APP in Primary Neuronal Cultures The methods used to determine cleavage of CHL1, L1CAM, NrCAM, neurofascin and inhibition of BACE cleavage of APP in primary cortical neurons from mouse embryos treated for 24 hours are described in *Supplementary Methods* (Campagna et al, J. Mol Biol (2018), 430, 1566-1576).

In Silico Analysis of Exosite Peptide Binding Site

Molecular graphics and analyses were performed using the UCSF Chimera package. Chimera is developed by the Resource for Biocomputing, Visualization, and Informatics at the University of California, San Francisco (supported by NIGMS P41-GM103311).

Molecular Docking and Molecular Dynamic Simulation

To study the effect of Peptide 65007 binding to BACE1, molecular docking was done using Swissdock (www.swissdock.ch/). Analysis of the docking results was performed using Chimera and Pymol. The strongest binding energy was seen at the Kornackers binding site, and this result was used to proceed.

Molecular Dynamics Simulation

Molecular dynamics (MD) simulations were performed using BACE1 (PDB ID: 1×N3) structure (after removal of the BACE inhibitor 1) for docking and MD simulations. BACE1 and Peptide 65007 docking was modeled utilizing PEP-SiteFinder and RosettaDock. MD simulations were carried out for BACE1 with and without the peptide. The structural minimizations and MD simulations were carried out using the AMBER 16 program. After adding hydrogens, the protein structures were solvated in a truncated octahedral TIP3P box of 12 Å, and the system was neutralized with sodium ions. Periodic boundary conditions, Particle Mesh Ewald summation and SHAKE-enabled 2-femto seconds time steps were used. Langevin dynamics temperature control was employed with a collision rate equal to 1.0 $ps^{-1}$. A cutoff of 13 Å was used for nonbonding interactions. Initial configurations were subjected to a 1000-step minimization with the harmonic constraints of 10 $kcal\cdot mol^{-1}$. $A^{o-2}$ on the protein heavy atoms. The systems were gradually heated from 0° K to 300° K over a period of 50 ps with harmonic constraints. The simulations at 300° K were then continued for 50 ps during which the harmonic constraints were gradually lifted. The systems were then equilibrated for a period of 500 ps before the 50 ns production runs. All simulations were carried out in the NPT ensemble. Equilibration and production run simulations were carried out using the Sander and PMEMD modules (optimized for CUDA) of AMBER 16.0 (ff14SB), respectively (4). Initial structures prior to MD were used as the reference structures for the root mean square deviation (RMSD) calculations. All analyses were performed using the cpptraj module of AmberTools 16.

Results

Mouse primary cortical neurons were treated for 24 hours with the panel of inhibitors to determine effects on cleavage of CHL1, L1 CAM, NrCAM, and neurofascin (FIG. 24A). BACE Inh 4 at 1 μM inhibited cleavage CHL1 and L1CAM, and to a lesser degree NrCAM, by BACE. BACE Inh 1 at 10 μM increased neurofascin. Peptide 65007 did not inhibit cleavage of these substrates, and at concentrations used, BACE cleavage of APP was inhibited (Fig, 252). Results are presented as the ratio of ODs for the target protein and α-tubulin for immunoblots and as percentage of control for the sAPPα as determined by AlphaLISA, and all are n=1.

The binding free energy of Peptide 65007 and Peptide 65005 were found to be −45.14 (±9.28) and −25.44 (±8.29) ΔG (kcal/mol), respectively. Modeling indicated Peptide 65007 bound more tightly to the exosite than 65005 and in the MBPC125 BACE cleavage assay the IC50's were 3 uM and >10 uM respectively suggesting binding and inhibitory activity are proportional.

Additional Methods

Cryopreserved primary cortical neurons (ThermoFisher A15586; C57BL/6 embryonic day-17) were plated into 6-well plates coated with poly-L-ornithine (0.5 mg/mL, Sigma P8638) and laminin (5 μg/mL, Sigma L2020) at $7\times10^5$ live cells/well according to the supplier's instructions in Neurobasal medium (ThermoFisher, Gibco 21103049) supplemented with B27 Plus (ThermoFisher, Gibco A3582801). Five days after plating, cells were exposed to BACE Inh 1, peptide 65005, or 65007, all at 10 μM; BACE Inh 4 or sAPPα both at 1 μM, or corresponded DMSO concentrations for control. The final concentration of DMSO for BACE Inh 1 was 0.9% and it was 0.09% for all other inhibitors. After treatment for 24 hours, cells were washed once with warm PBS and lysed using RIPA buffer (ThermoFisher #89900) with PIC and EDTA (Fisher #78438). After 30 minutes on ice, the protein concentrations of the samples were determined using BCA kit (ThermoFisher #23225). For immunoblotting, 10 μg/well of each samples was loaded on 4-12% Tris-Glycine gels and run at 125V, constant. Proteins from the gels were then transferred to PVDF membrane at 200 mA constant. To confirm even loading and transfer, membranes were stained with Ponceau S. After washing, non-specific binding of membranes was blocked with 5% non-fat dry milk (NFDM) and 3% BSA in PBS for 1 hr at RT. Blots were then incubated with primary antibodies ON at 4° C. These antibodies included anti-CRL1 (Abcam ab93197; 1 ug/ml final concentration), anti-L1CAM (Abcam, clone 2C2, ab24345; 1:1000 dilution), anti-neurofascin (Abcam 183082; 1:500 dilution), anti-NrCAM (Abcam ab24344; 1:500 dilution) and anti-tubulin (Sigma, SAB3501072; 1:5000) and all were diluted in PBS with 2% NFDM and 1% BSA. Membranes were then washed 4 times for 10 min each with PBST (0.1% Tween 20 in PBS) at RT. Membranes were then incubated with HRP-conjugated secondary IgG antibodies (Jackson ImmunoResearch Lab, anti-rabbit or mouse where appropriate) at 1:50000 dilution in PBST for 1 hr at RT. After 3 washes with PBST and 1 wash in PBS of 10 min each at RT, the membranes were incubated with Super Signal West Femto substrate (Thermo Scientific Pierce 34095) and the chemiluminescent signals were detected using a BioSpectrum 600 imaging system and quantified using VisionWorks Version 6.6A software (UVP; Upland, CA). An AlphaLISA assay was used to determine sAPPβ levels. The AlphaLISA assay is composed of an antibody mixture and a donor beads solution. The sAPPβ AlphaLISA antibody mixture is composed by Anti-APP antibody (R&D systems, cat #AF1168) conjugated to AlphaLISA acceptor beads, and Anti-sAPPβ antibody (IBL cat #18957) biotinylated. The donor beads solution has the streptavidin-coated donor beads. Perkin Elmer (PE) standard protocol is followed to prepare the mixtures. In this assay, 2 uL of cell media from primary culture are added to each well of white 384 well plate. Then, 2 μL of the antibody mixture are added to each well, incubated for 1 hour at room temperature, followed by the addition of 2 uL of donor beads solution to each well, incubated for 30 minutes at room temperature. Finally, the plate is read in a Perkin Elmer Envision plate reader.

The binding free energy for the peptides 65005 and 65007 to the BACE1 were estimated using the MMPBSA module in AMBER by taking snapshots (10000) at every 5 picoseconds from the 50 ns production run.

Table S1. Peptide 65007 and 65005 sequences, BACE-binding free energy, and BACE IC50. The sequences for peptides 65007 and 65005 are shown, as well as the BACE-binding free energy estimated from MMPBSA calculations. The $IC_{50}$s shown are for the MBP-C125 assay, both peptides were inactive in the P5-P5' assay.

TABLE S1

| Peptide | Sequence | BACE Binding ΔG (kcal/mol) | BACE IC50 (μM) |
|---|---|---|---|
| 65007 | Ac-A-L-Y-P-Y-F-L-P-I-S-A-K-NH2 | -45.14 (±9.28) | ~3 |
| 65005 | Ac-N-L-T-T-Y-P-Y-F-I-P-L-NH2 | -25.44 (±8.29) | >10 |

What is claimed is:

1. A compound according to the formula:

III

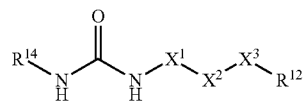

wherein:

$X^1$ is $CHR^{13}$;

$X^2$ is $CH_2$;

$X^3$ is $CH_2$, O, or S;

$R^{14}$ is optionally substituted heterocyclyl;

$R^{12}$ is optionally substituted heteroaryl or optionally substituted heterocyclyl;

$R^{13}$ is aralkyl;

or a pharmaceutically acceptable salt thereof.

2. A compound selected from (Exo_BJ-63)

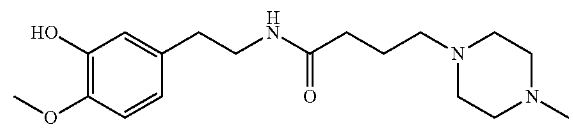

,

-continued (Exo_BJ-70)

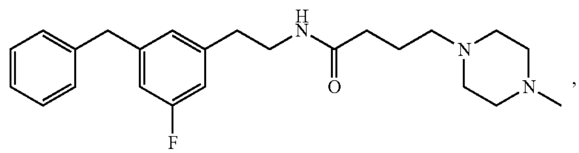

, (Exo_BJ-66)

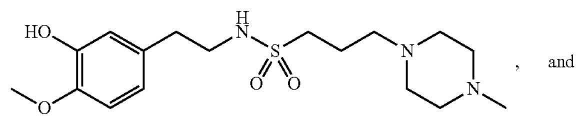

, and (Exo_BJ-58)

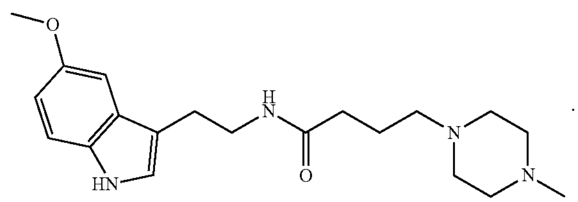

.

3. The compound of claim 1, wherein $R^{14}$ is a nitrogen-containing heterocycle, and a nitrogen of $R^{14}$ is substituted with alkyl or acyl.

4. The compound of claim 1, wherein a carbon of $R^{14}$ is substituted with heteroarylalkyl.

5. The compound of claim 1, wherein $X^3$ is $CH_2$.

6. The compound of claim 1, wherein $X^3$ is S.

7. The compound of claim 1, wherein $R^{12}$ is a nitrogen-containing heterocycle, and a nitrogen of $R^{12}$ is substituted with hydroxyalkyl.

8. The compound of claim 1, wherein $R^{12}$ is heteroaryl.

9. The compound of claim 1, wherein the compound is:

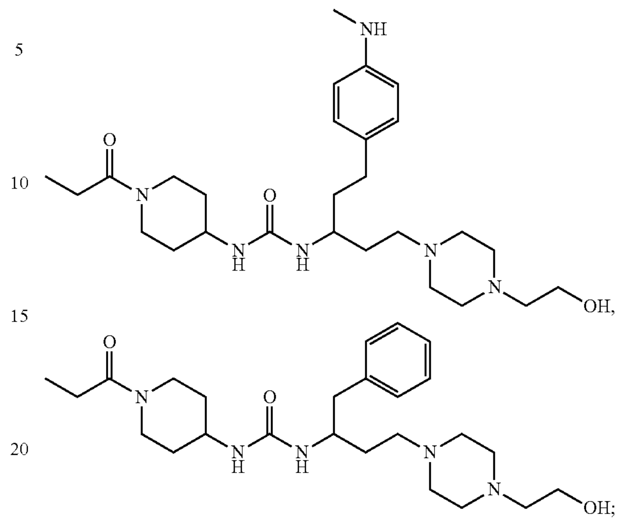

or a pharmaceutically acceptable salt thereof.

10. A pharmaceutical formulation comprising the compound according to claim 1, and a pharmaceutically acceptable carrier or excipient.

11. A method of treating a neurological disease or disorder in a subject in need thereof, comprising administering a compound of claim 1 to the subject.

12. A method of inhibiting amyloid beta formation in a subject, comprising administering a compound of claim 1 to the subject.

13. The compound of claim 1, wherein $R^{14}$ is optionally substituted piperidinyl.

14. The compound of claim 1, wherein $R^{13}$ is benzyl.

15. The compound of claim 1, wherein $R^{13}$ is homobenzyl.

16. The compound of claim 1, wherein the aryl of $R^{13}$ is substituted with amino.

17. The compound of claim 16, wherein the aryl of $R^{13}$ is substituted with methylamino.

18. The compound of claim 8, wherein $R^{12}$ is imidazolyl.

19. The compound of claim 18, wherein $R^{12}$ is substituted with hydroxyalkyl.

20. The compound of claim 19, wherein $R^{12}$ is substituted with hydroxyethyl.

* * * * *